United States Patent
Schief et al.

(10) Patent No.: US 9,707,290 B2
(45) Date of Patent: Jul. 18, 2017

(54) IMMUNOGENS OF HIV-1 BROADLY NEUTRALIZING ANTIBODIES, METHODS OF GENERATION AND USES THEREOF

(71) Applicants: INTERNATIONAL AIDS VACCINE INITIATIVE, New York, NY (US); THE SCRIPPS RESEARCH INSTITUTE, La Jolla, CA (US)

(72) Inventors: William R. Schief, New York, NY (US); Bruno E. Correia, La Jolla, CA (US); Daniel W. Kulp, New York, NY (US); Ron Jacak, New York, NY (US)

(73) Assignees: INTERNATIONAL AIDS VACCINE INITIATIVE, New York, NY (US); THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 14/642,929

(22) Filed: Mar. 10, 2015

(65) Prior Publication Data
US 2015/0238594 A1 Aug. 27, 2015

Related U.S. Application Data

(63) Continuation-in-part of application No. PCT/US2013/058934, filed on Sep. 10, 2013.

(60) Provisional application No. 61/699,221, filed on Sep. 10, 2012.

(51) Int. Cl.
| | |
|---|---|
| *A61K 39/21* | (2006.01) |
| *C07K 16/10* | (2006.01) |
| *C12N 7/00* | (2006.01) |
| *C12Q 1/68* | (2006.01) |
| *A61K 39/00* | (2006.01) |
| *A61K 39/12* | (2006.01) |

(52) U.S. Cl.
CPC .............. *A61K 39/21* (2013.01); *A61K 39/12* (2013.01); *C12N 7/00* (2013.01); *A61K 2039/64* (2013.01); *C12N 2740/16034* (2013.01)

(58) Field of Classification Search
CPC .......... A61K 2039/53; A61K 2039/505; A61K 39/12; C07K 2317/565; C07K 16/00
See application file for complete search history.

(56) References Cited

U.S. PATENT DOCUMENTS

2009/0136522 A1  5/2009  Haynes et al.

OTHER PUBLICATIONS

McEnery, Tapping the Sanguine Humor, IAVI Report, Mar.-Apr. 2012, vol. 16, No. 2, pp. 10-14.

3T43_A, PDB Accession No. 3T43_A, Chain A, Crystal Structure of HIV Epitope-Scaffold 4e10_1xiza_s0_006_c, Oct. 26, 2011 [online]. [Retrieved on Jan. 31, 2014]. Retrieved from the Internet <URL: http://www.ncbi_.nlm_.nih.gov/protein/354459665?sat=15&satkey=1302582>.

3LF6_A, PBD Accession No. 3LF6_A, Chain A, Crystal Structure of HIV Epitope-Scaffold 4e10_1xiza_s0_001_n, Sep. 22, 2010 [online]. [Retrieved on Jan. 31, 2014]. Retrieved from the Internet <URL: http://www.ncbi.nlm.nih.gov/protein/307568224?sat=16&satkey=10601794>.

B5C548, UniProtKB/TrEMBL entry B5C548_SALET, Jun. 13, 2012 [online]. [Retrieved on Jan. 31, 2014]. Retrieved from the Internet <URL: http://www.uniprot.org/uniprot/B5C548.txt?version=18 >.

Supplementary Partial European Search Report dated Mar. 31, 2016, which issued during prosecution of European Application No. 13835579.7.

Correia, et al. "Computational design of epitope-scaffolds allows induction of antibodies specific for a poorly immunogenic HIV vaccine epitope", Structure, Sep. 2010, 18(9):1116-1126.

Correia, et al. "Computational protein design using flexible backbone remodeling and resurfacing: case studies in structure-based antigen design" Journal of Molecular Biology, Jan. 2011, 405(1):284-297.

Correia, et al. "High-resolution structure prediction of a circular permutation loop" Protein Science, Nov. 2011, 20(11):1929-1934.

Tagliamonte, et al. "HIV p24 as Scaffold for Presenting Conformational HIV Env Antigens" Plos ONE, Aug. 2012, 7(8):e43318.

Wu, et al. "Focused Evolution of HIV-1 Neutralizing Antibodies Revealed by Structures and Deep Sequencing" Science, Sep. 2011, 333(6049):1593-1602.

Zolla-Pazner, et al. "Cross-Glade HIV-1 Neutralizing Antibodies Induced with V3-Scaffold Protein Immunogens following Priming with gp120 DNA" Journal of Virology, Oct. 2011, 85(19):9887-9898.

(Continued)

*Primary Examiner* — Janet L Andres
*Assistant Examiner* — Barry A Chestnut
(74) *Attorney, Agent, or Firm* — Vedder Price P.C.; Thomas J. Kowalski; Deborah L. Lu

(57) ABSTRACT

The present application relates to immunogens of broadly neutralizing monoclonal antibodies specific for HIV-1, such as broad and potent neutralizing monoclonal antibodies specific for HIV-1 and their gernation and methods of use. Broad neutralization suggests that the antibodies can neutralize HIV-1 isolates from different individuals. Immunogens or vaccines which may elicit such antibody associated responses are useful in pharmaceutical compositions for the prevention and treatment of HIV, and for the diagnosis and monitoring of HIV infection.

8 Claims, 4 Drawing Sheets

(56) References Cited

OTHER PUBLICATIONS

Supplementary European Search Report dated Jul. 19, 2016, which issued during prosecution of European Application No. 13835579.7.
International Preliminary Report on Patentability and Written Opinion of the International Searching Authority dated Mar. 10, 2015, which issued during prosecution of International Application No. PCT/US2013/058934.

Group 1

Group 3

IMMUNOGENS OF HIV-1 BROADLY NEUTRALIZING ANTIBODIES, METHODS OF GENERATION AND USES THEREOF

RELATED APPLICATIONS AND INCORPORATION BY REFERENCE

This application is a Continuation-In-Part of International Application No. PCT/US2013/058934 filed Sep. 10, 2013, which claims benefit of and priority to U.S. provisional patent application Ser. No. 61/699,221 filed Sep. 10, 2012.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted in ASCII format via EFS-Web and is hereby incorporated by reference in its entirety. Said ASCII copy, created on Sep. 26, 2013, is named 43094.99.2025_SL.txt and is 105,991 bytes in size.

FIELD OF THE INVENTION

This application relates to immunogens of broadly neutralizing monoclonal antibodies specific for HIV-1, such as broad and potent neutralizing monoclonal antibodies specific for HIV-1 and their gernation and methods of use. Broad neutralization suggests that the antibodies can neutralize HIV-1 isolates from different individuals. Immunogens or vaccines which may elicit such antibody associated responses are useful in pharmaceutical compositions for the prevention and treatment of HIV, and for the diagnosis and monitoring of HIV infection.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 June 19; 280(5371):1884-8). For fusion with its target cells, HIV-1 uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HIV-1 vaccines tested in human and/or non-human primate suggests that a successful vaccine will incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been daunting task (Phogat S, Wyatt R. Curr Pharm Des. 2007; 13:213-27, Phogat S, et al. J Intern Med. 2007 262:26-43, Karlsson Hedestam G B, et al Nat Rev Microbiol. 2008 6:143-55).

The ability to elicit broad and potent neutralizing antibodies is a major challenge in the development of an HIV-1 vaccine. Namely, HIV-1 has evolved an impressive array of strategies to evade antibody-mediated neutralization, bNAbs develop over time in a proportion of HIV-1 infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens.

Broadly cross-reactive monoclonal antibodies define epitopes for vaccine development against HIV and other highly mutable viruses. Crystal structures are available for several such antibody-epitope complexes, but methods are needed to translate that structural information into immunogens that re-elicit similar antibodies. Computational methods may be used to design epitope-scaffolds in which contiguous structural epitopes are transplanted to scaffold proteins for conformational stabilization and immune presentation. Epitope-scaffolds designed for the poorly immunogenic but conserved HIV epitope 4E10 exhibited high epitope structural mimicry, bound with higher affinities to monoclonal antibody (mAb) 4E10 than the cognate peptide, and inhibited HIV neutralization by HIV+ sera. Rabbit immunization with an epitope-scaffold induced antibodies with structural specificity highly similar to mAb 4E10, an important advance toward elicitation of neutralizing activity. The results demonstrate that computationally designed epitope-scaffolds are valuable as structure-specific serological reagents and as immunogens to elicit antibodies with predetermined structural specificity. (See Correia et al. Structure 2010 September 8; 18(9):1116-26). Furthermore, while a linear HIV peptide was reported to bind to 10E8 with an affinity of 17 nM (Huang et al Nature 2012), the 10E8 scaffolds described here bind to 10E8 with significantly higher affinities (higher by up to a factor of 1000). The improved affinities compared to the linear peptide may reflect conformational stabilization provided by the scaffold and may confer significant benefits for elicitation of structure-specific antibodies against this epitope.

Computational protein design has promise for vaccine design and other applications. HIV 4E10 epitope has been previously transplanted onto non-HIV protein scaffolds for structural stabilization and immune presentation. Two methods to optimize the structure of an antigen are developed, flexible backbone remodeling and resurfacing, and these methods are applied to a 4E10 scaffold. In flexible-backbone remodeling, an existing backbone segment is replaced by a de novo designed segment of prespecified length and secondary structure. With remodeling, a potentially immunodominant domain on the scaffold is replaced with a helix-loop segment that made intimate contact to the protein core. All three domain trim designs tested experimentally had improved thermal stability and similar binding affinity for the 4E10 antibody compared to the parent scaffold. A crystal structure of one design had a 0.8 Å backbone RMSD to the computational model in the rebuilt region. Comparison of parent and trimmed scaffold reactivity to anti-parent sera confirmed the deletion of an immunodominant domain. In resurfacing, the surface of an antigen outside a target epitope is redesigned to obtain variants that maintain only the target epitope. Resurfaced variants of two scaffolds were designed in which 50 positions amounting to 40% of the protein sequences were mutated. Surface-patch analyses indicated that most potential antibody footprints outside the 4E10 epitope were altered. The resurfaced variants maintained thermal stability and binding affinity. These results indicate that flexible-backbone remodeling and resurfacing are useful tools for antigen optimization and protein engineering generally. (see Correia et al. J Mol Biol, January 7; 405(1):284-97. Epub 2010 Oct. 20, 2011)

Citation or identification of any document in this application is not an admission that such document is available as prior art to the present invention.

SUMMARY OF THE INVENTION

The present invention relates to 10E8-scaffold vaccines to activate 10E8-like B cells, drive appropriate somatic mutation, and induce cross-reactive binding and neutralizing antibodies against HIV gp41 in rhesus macaques.

The invention is based, in part, on Applicant's surprising discovery of 10E8 scaffolds that bind to mature 10E8, and 10E8 scaffolds that bind with detectable affinity to germline 10E8. In contrast, only two of the five parent 4E10 scaffolds have detectable affinity for 10E8 which were considerably weaker (by a factor of ~30) than the corresponding 10E8 scaffolds. And, none of the parent 4E10 scaffolds have detectable affinity for germline 10E8. Thus, the mutations engineered onto the parent 4E10 scaffolds conferred an unexpected benefit of strong binding to mature 10E8 and in two cases, weak binding to germline 10E8. These 10E8 scaffolds are now enabled as 10E8 immunogens.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

Figure 1:
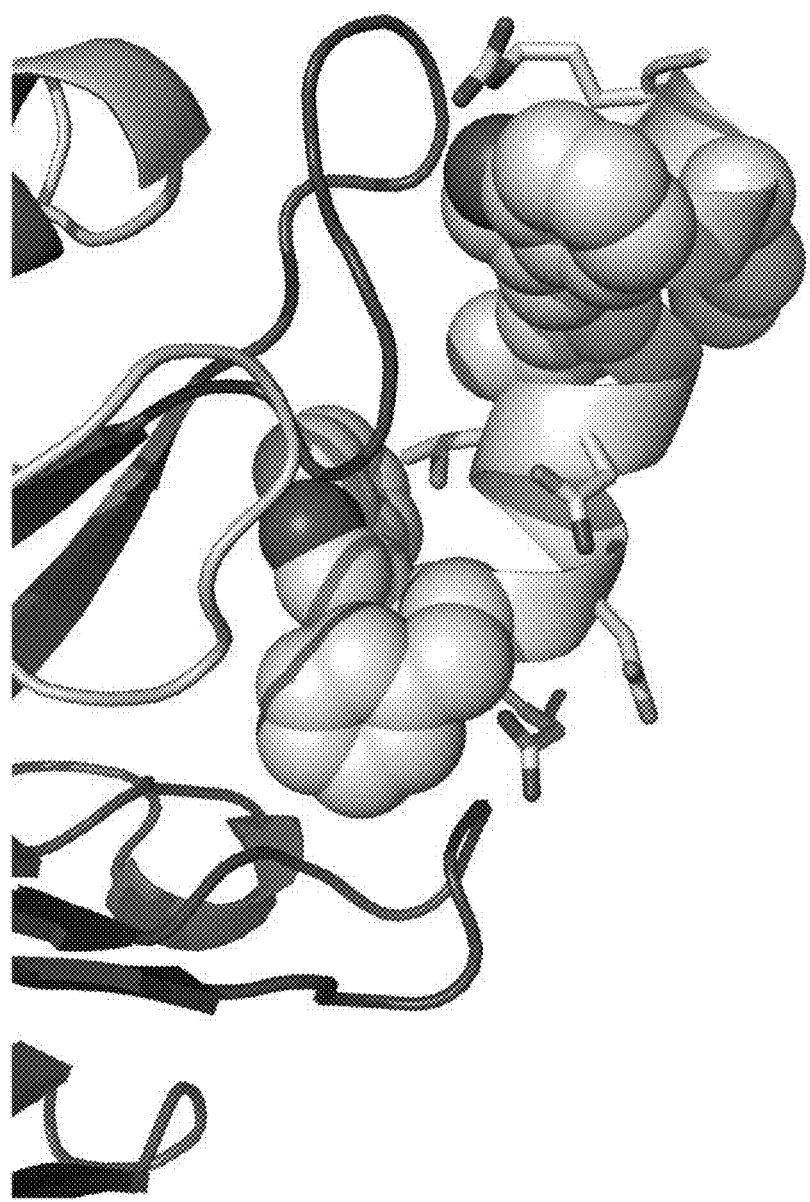
FIG. 1 depicts a peptide interacting with 10e8 and including residue numbering for relevant HIV epitope positions.

The neutralization index may be expressed as the ratio of normalized relative luminescence units (RLU) of the test viral strain to that of a control virus derived from the same test B cell culture supernatant. The cut-off values used to distinguish neutralizing hits may be determined by the neutralization index of a large number of "negative control wells" containing B cell culture supernatants derived from healthy donors. Such a method was successful for the isolation and characterization of PG9 and PG16.

The method of U.S. Pat. No. 7,386,232 may also be utilized for the screening of broad neutralizing antibodies. An envelope-enzyme fusion protein may be constructed by attaching an enzyme to the C-terminal end of an envelope protein. Virus particles which may comprise the fusion protein and wild type and/or soluble envelope glycoprotein may be generated and used to infect target cells in the presence of a patients' sera. Activities of enzyme measured in such infected cells are measures of virus binding and entry to the target cells that are mediated by the wild type viral envelope protein. Examples of enzymes that can be used to generate the fusion protein include, but are not limited to, luciferase, bacterial or placental alkaline phosphatase, β-galactosidase, and fluorescent proteins such as Green fluorescent protein or toxins. The assay, in general, can also be carried out in 96-well plate. Decreased enzyme activities in the presence of the sera indicate that there are neutralizing antibodies in the sera.

In another embodiment to isolate CD4bs-directed mAbs, a method of antigen-specific memory B-cell sorting (Wu et al (Science 329; 856 (2010))), together with single cell PCR, to amplify IgG heavy and light chain genes from the cDNA of individual B cells (J. F. Scheid et al., Broad diversity of neutralizing antibodies isolated from memory B cells in HIV-infected individuals. Nature 458, 636 (2009) and J. Wrammert et al., Nature 453, 667 (2008)) is preferred. Mutant Env probes are expressed with a tagged amino acid sequence that allows biotin labeling to distinguish them by FACS analysis after labeling with streptavidin (SA) conjugated to the fluorochromes allophycocyanin (SA-APC) or phycoerythrin (SA-PE), respectively. Peripheral blood mononuclear cells (PBMC) from a donor are incubated with the labeled mutant Env probes, and single antigen-specific memory B cells were sorted into wells of a microtiter plate after selecting for memory B cells (CD19+, CD20+, IgG+) that bind to the reference probe. The reference-probe-specific memory B cells are sorted and the matching heavy and light chain genes are amplified. After cloning into IgG1 expression vectors that reconstitute the heavy and light chain constant regions, the full IgG mAbs are expressed.

The cloning step for separating individual clones from the mixture of positive cells may be carried out using limiting dilution, micromanipulation, single cell deposition by cell sorting or another method known in the art. Preferably the cloning is carried out using limiting dilution.

The immortalized B cell clones of the invention can be used in various ways e.g. as a source of monoclonal antibodies, as a source of nucleic acid (DNA or mRNA) encoding a monoclonal antibody of interest, for research, etc.

The epitopes recognized by these antibodies may have a number of uses. The epitopes and mimotopes in purified or synthetic form can be used to raise immune responses (i.e. as a vaccine, or for the production of antibodies for other uses) or for screening patient serum for antibodies that immunoreact with the epitopes or mimotopes. Preferably, such an epitope or mimotope, or antigen which may comprise such an epitope or mimotope is used as a vaccine for raising an immune response. The antibodies of the invention can also be used in a method to monitor the quality of vaccines in particular to check that the antigen in a vaccine contains the correct immunogenic epitope in the correct conformation.

The epitopes may also be useful in screening for ligands that bind to said epitopes. Such ligands preferably block the epitopes and thus prevent infection.

Compounds which have a chemical structure selected using the invention, wherein said compounds are neutralizing antibody binders, form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the heavy chain; two Fab' fragments are obtained per antibody molecule;

(iii) F(ab')2, the fragment of the antibody that can be obtained by treating whole antibody with the enzyme pepsin without subsequent reduction; F(ab')2 is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus for example SF162 and/or JRCSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

An "isolated antibody" or "non-naturally occurring antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies which may comprise the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

An "antibody fragment" may comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

It should be understood that the proteins, including the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated or non-naturally occurring replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

This application discloses 10E8-scaffold vaccines to activate 10E8-like B cells, drive appropriate somatic mutation, and induce cross-reactive binding and neutralizing antibodies against HIV gp41 in rhesus macaques.

10E8 is a new, highly potent and broadly neutralizing antibody against HIV recently discovered. Induction of 10E8-like antibodies is a major goal for the HIV vaccine design field. This application relates to the identification of immunogens that bind to 10E8.

10E8 primarily targets a HIV Env membrane proximal external region (MPER) helix spanning residues 671-683 similarly to the antibody 4E10, but 10E8 is significantly more potent and lacks any detectable signs of autoreactivity or polyspecificity that have been noted for 4E10. 10E8 utilizes a long (22 aa) HCDR3 to make a majority of its important contacts, and the D gene in the mature 10E8 antibody is largely unmutated from the human germline. The conformation of the MPER helix bound to 10E8 has a very similar to the helix conformation as bound to 4E10. However, the interaction of 10E8 with its epitope has important differences compared to 4E10. 10E8 neutralization requires a K or R at position 683, whereas 4E10 does not interact with residues at that position. 10E8 utilizes its HCDR3 to contact its protein epitope and does not bind to lipids with significant affinity, whereas 4E10 is thought to employ its HCDR3 to contact lipid. The crystal structure of 10E8 bound to a MPER peptide seems to reveal the entire 10E8 epitope, in contrast to the case for 4E10.

A set of epitope-scaffolds for the 4E10 antibody were previously designed. These scaffolds stabilize the helical conformation of the epitope and bind to 4E10 very tightly. Crystal structures of several different scaffolds, both unliganded and liganded to 4E10, demonstrate that the scaffolds accurately mimick the desired helical epitope conformation. (See Correia et al Structure 2010, Correia at al JMB 2011, and Correia et al Protein Science 2011).

Two 4E10 scaffolds reported here are resurfaced variants of T93 that have not been published or publicly disclosed, 4E10_T93_RT1_1 and 4E10_T93_RT1_2.

Information about the 10E8 antibody lead to an evaluation if existing 4E10 scaffolds could be modified to act as epitope-scaffolds for the 10E8 epitope. While 10E8 is reported to require a K or R at position 683, none of the previously described 4E10 scaffolds had a K or R at that position. In an advantageous embodiment of the invention 4E10 scaffolds are re-designed to try to accommodate 10E8 binding, by (1) putting K at the scaffold position corresponding to 683 and (2) making a few selected mutations in the scaffold adjacent to the epitope to reduce the size of amino acids near but not within the epitope. A putative germline precursor for 10E8, as IgG is designed and produced.

The parent 4E10 scaffolds used are listed below, with the 4E10 epitope residues indicated in bold.

4E10_T93 (Correia et al Structure 2010; PDBID: 3LHP)
HHHHHHGSISDIRKDAEVRMDKAVEAFKNKLDKFKAAVRKVFPTEERIKD

WLKIVRGEAEQARVAVRNVGRDANDKAAALGKDKEINWFDISQSLWDVQK

LTDAAIKKIEAALADMEAWLTQG

4E10_T93_RT1_1 (resurfaced T93, not disclosed previously)
GEAQRVRQEAKERMKRAVEKFKKELKEFNTEVEKKEPRQQRIQKWEQIVE

ERAKKAEDEVKKVGKEANDRAAKLGQDPQVNWFDISQILWDVQKLTQEAI

EEIRKALEQMRRWLQRGLEHHHHHH

4E10_T93_RT1_2 (resurfaced T93, not disclosed previously)
GKADEVREKARRRMEQAVEEFKRRLRQFEEKVKQKEPRDDEINRWIDIVK

KKADEAKKRVEEVGDQANDEAAQLGNDPNVNWFDISQVLWDVQKLTEKAI

NDIDDALKKMKDWLESGLEHHHHHH

4E10_T117 (Correia et al Structure 2010; PDBID: 3LF6)
HHHHHHNAMQGIHFRRHYVRHLPKEVSQNDIIKALASPLINDGMVVSDFA

DHVITREQNFPTGLPVEPVGVAIPHTDSKYVRQNAISVGILAEPVNFEDA

GGEPDPVPVRVVFMLALGNWFDITNVLWWIMDVIQDEDFMQQLLVMNDDE

IYQSIYTRISE

4E10_T298 (Correia et al Prot Sci 2011; PDBID: 3T43)
GHHHHHHGSEVSQNDIIKALASPLINDGMVVSDFADHVITREQNAPTGLP

VEPVGVAIPHTDSKYVRQNAISVGILAEPVNFEDAGGEPDPVPVRVVFML

ALGNWFDITNVLWWIMDVIQDADFMQQLLVMNDDEIYQSIYTRISEAAGM

AGIHFRRHYVRHLPLEHHHHHH

10E8_T298v2
GSEVSQNDIIKALASPLINDGMVVSDFADHVITREQNAPTGLPVEPVGVA

IPHTDSKYVRQNAISVGILAEPVNFEDAGGEPDPVPVRVVFMLALGNWFD

ITNVLWWIKAVIQDADFMQQLLRMNDDEIYQSIYTRISEAAGMAGIHFRR

HYVRHLGLEHHHHHH

10E8_T117v2
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITNVLWWIKAVIQDEDFMQQLLVMNDDEIYQSIY

TRISELEHHHHHH

10E8_T93v2 encoded the following modifications relative to 4E10_T93:

GRDANDK (SEQ ID NO: 8)→GRDANDK (SEQ ID NO: 9) to reduce potential clash with 10E8 near L679 and K683 of epitope LWDVQKL (SEQ ID NO: 10)→LWDVKKL (SEQ ID NO: 11) to introduce K683 in the 10E8 epitope The histag was moved from N-terminus to C-terminus, to move the histag away from the epitope, away from potential interaction with 10E8.

10E8_T93v2_RT1_1 encoded the following modifications relative to 4E10_T93RT1_1:

a. GKEANDR (SEQ ID NO: 12)→GKEAADR (SEQ ID NO: 13) to reduce potential clash with 10E8 near L679 and K683 of epitope b. LWDVQKL (SEQ ID NO: 10)→LWDVKKL (SEQ ID NO: 11) to introduce K683 in the 10E8 epitope 10E8_T93v2_RT1_2 encoded the following modifications relative to 4E10_T93RT1_2:

GDQANDE (SEQ ID NO: 14)→GDQANDE (SEQ ID NO: 15) to reduce potential clash with 10E8 near L679 and K683 of epitope LWDVQKL (SEQ ID NO: 10)→LWDVKKL (SEQ ID NO: 11) to introduce K683 in the 10E8 epitope 10E8_T298v2 encoded the following modifications relative to 4E10_T298:

Removed N-terminal histag because unnecessary

Double mutation: LWWIMDVIQ (SEQ ID NO: 16)→LWWIKAVIQ (SEQ ID NO: 17) to introduce K683 in the 10E8 epitope, and to shrink the adjacent aspartic acid to an alanine to minimize chances of (favorable or unfavorable) antibody interactions while maintaining local helical secondary structure preference QQLLVMND (SEQ ID NO: 18)→QQLLRMND (SEQ ID NO: 19) to improve solubility by changing a surface-exposed hydrophobic amino acid to a polar, and to improve stability by changing from V (poor helical propensity) to R (good helical propensity) at a helical position in the structure.

Adding an extra glycine before the C-terminal his-tag to improve Ni++ purification by improving exposure of the his-tag 10E8_T117v2 encoded the following modifications relative to 4E10_T117:

a. Double mutation: LWWIMDVI (SEQ ID NO: 20)→LWWIKAVI (SEQ ID NO: 21) to introduce K683 in the epitope, and to shrink the adjacent aspartic acid to an alanine to minimize chances of (favorable or unfavorable) antibody interactions while maintaining local helical secondary structure preference.

Thus of all the constructs above, the following produced soluble protein:

1. 10E8_T93v2
2. 10E8_T93v2_RT1_1
3. 10E8_T93v2_RT1_2
4. 10E8_T298v2
5. 10E8_T117v2

These 10E8 scaffolds, and their parent 4E10 scaffolds (also produced in *E. coli*), are characterized by SECMALS (multi-angle light scattering coupled in-line with size exclusion chromatography) to determine their solution multimeric state, and the five scaffolds with well-defined multimeric state are tested for binding to both mature and germline 10E8.

10E8_T93v2, 10E8_T93v2_RT1_2, 10E8_T298v2, and 10E8_T117v2 are all monomeric in solution. 10E8_tet_e is a tetramer in solution, as designed. T93v2_RT1_1 is a mixture of monomer and dimer in solution so is not pursued further. The fact that 10E8_T117v2 and 10E8_T298v2 are monomers is a major advance because their parent scaffolds (4E10_T117 and 4E10_T298) both formed dimers in solution that buried the epitope at the dimer interface. The thermal stability of 10E8_T93v2_RT1_2 and 10E8_T298v2 are also assessed by circular dichroism (CD) spectrometry; both scaffolds are so highly stable that a lower bound on the melting temperatures of >90° C. is set. Again this was a major improvement on the parent scaffolds which had melting temperatures of 79° C. (4E10_T93) and 48° C. (4E10_T298).

Surprisingly, five 10E8 scaffolds bind to mature 10E8, and two 10E8 scaffolds bound with detectable affinity to germline 10E8. The affinities for mature 10E8 were particularly high for T117v2 (Kd=91 pM) and T298v2 (Kd=172 pM). The affinities for T93v2 (Kd~5 nM but SPR kinetics difficult to fit) and T93v2_RT1_2 (Kd=800 pM) are lower than for T117v2 and T298v2 but are still considerably better than the value reported for mature 10E8 binding to peptide (Kd~20 nM). 10E8_tet2_e is also observed to bind tightly but the SPR kinetics could not be fit owing to multivalent avidity in the interaction between the tetramer and the 10E8 antibody-coated sensor surface. T93v2_RT1_1 is not tested for 10E8 binding because it is not a homogeneous monomer in solution. For germline 10E8, scaffolds T117v2 (Kd (10E8GL)~30 mcM) and T298v2 (Kd(10E8GL)=105 mcM) have measurable affinities, but the other scaffolds did not.

In contrast, only two of the five parent 4E10 scaffolds have detectable affinity for 10E8—both 4E10_T117 and 4E10_T298 bound 10E8 with Kd=3 nM, considerably weaker (by a factor of ~30) than the corresponding 10E8 scaffolds. And, none of the parent 4E10 scaffolds have detectable affinity for germline 10E8.

Thus, the mutations engineered onto the parent 4E10 scaffolds conferred an unexpected benefit of strong binding to mature 10E8 and in two cases, weak binding to germline 10E8. These 10E8 scaffolds are now enabled as 10E8 immunogens.

HIV includes substantial sequence variation at exposed positions within and around the 10e8 contact residues. For reference to residues exposed in and around the 10e8 epitope, FIG. 1 shows a portion of the structure of the 10e8 antibody bound to an HIV peptide. HIV amino acids that either interact directly with 10e8 or that are exposed around the 10e8 contact positions are shown in spacefill or stick representation. Those residues in spacefill are highly conserved in HIV (>99%), while residues in stick are more variable.

TABLE 1

HIV sequence segments over positions 671-683, ranked by frequency of occurrence. The most common 100 segments are shown. Sequence positions indicated with a star are positions that are included in 10e8 scaffolds. Bold positions are those with substantial sequence variation. A total of 2870 HIV sequences from all clades were used for this analysis.

| Rank | %_of_seqs | cumulative_% | HIV_sequence_671-683 |
|---|---|---|---|
| 1 | 0.0997 | 0.0997 | NWFDITNWLWYIK |
| 2 | 0.0760 | 0.1757 | NWFDITKWLWYIK |
| 3 | 0.0617 | 0.2374 | NWFDISNWLWYIK |
| 4 | 0.0495 | 0.2869 | NWFSITKWLWYIK |
| 5 | 0.0352 | 0.3221 | NWFNITNWLWYIK |
| 6 | 0.0335 | 0.3556 | NWFSITNWLWYIK |
| 7 | 0.0275 | 0.3831 | SWFDITNWLWYIK |
| 8 | 0.0254 | 0.4085 | NWFDISNWLWYIR |
| 9 | 0.0254 | 0.4339 | NWFDISKWLWYIK |
| 10 | 0.0223 | 0.4562 | SWFDISNWLWYIK |
| 11 | 0.0216 | 0.4778 | NWFNISNWLWYIK |

TABLE 1-continued

HIV sequence segments over positions 671-683, ranked by frequency of occurrence. The most common 100 segments are shown. Sequence positions indicated with a star are positions that are included in 10e8 scaffolds. Bold positions are those with substantial sequence variation. A total of 2870 HIV sequences from all clades were used for this analysis.

| Rank | %_of_seqs | cumulative_% | HIV_sequence_671-683 |
|---|---|---|---|
| 12 | 0.0178 | 0.4956 | NWFSITNWLWYIR |
| 13 | 0.0160 | 0.5116 | NWFDITNWLWYIR |
| 14 | 0.0157 | 0.5273 | SWFSITNWLWYIK |
| 15 | 0.0153 | 0.5426 | NWFDITRWLWYIK |
| 16 | 0.0132 | 0.5558 | SWFDISNWLWYIR |
| 17 | 0.0129 | 0.5687 | NWFSISNWLWYIK |
| 18 | 0.0122 | 0.5809 | TWFDITNWLWYIR |
| 19 | 0.0122 | 0.5931 | TWFDISNWLWYIR |
| 20 | 0.0122 | 0.6053 | NWLDITKWLWYIK |
| 21 | 0.0115 | 0.6168 | NWFDITSWLWYIK |
| 22 | 0.0115 | 0.6283 | NWFDITQWLWYIK |
| 23 | 0.0108 | 0.6391 | SWFSITNWLWYIR |
| 24 | 0.0101 | 0.6492 | SWFDITKWLWYIK |
| 25 | 0.0094 | 0.6586 | SWFDITNWLWYIR |
| 26 | 0.0094 | 0.668 | NWFDISKWLWYIR |
| 27 | 0.0091 | 0.6771 | NWFNITQWLWYIK |
| 28 | 0.0087 | 0.6858 | NWFSISNWLWYIR |
| 29 | 0.0087 | 0.6945 | NWFGITKWLWYIK |
| 30 | 0.0084 | 0.7029 | NWFSITQWLWYIK |
| 31 | 0.0084 | 0.7113 | NWFDISRWLWYIK |
| 32 | 0.0077 | 0.719 | SWFNITNWLWYIR |
| 33 | 0.0073 | 0.7263 | TWFDISNWLWYIR |
| 34 | 0.0073 | 0.7336 | NWFNITKWLWYIK |
| 35 | 0.0070 | 0.7406 | TWFDITKWLWYIK |
| 36 | 0.0066 | 0.7472 | SWFNITNWLWYIK |
| 37 | 0.0066 | 0.7538 | SWFNISNWLWYIK |
| 38 | 0.0063 | 0.7601 | NWFNISNWLWYIR |
| 39 | 0.0059 | 0.766 | NWFSISKWLWYIK |
| 40 | 0.0059 | 0.7719 | NWFNITNWLWYIR |
| 41 | 0.0059 | 0.7778 | NWFDITKWLWYIR |
| 42 | 0.0056 | 0.7834 | SWFSITKWLWYIK |
| 43 | 0.0052 | 0.7886 | NWFTITNWLWYIK |
| 44 | 0.0049 | 0.7935 | SWFSISNWLWYIR |
| 45 | 0.0042 | 0.7977 | NWFDITHWLWYIK |
| 46 | 0.0038 | 0.8015 | SWFDITQWLWYIK |
| 47 | 0.0038 | 0.8053 | NWFSITHWLWYIK |
| 48 | 0.0035 | 0.8088 | TWFDITNWLWYIR |
| 49 | 0.0031 | 0.8119 | SWFNISNWLWYIR |
| 50 | 0.0031 | 0.815 | SWFDITKWLWYIR |
| 51 | 0.0031 | 0.8181 | NWFGITNWLWYIK |
| 52 | 0.0031 | 0.8212 | NWFDISRWLWYIR |
| 53 | 0.0031 | 0.8243 | NWFDISHWLWYIR |
| 54 | 0.0028 | 0.8271 | NWFNISKWLWYIK |
| 55 | 0.0028 | 0.8299 | NWFDITQWLWYIR |
| 56 | 0.0024 | 0.8323 | SWFSISNWLWYIK |
| 57 | 0.0024 | 0.8347 | SWFSISKWLWYIK |
| 58 | 0.0024 | 0.8371 | NWFDISSWLWYIK |
| 59 | 0.0021 | 0.8392 | SWLDITKWLWYIK |
| 60 | 0.0021 | 0.8413 | SWFSITQWLWYIK |
| 61 | 0.0021 | 0.8434 | SWFDISKWLWYIR |
| 62 | 0.0021 | 0.8455 | SWFDISKWLWYIK |
| 63 | 0.0021 | 0.8476 | NWFSISQWLWYIK |
| 64 | 0.0021 | 0.8497 | NWFEISNWLWYIK |
| 65 | 0.0021 | 0.8518 | NWFDITSWLWYIR |
| 66 | 0.0017 | 0.8535 | SWFDITRWLWYIR |
| 67 | 0.0017 | 0.8552 | NWFTISNWLWYIK |
| 68 | 0.0017 | 0.8569 | NWFEISKWLWYIK |
| 69 | 0.0017 | 0.8586 | NWFDISQWLWYIK |
| 70 | 0.0014 | 0.86 | TWFGITNWLWYIR |
| 71 | 0.0014 | 0.8614 | TWFDITKWLWYIR |
| 72 | 0.0014 | 0.8628 | SWFTITNWLWYIK |
| 73 | 0.0014 | 0.8642 | SWFDISSWLWYIR |
| 74 | 0.0014 | 0.8656 | SWFDISRWLWYIR |
| 75 | 0.0014 | 0.867 | NWFSITKWLWYIR |
| 76 | 0.0014 | 0.8684 | NWFNITHWLWYIK |
| 77 | 0.0014 | 0.8698 | NWFGISNWLWYIK |
| 78 | 0.0014 | 0.8712 | NWFDISSWLWYIR |
| 79 | 0.0010 | 0.8722 | TWFNISNWLWYIK |
| 80 | 0.0010 | 0.8732 | TWFDITRWLWYIK |

TABLE 1-continued

HIV sequence segments over positions 671-683, ranked by frequency of occurrence. The most common 100 segments are shown. Sequence positions indicated with a star are positions that are included in 10e8 scaffolds. Bold positions are those with substantial sequence variation. A total of 2870 HIV sequences from all clades were used for this analysis.

| Rank | %_of_seqs | cumulative_% | HIV_sequence_671-683 |
|---|---|---|---|
| 81 | 0.0010 | 0.8742 | TWFDITQWLWYIK |
| 82 | 0.0010 | 0.8752 | TWFDISHWLWYIK |
| 83 | 0.0010 | 0.8762 | SWFSITQWLWYIR |
| 84 | 0.0010 | 0.8772 | SWFSITHWLWYIK |
| 85 | 0.0010 | 0.8782 | SWFSISQWLWYIK |
| 86 | 0.0010 | 0.8792 | SWFNITQWLWYIK |
| 87 | 0.0010 | 0.8802 | SWFNITHWLWYIK |
| 88 | 0.0010 | 0.8812 | SWFEITNWLWYIK |
| 89 | 0.0010 | 0.8822 | SWFEISNWLWYIR |
| 90 | 0.0010 | 0.8832 | SWFDITSWLWYIR |
| 91 | 0.0010 | 0.8842 | SWFDISQWLWYIK |
| 92 | 0.0010 | 0.8852 | NWFXITNWLWYIK |
| 93 | 0.0010 | 0.8862 | NWFSITSWLWYIK |
| 94 | 0.0010 | 0.8872 | NWFSITRWLWYIK |
| 95 | 0.0010 | 0.8882 | NWFSITKWLRYIQ |
| 96 | 0.0010 | 0.8892 | NWFSITHWLWYIR |
| 97 | 0.0010 | 0.8902 | NWFSISRWLWYIK |
| 98 | 0.0010 | 0.8912 | NWFNITRWLWYIK |
| 99 | 0.0010 | 0.8922 | NWFNITEWLWYIK |
| 100 | 0.0010 | 0.8932 | NWFNISQWLWYIK |

TABLE 2

HIV Glade C sequence segments over positions 671-683, ranked by frequency of occurrence. The most common 100 Glade C segments are shown. Sequence positions indicated with a star are positions that are included in 10e8 scaffolds. Bold positions are those with substantial sequence variation. A total of 739 HIV Glade C sequences were used for this analysis.

| Rank | %_of_seqs | cumulative_% | HIV_sequence_671-683 |
|---|---|---|---|
| 1 | 0.0785 | 0.0785 | NWFSITKWLWYIK |
| 2 | 0.0690 | 0.1475 | NWFDITNWLWYIK |
| 3 | 0.0568 | 0.2043 | NWFDITKWLWYIK |
| 4 | 0.0501 | 0.2544 | NWFNITNWLWYIK |
| 5 | 0.0419 | 0.2963 | NWFSITNWLWYIK |
| 6 | 0.0338 | 0.3301 | NWFNISNWLWYIK |
| 7 | 0.0311 | 0.3612 | SWFSITNWLWYIK |
| 8 | 0.0298 | 0.391 | SWFDISNWLWYIK |
| 9 | 0.0284 | 0.4194 | NWFDISNWLWYIK |
| 10 | 0.0244 | 0.4438 | SWFDITNWLWYIK |
| 11 | 0.0217 | 0.4655 | SWFNITNWLWYIR |
| 12 | 0.0189 | 0.4844 | NWFGITKWLWYIK |
| 13 | 0.0176 | 0.502 | SWFNITNWLWYIK |
| 14 | 0.0176 | 0.5196 | SWFNISNWLWYIK |
| 15 | 0.0176 | 0.5372 | NWFDISKWLWYIK |
| 16 | 0.0162 | 0.5534 | SWFSITKWLWYIK |
| 17 | 0.0162 | 0.5696 | SWFDISNWLWYIR |
| 18 | 0.0149 | 0.5845 | SWFSITNWLWYIR |
| 19 | 0.0149 | 0.5994 | NWFSISNWLWYIK |
| 20 | 0.0135 | 0.6129 | SWFDITNWLWYIR |
| 21 | 0.0122 | 0.6251 | SWFDITKWLWYIK |
| 22 | 0.0122 | 0.6373 | NWFSITNWLWYIR |
| 23 | 0.0108 | 0.6481 | TWFDITNWLWYIK |
| 24 | 0.0108 | 0.6589 | NWFDITNWLWYIR |
| 25 | 0.0095 | 0.6684 | NWFNITNWLWYIR |
| 26 | 0.0095 | 0.6779 | NWFNITKWLWYIK |
| 27 | 0.0095 | 0.6874 | NWFDISNWLWYIR |
| 28 | 0.0081 | 0.6955 | TWFDITKWLWYIK |
| 29 | 0.0081 | 0.7036 | TWFDISNWLWYIK |
| 30 | 0.0081 | 0.7117 | SWFSISNWLWYIR |
| 31 | 0.0081 | 0.7198 | NWFNISNWLWYIR |
| 32 | 0.0081 | 0.7279 | NWFDITRWLWYIK |
| 33 | 0.0068 | 0.7347 | SWFSISKWLWYIK |
| 34 | 0.0068 | 0.7415 | SWFNISNWLWYIR |
| 35 | 0.0054 | 0.7469 | NWFSISKWLWYIK |
| 36 | 0.0054 | 0.7523 | NWFNITQWLWYIK |
| 37 | 0.0054 | 0.7577 | NWFDITSWLWYIK |
| 38 | 0.0054 | 0.7631 | NWFDISRWLWYIK |
| 39 | 0.0041 | 0.7672 | TWFDITNWLWYIR |
| 40 | 0.0041 | 0.7713 | SWFDISRWLWYIK |
| 41 | 0.0041 | 0.7754 | NWFSITQWLWYIK |

TABLE 2-continued

HIV Glade C sequence segments over positions 671-683, ranked by frequency of occurrence. The most common 100 Glade C segments are shown. Sequence positions indicated with a star are positions that are included in 10e8 scaffolds. Bold positions are those with substantial sequence variation. A total of 739 HIV Glade C sequences were used for this analysis.

| Rank | %_of_seqs | cumulative_% | HIV_sequence_671-683 |
|---|---|---|---|
| 42 | 0.0041 | 0.7795 | NWFSISNWLWYIR |
| 43 | 0.0041 | 0.7836 | NWFNISKWLWYIK |
| 44 | 0.0041 | 0.7877 | NWFGITNWLWYIK |
| 45 | 0.0041 | 0.7918 | NWFDITQWLWYIK |
| 46 | 0.0041 | 0.7959 | NWFDITKWLWYIR |
| 47 | 0.0041 | 0.8 | NWFDISKWLWYIR |
| 48 | 0.0041 | 0.8041 | DWFNISNWLWYIK |
| 49 | 0.0027 | 0.8068 | TWFGITNWLWYIR |
| 50 | 0.0027 | 0.8095 | TWFGITNWLWYIK |
| 51 | 0.0027 | 0.8122 | TWFDISNWLWYIR |
| 52 | 0.0027 | 0.8149 | SWFSISSWLWYIK |
| 53 | 0.0027 | 0.8176 | SWFSISQWLWYIK |
| 54 | 0.0027 | 0.8203 | SWFSISNWLWYIK |
| 55 | 0.0027 | 0.823 | SWFSISHWLWYIK |
| 56 | 0.0027 | 0.8257 | SWFDITSWLWYIR |
| 57 | 0.0027 | 0.8284 | SWFDITRWLWYIR |
| 58 | 0.0027 | 0.8311 | SWFDITQWLWYIK |
| 59 | 0.0027 | 0.8338 | SWFDITKWLWYIR |
| 60 | 0.0027 | 0.8365 | SWFDISSWLWYIR |
| 61 | 0.0027 | 0.8392 | NWFSITHWLWYIR |
| 62 | 0.0027 | 0.8419 | NWFKITKWLWYIK |
| 63 | 0.0027 | 0.8446 | NWFDITHWLWYIK |
| 64 | 0.0027 | 0.8473 | NWFDISRWLWYIR |
| 65 | 0.0027 | 0.85 | NWFDISKWLGYIQ |
| 66 | 0.0027 | 0.8527 | DWFSISNWLWYIK |
| 67 | 0.0014 | 0.8541 | TWFSLTNWLWYIR |
| 68 | 0.0014 | 0.8555 | TWFSITNWLWYIR |
| 69 | 0.0014 | 0.8569 | TWFSITNWLWYIK |
| 70 | 0.0014 | 0.8583 | TWFSISNWLWYIR |
| 71 | 0.0014 | 0.8597 | TWFSISNWLWYIK |
| 72 | 0.0014 | 0.8611 | TWFGISSWLWYIK |
| 73 | 0.0014 | 0.8625 | TWFGISNWLWYIK |
| 74 | 0.0014 | 0.8639 | TWFDITRWLWYIK |
| 75 | 0.0014 | 0.8653 | TWFDITKWPWYIK |
| 76 | 0.0014 | 0.8667 | TWFDISSWLWYIR |
| 77 | 0.0014 | 0.8681 | TWFDISKWLWYIR |
| 78 | 0.0014 | 0.8695 | TWFDISHWLWYIK |
| 79 | 0.0014 | 0.8709 | SWWDISKWLWYIR |
| 80 | 0.0014 | 0.8723 | SWVDISNWLWYIR |
| 81 | 0.0014 | 0.8737 | SWLSITNWLWYIR |
| 82 | 0.0014 | 0.8751 | SWLSISNWLWYIR |
| 83 | 0.0014 | 0.8765 | SWFTLSNWLWYIR |
| 84 | 0.0014 | 0.8779 | SWFTITNWLWYIK |
| 85 | 0.0014 | 0.8793 | SWFTITKWLWYIR |
| 86 | 0.0014 | 0.8807 | SWFTISNWLWYIR |
| 87 | 0.0014 | 0.8821 | SWFSITQWLWYIK |
| 88 | 0.0014 | 0.8835 | SWFSITKWLRYIQ |
| 89 | 0.0014 | 0.8849 | SWFSITHWLWYIR |
| 90 | 0.0014 | 0.8863 | SWFNMTNWLWYIK |
| 91 | 0.0014 | 0.8877 | SWFNITQWLWYIK |
| 92 | 0.0014 | 0.8891 | SWFNITNWLWCIK |
| 93 | 0.0014 | 0.8905 | SWFNITNWLW-IK |
| 94 | 0.0014 | 0.8919 | SWFNITKWLWYIK |
| 95 | 0.0014 | 0.8933 | SWFNITHWLWYIK |
| 96 | 0.0014 | 0.8947 | SWFNISSWLWYIR |
| 97 | 0.0014 | 0.8961 | SWFNISKWLWYIK |
| 98 | 0.0014 | 0.8975 | SWFNISHWLWYIK |
| 99 | 0.0014 | 0.8989 | SWFHITNWLWYIK |
| 100 | 0.0014 | 0.9003 | SWFGITQWLWYIK |

TABLE 3

HIV Glade B sequence segments over positions 671-683, ranked by frequency of occurrence. The most common 100 Glade B segments are shown. Sequence positions indicated with a star are positions that are included in 10e8 scaffolds. Bold positions are those with substantial sequence variation. A total of 898 HIV Glade B sequences were used for this analysis.

| Rank | %_of_seqs | cumulative_% | HIV_sequence_671-683 |
|---|---|---|---|
| 1 | 0.1459 | 0.1459 | NWFDITNWLWYIK |
| 2 | 0.1147 | 0.2606 | NWFDITKWLWYIK |

TABLE 3-continued

HIV Glade B sequence segments over positions 671-683, ranked by frequency of occurrence. The most common 100 Glade B segments are shown. Sequence positions indicated with a star are positions that are included in 10e8 scaffolds. Bold positions are those with substantial sequence variation. A total of 898 HIV Glade B sequences were used for this analysis.

| Rank | %_of_seqs | cumulative_% | HIV_sequence_671-683 |
|---|---|---|---|
| 3 | 0.0668 | 0.3274 | NWFDISNWLWYIK |
| 4 | 0.0434 | 0.3708 | NWFSITNWLWYIK |
| 5 | 0.0379 | 0.4087 | NWFNITNWLWYIK |
| 6 | 0.0356 | 0.4443 | NWFSITKWLWYIK |
| 7 | 0.0301 | 0.4744 | SWFDITNWLWYIK |
| 8 | 0.0256 | 0.5 | NWFDISKWLWYIK |
| 9 | 0.0223 | 0.5223 | NWFSITNWLWYIR |
| 10 | 0.0223 | 0.5446 | NWFDITQWLWYIK |
| 11 | 0.0212 | 0.5658 | NWFDITNWLWYIR |
| 12 | 0.0178 | 0.5836 | NWFDISNWLWYIR |
| 13 | 0.0167 | 0.6003 | SWFDISNWLWYIK |
| 14 | 0.0156 | 0.6159 | NWFNISNWLWYIK |
| 15 | 0.0145 | 0.6304 | SWFSITNWLWYIR |
| 16 | 0.0145 | 0.6449 | NWFNITQWLWYIK |
| 17 | 0.0134 | 0.6583 | TWFDITNWLWYIK |
| 18 | 0.0134 | 0.6717 | NWFDITSWLWYIK |
| 19 | 0.0122 | 0.6839 | NWFSISNWLWYIK |
| 20 | 0.0100 | 0.6939 | SWFDITKWLWYIK |
| 21 | 0.0100 | 0.7039 | SWFDISNWLWYIR |
| 22 | 0.0100 | 0.7139 | NWFTITNWLWYIK |
| 23 | 0.0100 | 0.7239 | NWFSISNWLWYIR |
| 24 | 0.0089 | 0.7328 | SWFSITNWLWYIK |
| 25 | 0.0089 | 0.7417 | SWFDITNWLWYIR |
| 26 | 0.0089 | 0.7506 | NWFSITQWLWYIK |
| 27 | 0.0089 | 0.7595 | NWFSITHWLWYIK |
| 28 | 0.0089 | 0.7684 | NWFDITHWLWYIK |
| 29 | 0.0067 | 0.7751 | TWFDITNWLWYIR |
| 30 | 0.0067 | 0.7818 | SWFDITQWLWYIK |
| 31 | 0.0067 | 0.7885 | NWFDITRWLWYIK |
| 32 | 0.0056 | 0.7941 | TWFDISNWLWYIR |
| 33 | 0.0056 | 0.7997 | NWFDITQWLWYIR |
| 34 | 0.0056 | 0.8053 | NWFDISKWLWYIR |
| 35 | 0.0045 | 0.8098 | TWFDISNWLWYIK |
| 36 | 0.0045 | 0.8143 | SWFSITQWLWYIK |
| 37 | 0.0045 | 0.8188 | NWFTISNWLWYIK |
| 38 | 0.0045 | 0.8233 | NWFNITKWLWYIK |
| 39 | 0.0045 | 0.8278 | NWFDITKWLWYIR |
| 40 | 0.0033 | 0.8311 | TWFDITKWLWYIK |
| 41 | 0.0033 | 0.8344 | SWFDISQWLWYIK |
| 42 | 0.0033 | 0.8377 | NWFSITSWLWYIK |
| 43 | 0.0033 | 0.841 | NWFSISQWLWYIK |
| 44 | 0.0033 | 0.8443 | NWFSISKWLWYIK |
| 45 | 0.0033 | 0.8476 | NWFNITNWLWYIR |
| 46 | 0.0033 | 0.8509 | NWFDISSWLWYIK |
| 47 | 0.0033 | 0.8542 | NWFDISQWLWYIK |
| 48 | 0.0022 | 0.8564 | SWFSITQWLWYIR |
| 49 | 0.0022 | 0.8586 | SWFSITHWLWYIK |
| 50 | 0.0022 | 0.8608 | SWFSISNWLWYIK |
| 51 | 0.0022 | 0.863 | SWFNISNWLWYIK |
| 52 | 0.0022 | 0.8652 | SWFDITSWLWYIK |
| 53 | 0.0022 | 0.8674 | SWFDITKWLWYIR |
| 54 | 0.0022 | 0.8696 | SWFDISKWLWYIK |
| 55 | 0.0022 | 0.8718 | NWFXITNWLWYIK |
| 56 | 0.0022 | 0.874 | NWFNITHWLWYIK |
| 57 | 0.0022 | 0.8762 | NWFNITEWLWYIK |
| 58 | 0.0022 | 0.8784 | NWFGITKWLWYIK |
| 59 | 0.0022 | 0.8806 | NWFEISNWLWYIK |
| 60 | 0.0022 | 0.8828 | NWFDITHWLWYIR |
| 61 | 0.0022 | 0.885 | NWFDISRWLWYIK |
| 62 | 0.0022 | 0.8872 | DWFSITKWLWYIK |
| 63 | 0.0011 | 0.8883 | TWFSITNWLWYIK |
| 64 | 0.0011 | 0.8894 | TWFNITNWLWYIR |
| 65 | 0.0011 | 0.8905 | TWFNISNWLWYIK |
| 66 | 0.0011 | 0.8916 | TWFGLNKWMRYIK |
| 67 | 0.0011 | 0.8927 | TWFGITNWLWYIR |
| 68 | 0.0011 | 0.8938 | TWFDLTNWLWYIR |
| 69 | 0.0011 | 0.8949 | TWFDITQWLWYIK |
| 70 | 0.0011 | 0.896 | TWFDITKWLWYIR |
| 71 | 0.0011 | 0.8971 | TWFDISNWMRYIQ |

TABLE 3-continued

HIV Glade B sequence segments over positions 671-683, ranked by frequency of occurrence. The most common 100 Glade B segments are shown. Sequence positions indicated with a star are positions that are included in 10e8 scaffolds. Bold positions are those with substantial sequence variation. A total of 898 HIV Glade B sequences were used for this analysis.

| Rank | %_of_seqs | cumulative_% | HIV_sequence_671-683 |
|---|---|---|---|
| 72 | 0.0011 | 0.8982 | TWFDISKWLWYIK |
| 73 | 0.0011 | 0.8993 | SXFSITNWLWYIR |
| 74 | 0.0011 | 0.9004 | SWYDISNWLWYIK |
| 75 | 0.0011 | 0.9015 | SWLDITNWLWYIR |
| 76 | 0.0011 | 0.9026 | SWLDITKWLWYIK |
| 77 | 0.0011 | 0.9037 | SWLDISNWLKYIK |
| 78 | 0.0011 | 0.9048 | SWLDISNWLGYIK |
| 79 | 0.0011 | 0.9059 | SWLDISHWLWYIR |
| 80 | 0.0011 | 0.907 | SWFTITNWLWYIK |
| 81 | 0.0011 | 0.9081 | SWFTISKWLWYIK |
| 82 | 0.0011 | 0.9092 | SWFSLTNWLWYIK |
| 83 | 0.0011 | 0.9103 | SWFSIVNWLWYIK |
| 84 | 0.0011 | 0.9114 | SWFSITNWLRYIK |
| 85 | 0.0011 | 0.9125 | SWFSITKWLWYIK |
| 86 | 0.0011 | 0.9136 | SWFSITEWLWYIK |
| 87 | 0.0011 | 0.9147 | SWFSISNWLWYIR |
| 88 | 0.0011 | 0.9158 | SWFQLSKWMWYIK |
| 89 | 0.0011 | 0.9169 | SWFNITNWLWYIR |
| 90 | 0.0011 | 0.918 | SWFNITNWLWYIK |
| 91 | 0.0011 | 0.9191 | SWFNITHWLWYIK |
| 92 | 0.0011 | 0.9202 | SWFNISNWLWYIR |
| 93 | 0.0011 | 0.9213 | SWFGITQWLWYIK |
| 94 | 0.0011 | 0.9224 | SWFEITNWLWYIK |
| 95 | 0.0011 | 0.9235 | SWFEISNWLWYIK |
| 96 | 0.0011 | 0.9246 | SWFDLTNWLWYIR |
| 97 | 0.0011 | 0.9257 | SWFDITSWLWYIR |
| 98 | 0.0011 | 0.9268 | SWFDITRWMKYVK |
| 99 | 0.0011 | 0.9279 | SWFDITNWLWYIQ |
| 100 | 0.0011 | 0.929 | SWFDISNWLRYIR |

TABLE 4

HIV sequence segments over positions 671-683, from clades other than B or C, ranked by frequency of occurrence. The most common 100 such segments are shown. A total of 1637 HIV sequences from clades other than B or C were used for this analysis.

| Rank | %_of_seqs | cumulative_% | HIV_sequence_671-683 |
|---|---|---|---|
| 1 | 0.0844 | 0.0844 | NWFDITNWLWYIK |
| 2 | 0.0779 | 0.1623 | NWFDISNWLWYIK |
| 3 | 0.0593 | 0.2216 | NWFDITKWLWYIK |
| 4 | 0.0422 | 0.2638 | NWFSITKWLWYIK |
| 5 | 0.0406 | 0.3044 | NWFDISNWLWYIR |
| 6 | 0.0300 | 0.3344 | NWFDISKWLWYIK |
| 7 | 0.0284 | 0.3628 | NWLDITKWLWYIK |
| 8 | 0.0276 | 0.3904 | SWFDITNWLWYIK |
| 9 | 0.0260 | 0.4164 | NWFDITRWLWYIK |
| 10 | 0.0244 | 0.4408 | NWFNITNWLWYIK |
| 11 | 0.0219 | 0.4627 | SWFDISNWLWYIK |
| 12 | 0.0211 | 0.4838 | NWFSITNWLWYIK |
| 13 | 0.0203 | 0.5041 | TWFDISNWLWYIK |
| 14 | 0.0187 | 0.5228 | NWFNISNWLWYIK |
| 15 | 0.0179 | 0.5407 | NWFSITNWLWYIR |
| 16 | 0.0154 | 0.5561 | NWFDITNWLWYIR |
| 17 | 0.0154 | 0.5715 | NWFDISKWLWYIR |
| 18 | 0.0146 | 0.5861 | NWFDISRWLWYIK |
| 19 | 0.0138 | 0.5999 | SWFDISNWLWYIR |
| 20 | 0.0138 | 0.6137 | NWFDITSWLWYIK |
| 21 | 0.0122 | 0.6259 | TWFDITNWLWYIK |
| 22 | 0.0122 | 0.6381 | NWFSISNWLWYIK |
| 23 | 0.0114 | 0.6495 | TWFDISNWLWYIR |
| 24 | 0.0114 | 0.6609 | SWFSITNWLWYIK |
| 25 | 0.0106 | 0.6715 | NWFSITQWLWYIK |
| 26 | 0.0106 | 0.6821 | NWFSISNWLWYIR |
| 27 | 0.0089 | 0.691 | TWFDITKWLWYIK |
| 28 | 0.0089 | 0.6999 | SWFDITKWLWYIK |
| 29 | 0.0089 | 0.7088 | NWFNISNWLWYIR |
| 30 | 0.0081 | 0.7169 | NWFSISKWLWYIK |
| 31 | 0.0081 | 0.725 | NWFNITKWLWYIK |
| 32 | 0.0081 | 0.7331 | NWFDITQWLWYIK |
| 33 | 0.0081 | 0.7412 | NWFDITKWLWYIR |
| 34 | 0.0073 | 0.7485 | SWFDITNWLWYIR |
| 35 | 0.0073 | 0.7558 | NWFNITQWLWYIK |
| 36 | 0.0073 | 0.7631 | NWFGITKWLWYIK |

TABLE 4-continued

HIV sequence segments over positions 671-683, from clades other than B or C, ranked by frequency of occurrence. The most common 100 such segments are shown. A total of 1637 HIV sequences from clades other than B or C were used for this analysis.

| Rank | %_of_seqs | cumulative_% | HIV_sequence_671-683 |
|---|---|---|---|
| 37 | 0.0065 | 0.7696 | NWFDISHWLWYIK |
| 38 | 0.0057 | 0.7753 | SWFSITNWLWYIR |
| 39 | 0.0057 | 0.781 | SWFSISNWLWYIR |
| 40 | 0.0057 | 0.7867 | NWFNITNWLWYIR |
| 41 | 0.0049 | 0.7916 | NWFTITNWLWYIK |
| 42 | 0.0049 | 0.7965 | NWFGITNWLWYIK |
| 43 | 0.0049 | 0.8014 | NWFDISRWLWYIR |
| 44 | 0.0041 | 0.8055 | SWLDITKWLWYIK |
| 45 | 0.0041 | 0.8096 | SWFNITNWLWYIR |
| 46 | 0.0041 | 0.8137 | SWFNITNWLWYIK |
| 47 | 0.0041 | 0.8178 | SWFDITKWLWYIR |
| 48 | 0.0041 | 0.8219 | NWFEISKWLWYIK |
| 49 | 0.0041 | 0.826 | NWFDITSWLWYIR |
| 50 | 0.0032 | 0.8292 | SWFNISNWLWYIK |
| 51 | 0.0032 | 0.8324 | SWFDITRWLWYIK |
| 52 | 0.0032 | 0.8356 | SWFDISKWLWYIR |
| 53 | 0.0032 | 0.8388 | SWFDISKWLWYIK |
| 54 | 0.0032 | 0.842 | NWFNISKWLWYIK |
| 55 | 0.0024 | 0.8444 | TWFDITKWLWYIR |
| 56 | 0.0024 | 0.8468 | SWFSITKWLWYIK |
| 57 | 0.0024 | 0.8492 | SWFSISNWLWYIK |
| 58 | 0.0024 | 0.8516 | SWFNISNWLWYIR |
| 59 | 0.0024 | 0.854 | SWFEISNWLWYIR |
| 60 | 0.0024 | 0.8564 | SWFDITQWLWYIK |
| 61 | 0.0024 | 0.8588 | NWFSISQWLWYIK |
| 62 | 0.0024 | 0.8612 | NWFNISQWLWYIK |
| 63 | 0.0024 | 0.8636 | NWFGISNWLWYIK |
| 64 | 0.0024 | 0.866 | NWFEISNWLWYIK |
| 65 | 0.0024 | 0.8684 | NWFDISSWLWYIR |
| 66 | 0.0024 | 0.8708 | NWFDISSWLWYIK |
| 67 | 0.0016 | 0.8724 | TWFNISNWLWYIK |
| 68 | 0.0016 | 0.874 | TWFDITRWLWYIK |
| 69 | 0.0016 | 0.8756 | TWFDITQWLWYIK |
| 70 | 0.0016 | 0.8772 | TWFDITHWLWYIR |
| 71 | 0.0016 | 0.8788 | TWFDISHWLWYIK |
| 72 | 0.0016 | 0.8804 | SWFTITNWLWYIK |
| 73 | 0.0016 | 0.882 | SWFSISKWLWYIK |
| 74 | 0.0016 | 0.8836 | SWFNITQWLWYIK |
| 75 | 0.0016 | 0.8852 | SWFGITNWLWYIR |
| 76 | 0.0016 | 0.8868 | SWFDISSWLWYIR |
| 77 | 0.0016 | 0.8884 | SWFDISRWLWYIR |
| 78 | 0.0016 | 0.89 | NWFTITNWLWYIR |
| 79 | 0.0016 | 0.8916 | NWFSITRWLWYIK |
| 80 | 0.0016 | 0.8932 | NWFSITKWLWYIK |
| 81 | 0.0016 | 0.8948 | NWFSITHWLWYIK |
| 82 | 0.0016 | 0.8964 | NWFSISSWLWYIK |
| 83 | 0.0016 | 0.898 | NWFSISRWLWYIK |
| 84 | 0.0016 | 0.8996 | NWFNITSWLWYIK |
| 85 | 0.0016 | 0.9012 | NWFNISKWLWYIR |
| 86 | 0.0016 | 0.9028 | NWFDITQWLWYIR |
| 87 | 0.0016 | 0.9044 | NWFDITHWLWYIK |
| 88 | 0.0016 | 0.906 | NWFDISHWLWYIR |
| 89 | 0.0016 | 0.9076 | DWLDITKWLWYIK |
| 90 | 0.0016 | 0.9092 | DWFDITSWLWYIK |
| 91 | 0.0008 | 0.91 | XWFDISRWLWYIK |
| 92 | 0.0008 | 0.9108 | TWFSISNWLWYIR |
| 93 | 0.0008 | 0.9116 | TWFNITQWLWYIK |
| 94 | 0.0008 | 0.9124 | TWFGITNWLWYIR |
| 95 | 0.0008 | 0.9132 | TWFGISNWLWYIK |
| 96 | 0.0008 | 0.914 | TWFDLTNWLWYIK |
| 97 | 0.0008 | 0.9148 | TWFDLSNWLWYIK |
| 98 | 0.0008 | 0.9156 | TWFDITNWLWYIR |
| 99 | 0.0008 | 0.9164 | TWFDITHWLWYIK |
| 100 | 0.0008 | 0.9172 | TWFDISSWLWYIK |

TABLE 5

Position-specific frequencies of most common amino acids at HIV positions included in 10e8 scaffolds. Frequencies are shown for the minimal number of common amino acids for which the sum of frequencies is greater than 90%. Frequencies are shown computed over different sets of HIV sequences including: all_clades, clade_C, clade_B, and all clades other than B or C. Amino acids at these positions are exposed on the surface of 10e8 scaffolds.

| position | all_clades | clade_C | clade_B | not_B_or_C |
|---|---|---|---|---|
| 671 | N(0.72), S(0.21) | N(0.61), S(0.32) | N(0.78), S(0.17) | N(0.74), S(0.18) |
| 672 | W(0.997) | W(0.997) | W(0.997) | W(0.998) |
| 673 | F(0.976) | F(0.989) | F(0.999) | F(0.958) |
| 674 | D(0.59), S(0.22), N(0.13) | D(0.42), S(0.29), N(0.21) | D(0.64), S(0.21), N(0.1) | D(0.66), S(0.18), N(0.11) |
| 676 | T(0.65), S(0.34) | T(0.68), S(0.32) | T(0.73), S(0.27) | T(0.58), S(0.41) |
| 677 | N(0.57), K(0.27), Q(0.05), R(0.04) | N(0.60), K(0.29), Q(0.03), R(0.03) | N(0.59), K(0.24), Q(0.09), H(0.04), R(0.01) | N(0.55), K(0.28), Q(0.05), R(0.06) |
| 679 | L(0.997) | L(0.997) | L(0.992) | L(0.998) |
| 680 | W(0.989) | W(0.984) | W(0.987) | W(0.994) |
| 682 | I(0.996) | I(0.996) | I(0.996) | I(0.997) |
| 683 | K(0.78), R(0.21) | K(0.77), R(0.22) | K(0.82), R(0.17) | K(0.75), R(0.24) |

TABLE 6

Position-specific frequences of HIV amino acids in 3-mer and 5-mer cocktails of 10e8 scaffolds. The cocktails were designed to approximate the HIV frequencies of the most common amino acids at each epitope position for which the sum of individual frequencies is greater than 90%. Amino acids at these positions are exposed on the surface of 10e8 scaffolds.

| Position | 3mer_cocktail | 5mer_cocktail |
|---|---|---|
| 671 | N(0.67), S(0.33) | N(0.80), S(0.20) |
| 672 | W(1.0) | W(1.0) |
| 673 | F(1.0) | F(1.0) |
| 674 | D(0.33), S(0.33), N(0.33) | D(0.60), S(0.20), N(0.20) |
| 676 | T(0.67), S(0.33) | T(0.60), S(0.40) |
| 677 | N(0.67), K(0.33) | N(0.40), K(0.20), R(0.20), Q(0.20) |
| 679 | L(1.0) | L(1.0) |
| 680 | W(1.0) | W(1.0) |
| 682 | I(1.0) | I(1.0) |
| 683 | K(0.67), R(0.33) | K(0.80), R(0.20) |

TABLE 7

Theoretical coverage of position-specific HIV sequence variation over all clades by 3-mer and 5-mer scaffold cocktails. Here the coverage at each position is defined as the sum of the frequencies of the amino acids included in the cocktail at that position. The total coverage, defined as the product of the position-specific coverages, is listed at the bottom.

| | 3mer_cocktail | | 5mer_cocktail | |
|---|---|---|---|---|
| position | all_clades | clade_C | all_clades | clade_C |
| 671 | 0.93 | 0.93 | 0.93 | 0.93 |
| 672 | 1.00 | 1.00 | 1.00 | 1.00 |
| 673 | 0.98 | 0.99 | 0.98 | 0.99 |
| 674 | 0.94 | 0.92 | 0.94 | 0.95 |
| 676 | 0.99 | 1.00 | 0.99 | 1.00 |
| 677 | 0.84 | 0.89 | 0.93 | 0.95 |
| 679 | 1.00 | 1.00 | 1.00 | 1.00 |
| 680 | 0.99 | 0.98 | 0.99 | 0.98 |
| 682 | 1.00 | 1.00 | 1.00 | 1.00 |
| 683 | 0.99 | 0.99 | 0.99 | 0.99 |
| Total | 0.70 | 0.73 | 0.77 | 0.80 |

TABLE 8

Cocktails of three sequence strings (str1, str2, str3) in which each string represents a naturally occuring combination of HIV amino acids at HIV positions 671, 674, 676, 677, and 683, along with the frequency of occurrence (f1, f2, f3) of that combination in HIV sequences. The 71 cocktails listed are those that best approximate the HIV amino acid frequency distributions at those positions and that also provide optimal coverage of HIV sequence variation at each position, as discussed in the text.

| | str1 | str2 | str3 | f1 | f2 | f3 | f1 + f2 + f3 |
|---|---|---|---|---|---|---|---|
| 1 | NDTNK | NSTKK | SNSNR | 0.101 | 0.051 | 0.003 | 0.155 |
| 2 | NDTKK | NNTNK | SSSNR | 0.091 | 0.036 | 0.005 | 0.132 |
| 3 | NDTKK | NSTNK | SNSNR | 0.091 | 0.034 | 0.003 | 0.128 |
| 4 | NDTKK | NNSNK | SSTNR | 0.091 | 0.022 | 0.012 | 0.125 |
| 5 | NDSNK | NSTKK | SNTNR | 0.063 | 0.051 | 0.008 | 0.122 |
| 6 | NDTNK | NSTNR | SNSKK | 0.101 | 0.018 | 0.001 | 0.12 |
| 7 | NDTNK | SSTNK | NNSKR | 0.101 | 0.016 | 0.001 | 0.118 |
| 8 | NDTNK | SSTNR | NNSKK | 0.101 | 0.012 | 0.003 | 0.116 |
| 9 | NDTKK | NSTNK | SNSNK | 0.091 | 0.018 | 0.007 | 0.116 |
| 10 | NDTNK | SNTNR | NSSKK | 0.101 | 0.008 | 0.006 | 0.115 |
| 11 | NDTNK | NNTKK | SSSNR | 0.101 | 0.007 | 0.005 | 0.113 |
| 12 | NDTNK | NNSNR | SSTKK | 0.101 | 0.006 | 0.006 | 0.113 |
| 13 | NDTKK | SSTNK | NNSNR | 0.091 | 0.016 | 0.006 | 0.113 |
| 14 | NDTKK | NSSNK | SNTNR | 0.091 | 0.013 | 0.008 | 0.112 |
| 15 | NDTNK | NSSNR | SNTKK | 0.101 | 0.009 | 0.001 | 0.111 |
| 16 | NDTNK | SNTNK | NSSKR | 0.101 | 0.008 | 0.001 | 0.11 |
| 17 | NDTNK | SNSNK | NSTKR | 0.101 | 0.007 | 0.001 | 0.109 |
| 18 | NDTNK | NNTNR | SSSKK | 0.101 | 0.006 | 0.002 | 0.109 |
| 19 | NDTKK | NSSNR | SNTNK | 0.091 | 0.009 | 0.008 | 0.108 |
| 20 | NSTKK | NNTNK | SDSNR | 0.051 | 0.036 | 0.014 | 0.101 |
| 21 | NDTKK | NNTNR | SSSNK | 0.091 | 0.006 | 0.003 | 0.1 |
| 22 | NSTKK | SDTNK | NNSNR | 0.051 | 0.028 | 0.006 | 0.085 |
| 23 | NSTKK | NDSNR | SNTNK | 0.051 | 0.026 | 0.008 | 0.085 |
| 24 | NSTKK | NNSNK | SDTNR | 0.051 | 0.022 | 0.010 | 0.083 |
| 25 | NDSNK | NSTNR | SNTKK | 0.063 | 0.018 | 0.001 | 0.082 |
| 26 | NDSNK | SSTNR | NNTKK | 0.063 | 0.012 | 0.007 | 0.082 |
| 27 | NSTKK | SDSNK | NNTNR | 0.051 | 0.024 | 0.006 | 0.081 |
| 28 | NDSNK | NNTNR | SSTKK | 0.063 | 0.006 | 0.006 | 0.075 |
| 29 | NSTKK | NDTNR | SNSNK | 0.051 | 0.016 | 0.007 | 0.074 |
| 30 | NNTNK | NDSKK | SSTNR | 0.036 | 0.026 | 0.012 | 0.074 |
| 31 | NDSNK | SNTNK | NSTKR | 0.063 | 0.008 | 0.001 | 0.072 |
| 32 | NNTNK | NSTNK | SDSKR | 0.036 | 0.034 | 0.002 | 0.072 |
| 33 | NNTNK | NDSNR | SSTKK | 0.036 | 0.026 | 0.006 | 0.068 |
| 34 | NSTNK | NDSKK | SNTNR | 0.034 | 0.026 | 0.008 | 0.068 |
| 35 | NNTNK | SDTNK | NSSKR | 0.036 | 0.028 | 0.001 | 0.065 |
| 36 | NSTNK | SDTNK | NNSKR | 0.034 | 0.028 | 0.001 | 0.063 |
| 37 | NNTNK | SSTNK | NDSKR | 0.036 | 0.016 | 0.010 | 0.062 |
| 38 | NNTNK | SDSNK | NSTKR | 0.036 | 0.024 | 0.001 | 0.061 |
| 39 | NSTNK | NDSNR | SNTKK | 0.034 | 0.026 | 0.001 | 0.061 |
| 40 | NNTNK | NNSNK | SDTKR | 0.034 | 0.022 | 0.003 | 0.059 |
| 41 | NNTNK | SDTKK | NSSNR | 0.036 | 0.013 | 0.009 | 0.058 |
| 42 | NNTNK | NSTNR | SDSKK | 0.036 | 0.018 | 0.002 | 0.056 |

TABLE 8-continued

Cocktails of three sequence strings (str1, str2, str3) in which each string represents a naturally occuring combination of HIV amino acids at HIV positions 671, 674, 676, 677, and 683, along with the frequency of occurrence (f1, f2, f3) of that combination in HIV sequences. The 71 cocktails listed are those that best approximate the HIV amino acid frequency distributions at those positions and that also provide optimal coverage of HIV sequence variation at each position, as discussed in the text.

|    | str1 | str2 | str3 | f1 | f2 | f3 | f1 + f2 + f3 |
|----|------|------|------|------|------|------|------|
| 43 | NSTNK | SDSNR | NNTKK | 0.034 | 0.014 | 0.007 | 0.055 |
| 44 | NNTNK | NDTNR | SSSKK | 0.036 | 0.016 | 0.002 | 0.054 |
| 45 | NSTNK | SDTKK | NNSNR | 0.034 | 0.013 | 0.006 | 0.053 |
| 46 | NNSNK | NSTNR | SDTKK | 0.022 | 0.018 | 0.013 | 0.053 |
| 47 | NNTNK | NSSNK | SDTKR | 0.036 | 0.013 | 0.003 | 0.052 |
| 48 | NNTNK | SDTNR | NSSKK | 0.036 | 0.010 | 0.006 | 0.052 |
| 49 | NSTNK | NDSKR | SNTNK | 0.034 | 0.010 | 0.008 | 0.052 |
| 50 | NDSKK | NSTNR | SNTNK | 0.026 | 0.018 | 0.008 | 0.052 |
| 51 | NSTNK | NDTNR | SNSKK | 0.034 | 0.016 | 0.001 | 0.051 |
| 52 | SDTNK | NNSNK | NSTKR | 0.028 | 0.022 | 0.001 | 0.051 |
| 53 | SDTNK | NSTNR | NNSKK | 0.028 | 0.018 | 0.003 | 0.049 |
| 54 | NDSNR | SSTNK | NNTKK | 0.026 | 0.016 | 0.007 | 0.049 |
| 55 | SDSNK | NSTNR | NNTKK | 0.024 | 0.018 | 0.007 | 0.049 |
| 56 | NDSKK | SSTNK | NNTNR | 0.026 | 0.016 | 0.006 | 0.048 |
| 57 | NSTNK | SDTNR | NNSKK | 0.034 | 0.010 | 0.003 | 0.047 |
| 58 | NSTNK | SNSNK | NDTKR | 0.034 | 0.007 | 0.006 | 0.047 |
| 59 | NNTNK | NDTKR | SSSNK | 0.036 | 0.006 | 0.003 | 0.045 |
| 60 | SDTNK | NSSNR | NNTKK | 0.028 | 0.009 | 0.007 | 0.044 |
| 61 | NNSNK | NDTNR | SSTKK | 0.022 | 0.016 | 0.006 | 0.044 |
| 62 | NNSNK | SSTNK | NDTKR | 0.022 | 0.016 | 0.006 | 0.044 |
| 63 | NSTNK | NNTNR | SDSKK | 0.034 | 0.006 | 0.002 | 0.042 |
| 64 | SDTNK | NSSKK | NNTNR | 0.028 | 0.006 | 0.006 | 0.04 |
| 65 | SSTNK | NDTNR | NNSKK | 0.016 | 0.016 | 0.003 | 0.035 |
| 66 | NSSNK | SDTKK | NNTNR | 0.013 | 0.013 | 0.006 | 0.032 |
| 67 | NDTNR | NSSNK | SNTKK | 0.016 | 0.013 | 0.001 | 0.03 |
| 68 | NDTNR | SNTNK | NSSKK | 0.016 | 0.008 | 0.006 | 0.03 |
| 69 | NSSNK | SDTNR | NNTKK | 0.013 | 0.010 | 0.007 | 0.03 |
| 70 | NSSNK | SNTNK | NDTKR | 0.013 | 0.008 | 0.006 | 0.027 |
| 71 | NDTNR | NNTKK | SSSNK | 0.016 | 0.007 | 0.003 | 0.026 |

TABLE 9

T93v2RT12 and T117v2 oligomeric state and $K_D$s for mature and germline 10E8 and 4E10

| Scaffold | Expected Mw, kDa | Measured Mw, kDa | multimer state | $K_D$ 10E8 (pM) | $K_D$ 4E10 (pM) | $K_D$ GL-10E8 (μM) | $K_D$ GL-4E10 (pM) |
|---|---|---|---|---|---|---|---|
| T117v2 | 18.6 | 27.1 | mon/dim | 82 | 167.5 | ~6 | 187 |
| T117v2-2 | 18.6 | 18.1 | mon | $1.3 \times 10^3$ | 53.8 | | |
| T117v2-3 | 17.5 | 18.4 | mon | "~925 | 526 | ~8 | |
| T117v2-4 | 17.5 | 29.3 | mon/dim | 590 | $3.9 \times 10^3$ | 8 | $3.2 \times 10^3$ |
| T117v2-5 | 17.5 | 21.5 | mon/dim | 155 | | | |
| T117v2-1-P2 | 20.3 | 30.5/32.2 | mon/dim | 67 | | 3 | 540 |
| T117v2-2_P2 | 20.3 | 34.8 | mon/dim | 118 | 703 | | |
| T117v2-3_P2 | 20.3 | 24.7 | mostly mon | 600 | | | |
| T117v2-4_P2 | | | | | | | |
| T117v2-5_P2 | | | | | | | |
| T117v2-1_RSF1 | 18.9 | 34.2 | ~dim | 50 | ~100 | | ~100 |
| T117v2-1_g28_g91012 | 18.6 | 35.9 | dim | 180 | 490 | | 500 |
| T93v2RT12-1 | 14.9 | 15.4 | mon | 40 | 18 | 290-720 | |
| T93v2RT12-2 | 14.9 | 14.2 | mon | 20 | 14 | | |
| T93v2RT12-3 | 14.9 | 15.5 | mon | 110 | 580 | | |
| T93v2RT12-4 | 14.9 | 14.3 | mon | $2.7 \times 10^3$ | | | |
| T93v2RT12-5 | 14.9 | 13.6 | mon | 22 | | | |
| T93v2RT12-1-P2 | 16.5 | 15.1 | mon | 27 | | 290-730 | |
| T93v2RT12-2-P2 | 16.5 | 31 | dim | 430 | | 0.34-0.4 | |
| T93v2RT12-3-P2 | 16.5 | 15.7/14.9 | mon | 130 | | | |
| T93v2RT12-4-P2 | 16.5 | 32.3 | dim | | | | |
| T93v2RT12-5-P2 | 16.5 | 28.1 | ~dim | | | | | from all clades, the most common sequence variant occurs at a frequency of only 10%. A similar situation exists if considering only sequences within clade C (Table 2), within clade B (Table 3), or within sequences from clades other than B or C (Table 4). Hence immunization with an immunogen presenting only that sequence might induce reactivity only to 10% or less of HIV strains. Position specific amino acid frequencies are given in Table 5 for the fewest number of most common amino acids at each position for which the sum of the frequencies is greater than 90%.

Figure 2:
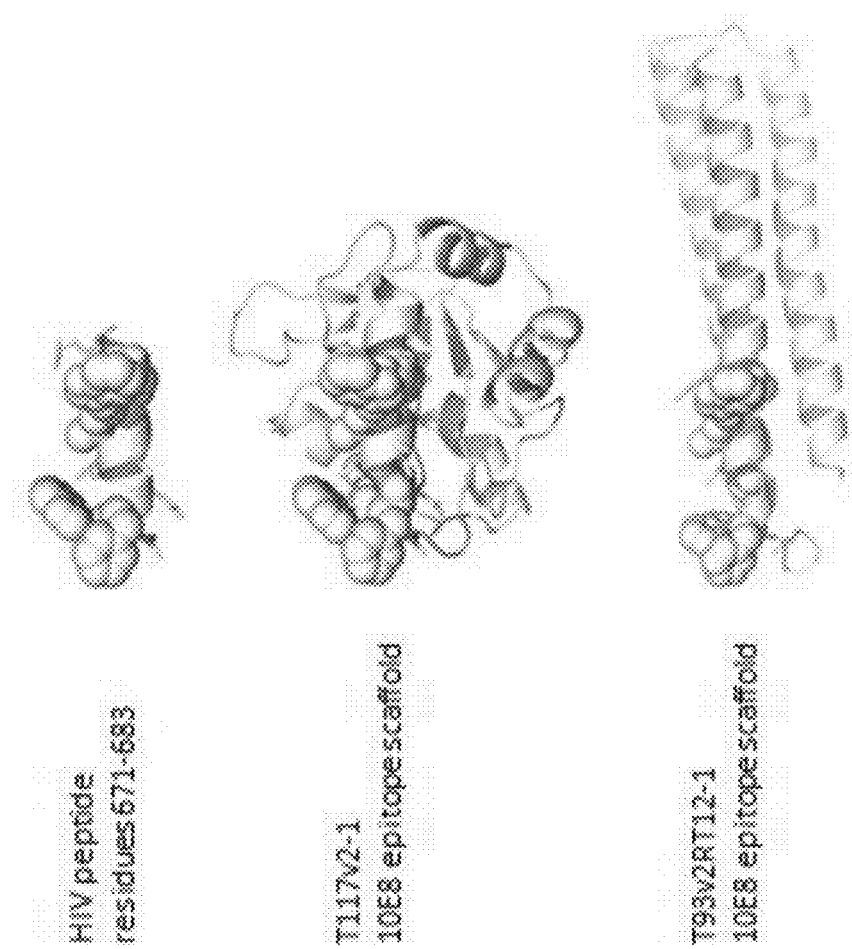
FIG. 2 depicts models for the T93v2RT12-1 and T117v2-1 scaffolds in comparison to the 10E8 epitope peptide spanning HIV residues 671-683.
Figure 3A:
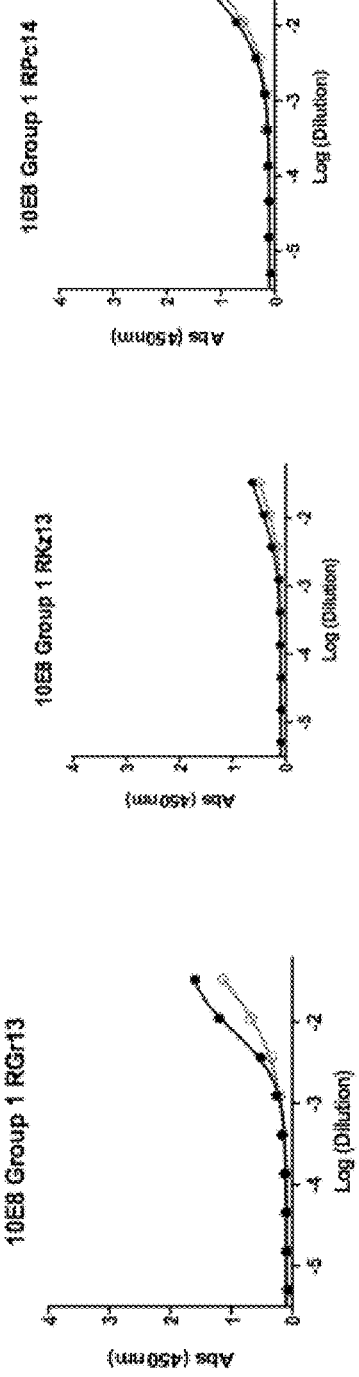
FIGS. 3A and 3B depicts ELISA data indicating 10E8 epitope-specific responses in NHPs, from heterologous prime-boost. Sera from 2 weeks post-immunization 3 by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.
Figure 3A:
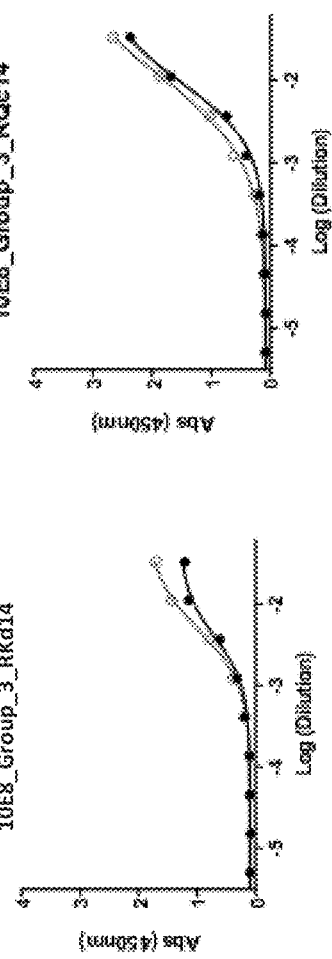
Figure 3B:
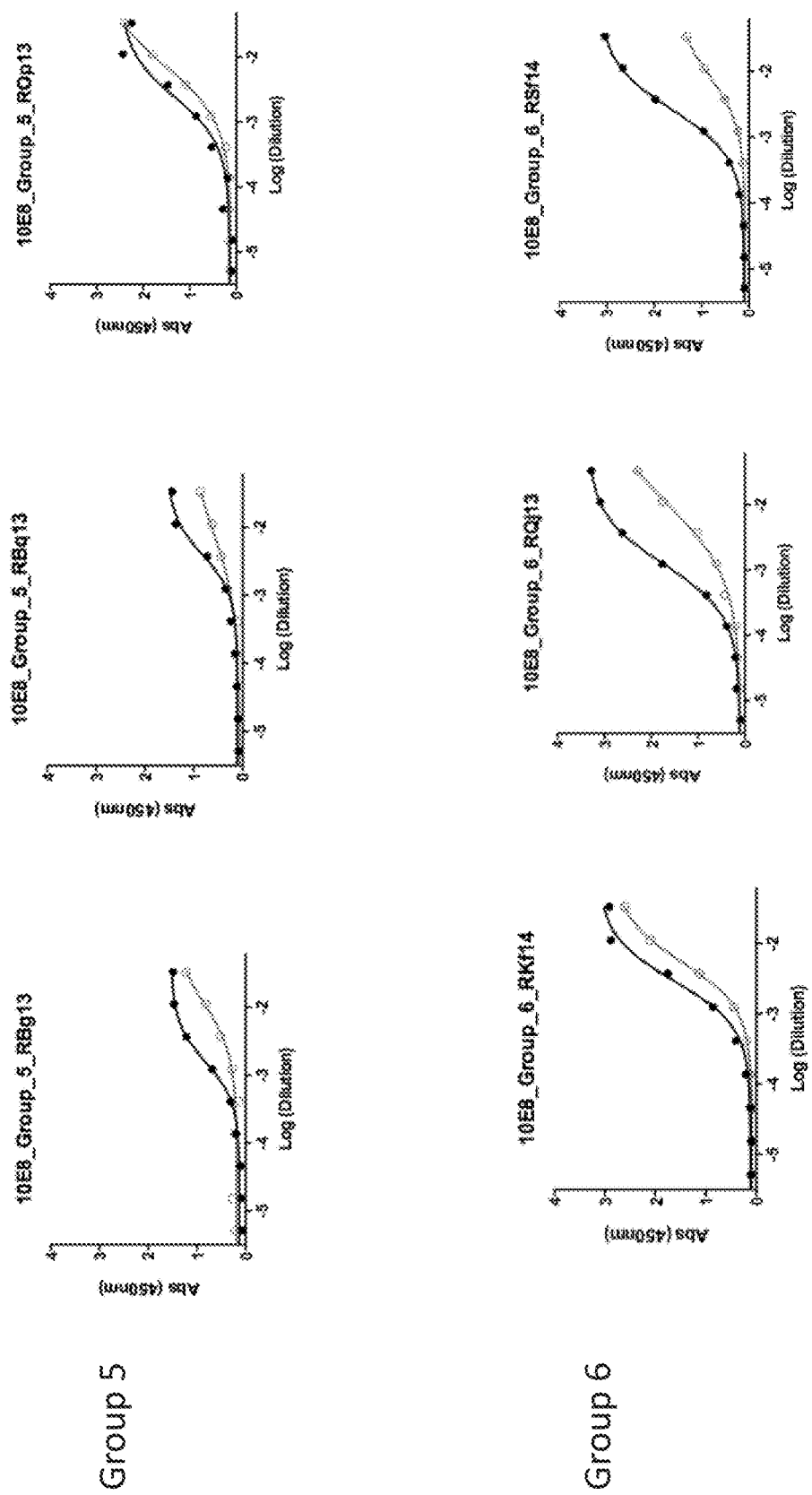

FIG. 2 shows models for the T93v2RT12-1 and T117v2-1 scaffolds in comparison to the 10E8 epitope peptide spanning HIV residues 671-683. HIV amino acids that either interact directly with 10e8 or that are exposed around the 10e8 contact positions are shown in spacefill or stick representation. Those residues in spacefill are highly conserved in HIV (>99%), while residues in stick are more variable.

To induce antibodies that can recognize the diversity of HIV sequences within the 10e8 epitope, Applicants devised variants of the T93v2RT12 and T117v2 scaffolds that contain different variants of the epitope. The sequences of these variants are listed below, with the 10e8 epitope residues in bold. In each case an additional his-tag (LEHHHHHH) (SEQ ID NO: 200) was present at the C-terminus for purification. All of these variants have been expressed in *E. coli* and purified, and the resulting proteins show high affinity for the 10E8 antibody as measured by surface plasmon resonance. The T117v2 variants also have modest affinity for a predicted germline precursor to 10E8 (referred to simply as "germline 10E8"). Oligomeric state and dissociation constants for 10E8, germline 10E8, as well as the antibody 4E10 and germline 4E10, are given in Table 9. (Regarding the epitope residues, Applicants note that, in the case of T93v2RT12, a valine residue (V) has been employed in place of an Isoleucine residue (I) at the epitope position corresponding to HIV position 682. Val only differs from Ile by a single methyl group, and Val at this position is able to the same contacts to 10e8 as Ile-Val CG1 making van der Tables 1, 2, 3, 4, and 5 document the HIV sequence variation at the positions in and around the 10e8 contact residues. As shown in Table 1, considering HIV sequences waals interactions with 10e8 heavy chain residue Phe100A. However, the Val could be changed to Ile.)

10E8_T93v2RT12-1
GKADEVREKARRRMEQAVEEFKRRLRQFEEKVKQKEPRDDEINRWIDIVK

KKADEAKKRVEEVGDQAADEAAQLGNDPNVNWFDITNVLWDVKKLTEKAI

NDIDDALKKMKDWLESG

10E8_T93v2RT12-2
GKADEVREKARRRMEQAVEEFKRRLRQFEEKVKQKEPRDDEINRWIDIVK

KKADEAKKRVEEVGDQAADEAAQLGNDPNVNWFSITKVLWDVKKLTEKAI

NDIDDALKKNIKDWLESG

10E8_T93v2RT12-3
GKADEVREKARRRMEQAVEEFKRRLRQFEEKVKQKEPRDDEINRWIDIVK

KKADEAKKRVEEVGDQAADEAAQLGNDPNVSWFNISNVLWDVRKLTEKAI

NDIDDALKKMKDWLESG

10E8_T93v2RT12-4
GKADEVREKARRRMEQAVEEFKRRLRQFEEKVKQKEPRDDEINRWIDIVK

KKADEAKKRVEEVGDQAADEAAQLGNDPNVNWFDISRVLWDVKKLTEKAI

NDIDDALKKMKDWLESG

10E8_T93v2RT12-5
GKADEVREKARRRMEQAVEEFKRRLRQFEEKVKQKEPRDDEINRWIDIVK

KKADEAKKRVEEVGDQAADEAAQLGNDPNVNWFDITQVLWDVKKLTEKAI

NDIDDALKKMKDWLESG

10E8_T117v2-1
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITNVLWWIKAVIQDEDFMQQLLVMNDDEIYQSIY

TRISELEHHHHHH

10E8_T117v2-2
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFSITKVLWW IKAVIQDEDFMQQLLVMNDDEIYQSIY

TRISE

10E8_T117v2-3
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGSWFNISNVLWW IRAVIQDEDFMQQLLVMNDDEIYQSIY

TRISE

10E8_T117v2-4
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDISRVLWW IKAVIQDEDFMQQLLVMNDDEIYQSIY

TRISE

10E8_T117v2-5
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

-continued

VPVRVVFMLALGNWFDITQVLWW IKAVIQDEDFMQQLLVMNDDEIYQSIY

TRISE

The above scaffold variants are intended to be used as a 3-member sequence or cocktail that includes variants-1, -2, and -3, or a 5-member sequence or cocktail that includes variants-1, -2, -3, -4, and -5. Applicants will refer to these as the "3-mer scaffold cocktail" or "5-mer scaffold cocktail". One example of a way to employ these variants would be to prime with a 3-mer scaffold cocktail composed of 10E8_T117v2, 10E8_T117v2-2, and 10E8_T117v2-3, and then boost with a 3-mer scaffold cocktail composed of 10E8_T93v2RT12-1, 10E8_T93v2RT12-2, and 10E8_T93v2RT12-3.

The 3-mer and 5-mer scaffold cocktails were designed to include specific epitope variants so that the cocktails would: (1) approximate the natural HIV amino acid frequency distribution of the most common amino acids at each epitope position for which the sum of the frequencies is greater than 90%, (2) maximize the theoretical coverage of sequence variation at each position and (3) include the most frequently occurring natural epitope variants possible. Here Applicants illustrate that these design goals were met.

First, the different epitope variants included in the 3-mer and 5-mer scaffold cocktails were chosen so that the cocktails would approximate the natural HIV amino acid frequency distribution of the most common amino acids at each epitope position. The natural HIV frequency distributions are shown in Table 4. The frequency distributions within the 3-mer and 5-mer cocktails are given in Table 5. The mimicry of frequency distributions by the cocktails is quite good—for example at position 671 the 3-mer cocktail includes asparagine (N) and serine (S) at frequencies of 0.67 and 0.33, respectively, while the natural distribution computed over all clades has N and S at 0.72 and 0.21, respectively. Indeed, computing the root mean square deviation (RMSD) between the natural HIV frequency distributions and the distributions in the cocktails shows that the frequency RMSDs are 0.03 (computed over all clades), 0.02 (clade C), 0.03 (clade B), and 0.03 (all clades other than B or C). (Applicants note that this RMSD calculation only includes contributions from amino acids that are included in the cocktail; it does not include the minor contributions from amino acids that are absent from the cocktail (frequency in cocktail=0) but that are present at low frequency in natural HIV sequences. As such, this RMSD is an slight underestimate.)

Second, the epitope variants included in the 3-mer and 5-mer scaffold cocktails were also specifically chosen to maximize the theoretical coverage of sequence variation at each position. Table 6 shows the theoretical coverage at each position, and one can see that the coverage is quite high, ranging from 84% measured over all clades at position 677, to 100% over all clades at several positions. Indeed, the lowest coverage over all clades is 84% for the 3-mer cocktail and 93% for the 5-mer cocktail. The total coverage, calculated as the product of the coverages at each position and also shown in Table 6, is 70% over all clades for the 3-mer cocktail, and 77% over clade C for the 3-mer cocktail. The total coverage for the 5-mer cocktail is 73% over all clades and 80% over clade C.

Based on the above two criteria (frequency distribution and coverage), Applicants identified 71 3-mer cocktails of epitope variants that were optimal and equivalent based on having a minimal frequency RMSD of 0.03 and a maximal coverage of 66% over all clades. These 71 3-mer cocktails are shown in Table 8. Any of these 3-mer cocktails could suffice to induce broadly-cross-reactive antibodies, and Applicants therefore contemplate the use of any of these cocktails as deployed on the 10e8 scaffolds. However, Applicants further selected a single cocktail from those 71, based on Applicants' third criteria that a cocktail should employ the most frequently occurring natural variants possible. From that third criteria, Applicants selected the first cocktail listed in Table 8 as the most promising candidate, because that cocktail both included the single most frequent variant and had the highest sum of frequencies of individual epitope variants. Based on that cocktail, Applicants designed the 5mer cocktail to further improve both the overall mimicry of amino acid frequencies and the total coverage of sequence variation.

Applicants note that it may prove important to immunize with multiple 3-mer or 5-mer cocktails to obtain an optimal response. Therefore Applicants contemplate the use of any of the 71 3-mer cocktails as displayed on 10E8 scaffolds, as well as appropriately designed 5-mer cocktails based on those 3-mers. Furthermore, the 3-mer and 5-mer cocktails that described for T93v2RT12 and T117v2 may also be implemented on the glycan-masked T117v2.

When different scaffolds are employed in sequential immunization regimens, it may be important to append an exogenous CD4 T helper peptide to each scaffold, to ensure that both prime and boost contain at least one conserved T help epitope. As an example of this, Applicants have appended the tetanus toxin P2 peptide to each of the above scaffolds. The P2 peptide has been reported to be a "universal" T helper peptide that can be presented on diverse human MEW alleles. Below, a histag and linker "HHHH-HHGG" (SEQ ID NO: 211) before the P2 tag (QYIKAN-SKFIGITEL) (SEQ ID NO: 212) and the present invention contemplates both the presence and absence of the histag and linker as well as other universal T helper epitopes to be fused to the C-terminal besides a P2 tag. With the P2 helper peptide appended, the sequences of the scaffolds were:

```
10E8_T93v2RT12-1_P2
GKADEVREKARRRMEQAVEEFKRRLRQFEEKVKQKEPRDDEINRWIDIVK

KKADEAKKRVEEVGDQAADEAAQLGNDPNVNWFDITNVLWDVKKLTEKAI

NDIDDALKKMKDWLESGGHHHHHHGGQYIKANSKFIGITEL

10E8_T93v2RT12-2_P2
GKADEVREKARRRMEQAVEEFKRRLRQFEEKVKQKEPRDDEINRWIDIVK

KKADEAKKRVEEVGDQAADEAAQLGNDPNVNWFSITKVLWDVKKLTEKAI

NDIDDALKKNIKDWLESGGHHHHHHGGQYIKANSKFIGITEL

10E8_T93v2RT12-3_P2
GKADEVREKARRRMEQAVEEFKRRLRQFEEKVKQKEPRDDEINRWIDIVK

KKADEAKKRVEEVGDQAADEAAQLGNDPNVSWFNISNVLWDVRKLTEKAI

NDIDDALKKMKDWLESGGHHHHHHGGQYIKANSKFIGITEL

10E8_T93v2RT12-4_P2
GKADEVREKARRRMEQAVEEFKRRLRQFEEKVKQKEPRDDEINRWIDIVK

KKADEAKKRVEEVGDQAADEAAQLGNDPNVNWFDISRVLWDVKKLTEKAI

NDIDDALKKMKDWLESGGHHHHHHGGQYIKANSKFIGITEL

10E8_T93v2RT12-5_P2
GKADEVREKARRRMEQAVEEFKRRLRQFEEKVKQKEPRDDEINRWIDIVK

KKADEAKKRVEEVGDQAADEAAQLGNDPNVNWFDITQVLWDVKKLTEKAI

NDIDDALKKMKDWLESGGHHHHHHGGQYIKANSKFIGITEL

10E8_T117v2-1_P2
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITNVLWWIKAVIQDEDFMQQLLVMNDDEIYQSIY

TRISEGGHHHHHHGGQYIKANSKFIGITEL

10E8_T117v2-2_P2
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFSITKVLWWIKAVIQDEDFMQQLLVMNDDEIYQSIY

TRISEGGHHHHHHGGQYIKANSKFIGITEL

10E8_T117v2-3_P2
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGSWFNISNVLWWIRAVIQDEDFMQQLLVMNDDEIYQSIY

TRISEGGHHHHHHGGQYIKANSKFIGITEL

10E8_T117v2-4_P2
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDISRVLWWIKAVIQDEDFMQQLLVMNDDEIYQSIY

TRISEGGHHHHHHGGQYIKANSKFIGITEL

10E8_T117v2-5_P2
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITQVLWWIKAVIQDEDFMQQLLVMNDDEIYQSIY

TRISEGGHHHHHHGGQYIKANSKFIGITEL
```

Applicants note that these P2 variants also included a his-tag (HHHHHH) (SEQ ID NO: 223) for purification but that is not required.

An additional scaffold (10E8_T117v2-1_RSF1), antigenically distinct from the T93v2, T93v2RT12 and T117v2 scaffolds, was designed by resurfacing T117v2. This scaffold also has high affinity for 10E8 antibody. This new scaffold is useful for assessing epitope-specific responses induced by the other scaffolds, and this new scaffold may also be useful as an immunogen alone or used in sequential heterologous immunization regimens with other scaffolds. The new scaffold can be expressed with the same epitope cocktail as discussed above.

```
10E8_T117v2-1_RSF1
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

VPVRVVFMLALGNWFDITNVLWWIKAVIQDDEFMKRLLYMTDDKIYESIR

KRIYDLE

10E8_T117v2-2_RSF1
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP
```

```
VPVRVVFMLALGNWFSITKVLWWIKAVIQDDEFMKRLLYMTDDKIYESIR
KRIYD

10E8_T117v2-3_RSF1
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

VPVRVVFMLALGSWFNISNVLWWIRAVIQDDEFMKRLLYMTDDKIYESIR
KRIYD

10E8_T117v2-4_RSF1
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

VPVRVVFMLALGNWFDISRVLWWIKAVIQDDEFMKRLLYMTDDKIYESIR
KRIYD

10E8_T117v2-5_RSF1
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

VPVRVVFMLALGNWFDITQVLWWIKAVIQDDEFMKRLLYMTDDKIYESIR
KRIYD
```

The T117v2 scaffold was also modified by glycan-masking, in which N-linked glycosylation sites were added at surface-exposed positions outside the 10E8 epitope. This may be helpful to focus immune responses onto the epitope, by reducing responses to glycosylated areas. The glycans may also focus the angle of approach of antibodies against the epitope. Several constructs were designed and tested. The two constructs with the highest degree of glycosylation that retained high affinity for 10E8 and 4E10 antibodies were 10E8_T117v2-1_g28_g91012 and 10E8_T117v2-1_g258_g91012. The additional glycosylation sites are noted in bold.

```
10E8_T117v2-1_g28_g91012
NAMQGIHFRRHYVRHLPKNVSQNDIIKALASPLINDGMVVSDFADHVITR

ENNSPTGLPVEPVGVAIPHTDSKYVNQSAISVGILAEPVNFEDANGTPDP

VPVRVVFMLALGNWFDITNVLWWIKAVIQDEDFMQQLLNMSDDEIYQSIY
TRISE

10E8_T117v2-1_g258_g91012
NAMQGIHFRRHYVRHLPKNVSQNDIIKALASPLINDGMVVSDFADHVITR

ENNSPTGLPVEPVGVAIPHTDSKYVNQSAISVGILAEPVNFEDANGTPDP

VPVRVVFMLALGNWFDITNVLWWIKAVIQNASFMQQLLNMSDDEIYQSIY
TRISE
```

These scaffolds are novel immunogens to induce epitope-specific responses against the conformational 10E8 epitope, especially when employed in heterologous prime-boost immunization regimens. Six groups of rhesus macaques (3 macaques per group) were immunized by the intramuscular route with Iscomatrix adjuvant, either at 0, 1, 3 months (groups 1, 2, 3, 4) or with a prime at 0, 1 month followed by a heterologous boost at 3 months (groups 5 and 6). The groups included the following immunogens: T93v2RT12-1 (group 1), T117v2-1 (group 2), T93v2RT12-1, -2, and -3 (group 3), T117v2-1_P2, T117v2-2_P2, and T117v2-3_P2 (group 4), T93v2RT12-1_P2, T93v2RT12-2_P2, and T93v2RT12-3_P2 at 0, 1 month and T117v2-1_P2, T117v2-2_P2, and T117v2-3_P2 at 3 months (group 5), T117v2-1_P2, T117v2-2_P2, and T117v2-3_P2 at 0, 1 months and T93v2RT12-1_P2, T93v2RT12-2_P2, and T93v2RT12-3_P2 at 3 months (group 6). To assay for epitope-specific responses, Applicants tested animal plasma for binding to the resurfaced T117v2 (10E8_T117v2-1_RSF1) as well as an epitope-knockout mutant that has 1000-fold reduced affinity for 10E8 (10E8_T117v2-1_RSF1_KO3, $K_D$ for 10E8 is 50 nM compared to 50 pM for 10E8_T117v2-1_RSF1). Plasma from all animals taken at day 0 showed no reactivity to either 10E8_T117v2-1_RSF1 or 10E8_T117v2-1_RSF1_KO3 (not shown). For groups 1-4 that received homologous immunization regimens that repeat the same antigen or antigens, plasma taken 2 weeks after the third immunization showed similar reactivity to both 10E8_T117v2-1_RSF1 and 10E8_T117v2-1_RSF1_KO3. Therefore there was no evidence for epitope-specific responses in those groups. However, for groups 5 and 6 that received heterologous prime-boost immunizations, plasma taken 2 weeks after the third immunization showed appreciable epitope-specific reactivity indicated by higher ELISA binding to 10E8_T117v2-1_RSF1 compared to 10E8_T117v2-1_RSF1_KO3. Group 6 had the largest epitope-specific responses.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies of the present invention may be used in accordance with the present invention. In certain embodiments, the antibodies of the present invention may be used in vitro (such as using cell-free expression systems) and/or in cultured cells grown in vitro in order to produce the encoded HIV-antibodies which may then be used for various applications such as in the production of proteinaceous vaccines. For such applications, any vector that allows expression of the antibodies in vitro and/or in cultured cells may be used.

For applications where it is desired that the antibodies be expressed in vivo, for example when the transgenes of the invention are used in DNA or DNA-containing vaccines, any vector that allows for the expression of the antibodies of the present invention and is safe for use in vivo may be used. In preferred embodiments the vectors used are safe for use in humans, mammals and/or laboratory animals.

For the antibodies of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the antibodies of the invention can be expressed.

For example, when the aim is to express the antibodies of the invention in vitro, or in cultured cells, or in any prokaryotic or eukaryotic system for the purpose of producing the protein(s) encoded by that antibody, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies under the identified circumstances.

In an advantageous embodiment, IgG1 expression vectors may be utilized to reconstitute heavy and light chain constant regions if heavy and light chain genes of the antibodies of the present invention are cloned.

When the aim is to express the antibodies of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if the aim is to express the HIV-1 antigens in cells in order to produce and isolate the expressed proteins, such as from cells grown in culture. For expressing the antibodies in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies can be carried out in any suitable type of host cells, such as bacterial cells, yeast, insect cells, and mammalian cells. The antibodies of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. In preferred embodiments the subject is a human, for example a human that is infected with, or is at risk of infection with, HIV-1.

The term "pharmaceutical composition" is used herein to define a solid or liquid composition in a form, concentration and level of purity suitable for administration to a patient (e.g. a human patient) upon which administration it can elicit the desired physiological changes. The terms "immunogenic composition" and "immunological composition" and "immunogenic or immunological composition" cover any composition that elicits an immune response against the targeted pathogen, HIV. Terms such as "vaccinal composition" and "vaccine" and "vaccine composition" cover any composition that induces a protective immune response against the targeted pathogen or which efficaciously protects against the pathogen; for instance, after administration or injection, elicits a protective immune response against the targeted pathogen or provides efficacious protection against the pathogen. Accordingly, an immunogenic or immunological composition induces an immune response which can, but need not, be a protective immune response. An immunogenic or immunological composition can be used in the treatment of individuals infected with the pathogen, e.g., to stimulate an immune response against the pathogen, such as by stimulating antibodies against the pathogen. Thus, an immunogenic or immunological composition can be a pharmaceutical composition. Furthermore, when the text speaks of "immunogen, antigen or epitope", an immunogen can be an antigen or an epitope of an antigen. A diagnostic composition is a composition containing a compound or antibody, e.g., a labeled compound or antibody, that is used for detecting the presence in a sample, such as a biological sample, e.g., blood, semen, vaginal fluid, etc, of an antibody that binds to the compound or an immunogen, antigen or epitope that binds to the antibody; for instance, an anti-HIV antibody or an HIV immunogen, antigen or epitope.

For such in vivo applications the nucleotide sequences, antibodies of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies of the invention to a subject, such as a human, such that the antibodies are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylenepolyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO4)2, AlNa (SO4)2, AlNH(SO4)2, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention in the immunogenic composition of the invention can be readily determined by those of skill in the art. For example, the dosage of the antibodies can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably which may comprise an adenovirus vector containing DNA encoding one or more of the antibodies of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

The immunogenic compositions of the invention can be administered alone, or can be co-administered, or sequentially administered, with other therapeutic agents, thereby providing multivalent or "cocktail" or combination compositions of the invention and methods of employing them. The therapeutic agent can be an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

<160> NUMBER OF SEQ ID NOS: 243

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

His His His His His His Gly Ser Ile Ser Asp Ile Arg Lys Asp Ala
1               5                   10                  15

Glu Val Arg Met Asp Lys Ala Val Glu Ala Phe Lys Asn Lys Leu Asp
            20                  25                  30

Lys Phe Lys Ala Ala Val Arg Lys Val Phe Pro Thr Glu Glu Arg Ile
        35                  40                  45

Lys Asp Trp Leu Lys Ile Val Arg Gly Glu Ala Glu Gln Ala Arg Val
    50                  55                  60

Ala Val Arg Asn Val Gly Arg Asp Ala Asn Asp Lys Ala Ala Ala Leu
65                  70                  75                  80

Gly Lys Asp Lys Glu Ile Asn Trp Phe Asp Ile Ser Gln Ser Leu Trp
                85                  90                  95

Asp Val Gln Lys Leu Thr Asp Ala Ala Ile Lys Lys Ile Glu Ala Ala
            100                 105                 110

Leu Ala Asp Met Glu Ala Trp Leu Thr Gln Gly
        115                 120

<210> SEQ ID NO 2
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Glu Ala Gln Arg Val Arg Gln Glu Ala Lys Glu Arg Met Lys Arg
1               5                   10                  15

Ala Val Glu Lys Phe Lys Lys Gly Leu Lys Glu Phe Asn Thr Glu Val
            20                  25                  30

Glu Lys Lys Glu Pro Arg Gln Gln Arg Ile Gln Lys Trp Glu Gln Ile
        35                  40                  45

Val Glu Glu Arg Ala Lys Lys Ala Glu Asp Glu Val Lys Lys Val Gly
    50                  55                  60

Lys Glu Ala Asn Asp Arg Ala Ala Lys Leu Gly Gln Asp Pro Gln Val
65                  70                  75                  80

Asn Trp Phe Asp Ile Ser Gln Ile Leu Trp Asp Val Gln Lys Leu Thr
                85                  90                  95

Gln Glu Ala Ile Glu Glu Ile Arg Lys Ala Leu Glu Gln Met Arg Arg
            100                 105                 110

Trp Leu Gln Arg Gly Leu Glu His His His His His
        115                 120                 125

<210> SEQ ID NO 3
<211> LENGTH: 125
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 3

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
            20                  25                  30

Lys Gln Lys Glu Pro Arg Asp Asp Glu Ile Asn Arg Trp Ile Asp Ile
        35                  40                  45

Val Lys Lys Lys Ala Asp Glu Ala Lys Lys Arg Val Glu Glu Val Gly
    50                  55                  60

Asp Gln Ala Asn Asp Glu Ala Ala Gln Leu Gly Asn Asp Pro Asn Val
65                  70                  75                  80

Asn Trp Phe Asp Ile Ser Gln Val Leu Trp Asp Val Gln Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly Leu Glu His His His His His
        115                 120                 125

<210> SEQ ID NO 4
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His His His His His His Asn Ala Met Gln Gly Ile His Phe Arg Arg
1               5                   10                  15

His Tyr Val Arg His Leu Pro Lys Glu Val Ser Gln Asn Asp Ile Ile
            20                  25                  30

Lys Ala Leu Ala Ser Pro Leu Ile Asn Asp Gly Met Val Val Ser Asp
        35                  40                  45

Phe Ala Asp His Val Ile Thr Arg Glu Gln Asn Phe Pro Thr Gly Leu
    50                  55                  60

Pro Val Glu Pro Val Gly Val Ala Ile Pro His Thr Asp Ser Lys Tyr
65                  70                  75                  80

Val Arg Gln Asn Ala Ile Ser Val Gly Ile Leu Ala Glu Pro Val Asn
                85                  90                  95

Phe Glu Asp Ala Gly Gly Glu Pro Asp Pro Val Pro Arg Val Val
            100                 105                 110

Phe Met Leu Ala Leu Gly Asn Trp Phe Asp Ile Thr Asn Val Leu Trp
        115                 120                 125

Trp Ile Met Asp Val Ile Gln Asp Glu Asp Phe Met Gln Gln Leu Leu
    130                 135                 140

Val Met Asn Asp Asp Glu Ile Tyr Gln Ser Ile Tyr Thr Arg Ile Ser
145                 150                 155                 160

Glu

<210> SEQ ID NO 5
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 5

Gly His His His His His Gly Ser Glu Val Ser Gln Asn Asp Ile
1               5                   10                  15

Ile Lys Ala Leu Ala Ser Pro Leu Ile Asn Asp Gly Met Val Val Ser
            20                  25                  30

Asp Phe Ala Asp His Val Ile Thr Arg Glu Gln Asn Ala Pro Thr Gly
        35                  40                  45

Leu Pro Val Glu Pro Val Gly Val Ala Ile Pro His Thr Asp Ser Lys
    50                  55                  60

Tyr Val Arg Gln Asn Ala Ile Ser Val Gly Ile Leu Ala Glu Pro Val
65                  70                  75                  80

Asn Phe Glu Asp Ala Gly Gly Glu Pro Asp Pro Val Pro Val Arg Val
                85                  90                  95

Val Phe Met Leu Ala Leu Gly Asn Trp Phe Asp Ile Thr Asn Val Leu
            100                 105                 110

Trp Trp Ile Met Asp Val Ile Gln Asp Ala Asp Phe Met Gln Gln Leu
        115                 120                 125

Leu Val Met Asn Asp Asp Glu Ile Tyr Gln Ser Ile Tyr Thr Arg Ile
    130                 135                 140

Ser Glu Ala Ala Gly Met Ala Gly Ile His Phe Arg Arg His Tyr Val
145                 150                 155                 160

Arg His Leu Pro Leu Glu His His His His His
                165                 170

<210> SEQ ID NO 6
<211> LENGTH: 165
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 6

Gly Ser Glu Val Ser Gln Asn Asp Ile Ile Lys Ala Leu Ala Ser Pro
1               5                   10                  15

Leu Ile Asn Asp Gly Met Val Val Ser Asp Phe Ala Asp His Val Ile
            20                  25                  30

Thr Arg Glu Gln Asn Ala Pro Thr Gly Leu Pro Val Glu Pro Val Gly
        35                  40                  45

Val Ala Ile Pro His Thr Asp Ser Lys Tyr Val Arg Gln Asn Ala Ile
    50                  55                  60

Ser Val Gly Ile Leu Ala Glu Pro Val Asn Phe Glu Asp Ala Gly Gly
65                  70                  75                  80

Glu Pro Asp Pro Val Pro Val Arg Val Val Phe Met Leu Ala Leu Gly
                85                  90                  95

Asn Trp Phe Asp Ile Thr Asn Val Leu Trp Trp Ile Lys Ala Val Ile
            100                 105                 110

Gln Asp Ala Asp Phe Met Gln Gln Leu Leu Arg Met Asn Asp Asp Glu
        115                 120                 125

Ile Tyr Gln Ser Ile Tyr Thr Arg Ile Ser Glu Ala Ala Gly Met Ala
    130                 135                 140

Gly Ile His Phe Arg Arg His Tyr Val Arg His Leu Gly Leu Glu His
145                 150                 155                 160

His His His His His
                165

```
<210> SEQ ID NO 7
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Asp Ile Thr Asn Val Leu Trp Trp Ile Lys Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu Leu Glu His His His
145                 150                 155                 160

His His His

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Arg Asp Ala Asn Asp Lys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Arg Asp Ala Ala Asp Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 10

Leu Trp Asp Val Gln Lys Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 11

Leu Trp Asp Val Lys Lys Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 12

Gly Lys Glu Ala Asn Asp Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 13

Gly Lys Glu Ala Ala Asp Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 14

Gly Asp Gln Ala Asn Asp Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 15

Gly Asp Gln Ala Ala Asp Glu
1               5

<210> SEQ ID NO 16
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Trp Trp Ile Met Asp Val Ile Gln
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Trp Trp Ile Lys Ala Val Ile Gln
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln Leu Leu Val Met Asn Asp
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gln Leu Leu Arg Met Asn Asp
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Trp Trp Ile Met Asp Val Ile
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21
```

```
Leu Trp Trp Ile Lys Ala Val Ile
1               5
```

<210> SEQ ID NO 22
<211> LENGTH: 13
<212> TYPE: PRT
<213> ORGANISM: Human immunodeficiency virus

<400> SEQUENCE: 22

```
Asn Trp Phe Asp Ile Thr Asn Trp Leu Trp Tyr Ile Lys
1               5                   10
```

<210> SEQ ID NO 23
<211> LENGTH: 13
<212> TYPE: PRT
<213> ORGANISM: Human immunodeficiency virus

<400> SEQUENCE: 23

```
Asn Trp Phe Asp Ile Thr Lys Trp Leu Trp Tyr Ile Lys
1               5                   10
```

<210> SEQ ID NO 24
<211> LENGTH: 13
<212> TYPE: PRT
<213> ORGANISM: Human immunodeficiency virus

<400> SEQUENCE: 24

```
Asn Trp Phe Asp Ile Ser Asn Trp Leu Trp Tyr Ile Lys
1               5                   10
```

<210> SEQ ID NO 25
<211> LENGTH: 13
<212> TYPE: PRT
<213> ORGANISM: Human immunodeficiency virus

<400> SEQUENCE: 25

```
Asn Trp Phe Ser Ile Thr Lys Trp Leu Trp Tyr Ile Lys
1               5                   10
```

<210> SEQ ID NO 26
<211> LENGTH: 13
<212> TYPE: PRT
<213> ORGANISM: Human immunodeficiency virus

<400> SEQUENCE: 26

```
Asn Trp Phe Asn Ile Thr Asn Trp Leu Trp Tyr Ile Lys
1               5                   10
```

<210> SEQ ID NO 27
<211> LENGTH: 13
<212> TYPE: PRT
<213> ORGANISM: Human immunodeficiency virus

<400> SEQUENCE: 27

```
Asn Trp Phe Ser Ile Thr Asn Trp Leu Trp Tyr Ile Lys
1               5                   10
```

<210> SEQ ID NO 28
<211> LENGTH: 13
<212> TYPE: PRT
<213> ORGANISM: Human immunodeficiency virus

<400> SEQUENCE: 28

```
Ser Trp Phe Asp Ile Thr Asn Trp Leu Trp Tyr Ile Lys
1               5                   10
```

```
<210> SEQ ID NO 29
<211> LENGTH: 13
<212> TYPE: PRT
<213> ORGANISM: Human immunodeficiency virus

<400> SEQUENCE: 29

Asn Trp Phe Asp Ile Ser Asn Trp Leu Trp Tyr Ile Arg
1               5                   10

<210> SEQ ID NO 30
<211> LENGTH: 13
<212> TYPE: PRT
<213> ORGANISM: Human immunodeficiency virus

<400> SEQUENCE: 30

Asn Trp Phe Asp Ile Ser Lys Trp Leu Trp Tyr Ile Lys
1               5                   10

<210> SEQ ID NO 31
<211> LENGTH: 13
<212> TYPE: PRT
<213> ORGANISM: Human immunodeficiency virus

<400> SEQUENCE: 31

Ser Trp Phe Asp Ile Ser Asn Trp Leu Trp Tyr Ile Lys
1               5                   10

<210> SEQ ID NO 32
<211> LENGTH: 13
<212> TYPE: PRT
<213> ORGANISM: Human immunodeficiency virus

<400> SEQUENCE: 32

Asn Trp Phe Asn Ile Ser Asn Trp Leu Trp Tyr Ile Lys
1               5                   10

<210> SEQ ID NO 33
<211> LENGTH: 13
<212> TYPE: PRT
<213> ORGANISM: Human immunodeficiency virus

<400> SEQUENCE: 33

Asn Trp Phe Ser Ile Thr Asn Trp Leu Trp Tyr Ile Arg
1               5                   10

<210> SEQ ID NO 34
<211> LENGTH: 13
<212> TYPE: PRT
<213> ORGANISM: Human immunodeficiency virus

<400> SEQUENCE: 34

Asn Trp Phe Asp Ile Thr Asn Trp Leu Trp Tyr Ile Arg
1               5                   10

<210> SEQ ID NO 35
<211> LENGTH: 13
<212> TYPE: PRT
<213> ORGANISM: Human immunodeficiency virus

<400> SEQUENCE: 35

Ser Trp Phe Ser Ile Thr Asn Trp Leu Trp Tyr Ile Lys
1               5                   10
```

```
<210> SEQ ID NO 36
<211> LENGTH: 13
<212> TYPE: PRT
<213> ORGANISM: Human immunodeficiency virus

<400> SEQUENCE: 36

Asn Trp Phe Asp Ile Thr Arg Trp Leu Trp Tyr Ile Lys
1               5                   10

<210> SEQ ID NO 37
<211> LENGTH: 13
<212> TYPE: PRT
<213> ORGANISM: Human immunodeficiency virus

<400> SEQUENCE: 37

Ser Trp Phe Asp Ile Ser Asn Trp Leu Trp Tyr Ile Arg
1               5                   10

<210> SEQ ID NO 38
<211> LENGTH: 13
<212> TYPE: PRT
<213> ORGANISM: Human immunodeficiency virus

<400> SEQUENCE: 38

Asn Trp Phe Ser Ile Ser Asn Trp Leu Trp Tyr Ile Lys
1               5                   10

<210> SEQ ID NO 39
<211> LENGTH: 13
<212> TYPE: PRT
<213> ORGANISM: Human immunodeficiency virus

<400> SEQUENCE: 39

Thr Trp Phe Asp Ile Thr Asn Trp Leu Trp Tyr Ile Lys
1               5                   10

<210> SEQ ID NO 40
<211> LENGTH: 13
<212> TYPE: PRT
<213> ORGANISM: Human immunodeficiency virus

<400> SEQUENCE: 40

Thr Trp Phe Asp Ile Ser Asn Trp Leu Trp Tyr Ile Lys
1               5                   10

<210> SEQ ID NO 41
<211> LENGTH: 13
<212> TYPE: PRT
<213> ORGANISM: Human immunodeficiency virus

<400> SEQUENCE: 41

Asn Trp Leu Asp Ile Thr Lys Trp Leu Trp Tyr Ile Lys
1               5                   10

<210> SEQ ID NO 42
<211> LENGTH: 13
<212> TYPE: PRT
<213> ORGANISM: Human immunodeficiency virus

<400> SEQUENCE: 42

Asn Trp Phe Asp Ile Thr Ser Trp Leu Trp Tyr Ile Lys
1               5                   10

<210> SEQ ID NO 43
<211> LENGTH: 13
```

<212> TYPE: PRT
<213> ORGANISM: Human immunodeficiency virus

<400> SEQUENCE: 43

Asn Trp Phe Asp Ile Thr Gln Trp Leu Trp Tyr Ile Lys
1 5 10

<210> SEQ ID NO 44
<211> LENGTH: 13
<212> TYPE: PRT
<213> ORGANISM: Human immunodeficiency virus

<400> SEQUENCE: 44

Ser Trp Phe Ser Ile Thr Asn Trp Leu Trp Tyr Ile Arg
1 5 10

<210> SEQ ID NO 45
<211> LENGTH: 13
<212> TYPE: PRT
<213> ORGANISM: Human immunodeficiency virus

<400> SEQUENCE: 45

Ser Trp Phe Asp Ile Thr Lys Trp Leu Trp Tyr Ile Lys
1 5 10

<210> SEQ ID NO 46
<211> LENGTH: 13
<212> TYPE: PRT
<213> ORGANISM: Human immunodeficiency virus

<400> SEQUENCE: 46

Ser Trp Phe Asp Ile Thr Asn Trp Leu Trp Tyr Ile Arg
1 5 10

<210> SEQ ID NO 47
<211> LENGTH: 13
<212> TYPE: PRT
<213> ORGANISM: Human immunodeficiency virus

<400> SEQUENCE: 47

Asn Trp Phe Asp Ile Ser Lys Trp Leu Trp Tyr Ile Arg
1 5 10

<210> SEQ ID NO 48
<211> LENGTH: 13
<212> TYPE: PRT
<213> ORGANISM: Human immunodeficiency virus

<400> SEQUENCE: 48

Asn Trp Phe Asn Ile Thr Gln Trp Leu Trp Tyr Ile Lys
1 5 10

<210> SEQ ID NO 49
<211> LENGTH: 13
<212> TYPE: PRT
<213> ORGANISM: Human immunodeficiency virus

<400> SEQUENCE: 49

Asn Trp Phe Ser Ile Ser Asn Trp Leu Trp Tyr Ile Arg
1 5 10

<210> SEQ ID NO 50
<211> LENGTH: 13
<212> TYPE: PRT
<213> ORGANISM: Human immunodeficiency virus

<400> SEQUENCE: 50

Asn Trp Phe Gly Ile Thr Lys Trp Leu Trp Tyr Ile Lys
1               5                   10

<210> SEQ ID NO 51
<211> LENGTH: 13
<212> TYPE: PRT
<213> ORGANISM: Human immunodeficiency virus

<400> SEQUENCE: 51

Asn Trp Phe Ser Ile Thr Gln Trp Leu Trp Tyr Ile Lys
1               5                   10

<210> SEQ ID NO 52
<211> LENGTH: 13
<212> TYPE: PRT
<213> ORGANISM: Human immunodeficiency virus

<400> SEQUENCE: 52

Asn Trp Phe Asp Ile Ser Arg Trp Leu Trp Tyr Ile Lys
1               5                   10

<210> SEQ ID NO 53
<211> LENGTH: 13
<212> TYPE: PRT
<213> ORGANISM: Human immunodeficiency virus

<400> SEQUENCE: 53

Ser Trp Phe Asn Ile Thr Asn Trp Leu Trp Tyr Ile Arg
1               5                   10

<210> SEQ ID NO 54
<211> LENGTH: 13
<212> TYPE: PRT
<213> ORGANISM: Human immunodeficiency virus

<400> SEQUENCE: 54

Thr Trp Phe Asp Ile Ser Asn Trp Leu Trp Tyr Ile Arg
1               5                   10

<210> SEQ ID NO 55
<211> LENGTH: 13
<212> TYPE: PRT
<213> ORGANISM: Human immunodeficiency virus

<400> SEQUENCE: 55

Asn Trp Phe Asn Ile Thr Lys Trp Leu Trp Tyr Ile Lys
1               5                   10

<210> SEQ ID NO 56
<211> LENGTH: 13
<212> TYPE: PRT
<213> ORGANISM: Human immunodeficiency virus

<400> SEQUENCE: 56

Thr Trp Phe Asp Ile Thr Lys Trp Leu Trp Tyr Ile Lys
1               5                   10

<210> SEQ ID NO 57
<211> LENGTH: 13
<212> TYPE: PRT
<213> ORGANISM: Human immunodeficiency virus

<400> SEQUENCE: 57

Ser Phe Asn Ile Thr Asn Trp Leu Trp Tyr Ile Lys
1               5                   10

<210> SEQ ID NO 58
<211> LENGTH: 13
<212> TYPE: PRT
<213> ORGANISM: Human immunodeficiency virus

<400> SEQUENCE: 58

Ser Trp Phe Asn Ile Ser Asn Trp Leu Trp Tyr Ile Lys
1               5                   10

<210> SEQ ID NO 59
<211> LENGTH: 13
<212> TYPE: PRT
<213> ORGANISM: Human immunodeficiency virus

<400> SEQUENCE: 59

Asn Trp Phe Asn Ile Ser Asn Trp Leu Trp Tyr Ile Arg
1               5                   10

<210> SEQ ID NO 60
<211> LENGTH: 13
<212> TYPE: PRT
<213> ORGANISM: Human immunodeficiency virus

<400> SEQUENCE: 60

Asn Trp Phe Ser Ile Ser Lys Trp Leu Trp Tyr Ile Lys
1               5                   10

<210> SEQ ID NO 61
<211> LENGTH: 13
<212> TYPE: PRT
<213> ORGANISM: Human immunodeficiency virus

<400> SEQUENCE: 61

Asn Trp Phe Asn Ile Thr Asn Trp Leu Trp Tyr Ile Arg
1               5                   10

<210> SEQ ID NO 62
<211> LENGTH: 13
<212> TYPE: PRT
<213> ORGANISM: Human immunodeficiency virus

<400> SEQUENCE: 62

Asn Trp Phe Asp Ile Thr Lys Trp Leu Trp Tyr Ile Arg
1               5                   10

<210> SEQ ID NO 63
<211> LENGTH: 13
<212> TYPE: PRT
<213> ORGANISM: Human immunodeficiency virus

<400> SEQUENCE: 63

Ser Trp Phe Ser Ile Thr Lys Trp Leu Trp Tyr Ile Lys
1               5                   10

<210> SEQ ID NO 64
<211> LENGTH: 13
<212> TYPE: PRT
<213> ORGANISM: Human immunodeficiency virus

<400> SEQUENCE: 64

Asn Trp Phe Thr Ile Thr Asn Trp Leu Trp Tyr Ile Lys

```
<210> SEQ ID NO 65
<211> LENGTH: 13
<212> TYPE: PRT
<213> ORGANISM: Human immunodeficiency virus

<400> SEQUENCE: 65

Ser Trp Phe Ser Ile Ser Asn Trp Leu Trp Tyr Ile Arg
1               5                   10

<210> SEQ ID NO 66
<211> LENGTH: 13
<212> TYPE: PRT
<213> ORGANISM: Human immunodeficiency virus

<400> SEQUENCE: 66

Asn Trp Phe Asp Ile Thr His Trp Leu Trp Tyr Ile Lys
1               5                   10

<210> SEQ ID NO 67
<211> LENGTH: 13
<212> TYPE: PRT
<213> ORGANISM: Human immunodeficiency virus

<400> SEQUENCE: 67

Ser Trp Phe Asp Ile Thr Gln Trp Leu Trp Tyr Ile Lys
1               5                   10

<210> SEQ ID NO 68
<211> LENGTH: 13
<212> TYPE: PRT
<213> ORGANISM: Human immunodeficiency virus

<400> SEQUENCE: 68

Asn Trp Phe Ser Ile Thr His Trp Leu Trp Tyr Ile Lys
1               5                   10

<210> SEQ ID NO 69
<211> LENGTH: 13
<212> TYPE: PRT
<213> ORGANISM: Human immunodeficiency virus

<400> SEQUENCE: 69

Thr Trp Phe Asp Ile Thr Asn Trp Leu Trp Tyr Ile Arg
1               5                   10

<210> SEQ ID NO 70
<211> LENGTH: 13
<212> TYPE: PRT
<213> ORGANISM: Human immunodeficiency virus

<400> SEQUENCE: 70

Ser Trp Phe Asn Ile Ser Asn Trp Leu Trp Tyr Ile Arg
1               5                   10

<210> SEQ ID NO 71
<211> LENGTH: 13
<212> TYPE: PRT
<213> ORGANISM: Human immunodeficiency virus

<400> SEQUENCE: 71

Ser Trp Phe Asp Ile Thr Lys Trp Leu Trp Tyr Ile Arg
1               5                   10
```

```
<210> SEQ ID NO 72
<211> LENGTH: 13
<212> TYPE: PRT
<213> ORGANISM: Human immunodeficiency virus

<400> SEQUENCE: 72

Asn Trp Phe Gly Ile Thr Asn Trp Leu Trp Tyr Ile Lys
1               5                   10

<210> SEQ ID NO 73
<211> LENGTH: 13
<212> TYPE: PRT
<213> ORGANISM: Human immunodeficiency virus

<400> SEQUENCE: 73

Asn Trp Phe Asp Ile Ser Arg Trp Leu Trp Tyr Ile Arg
1               5                   10

<210> SEQ ID NO 74
<211> LENGTH: 13
<212> TYPE: PRT
<213> ORGANISM: Human immunodeficiency virus

<400> SEQUENCE: 74

Asn Trp Phe Asp Ile Ser His Trp Leu Trp Tyr Ile Lys
1               5                   10

<210> SEQ ID NO 75
<211> LENGTH: 13
<212> TYPE: PRT
<213> ORGANISM: Human immunodeficiency virus

<400> SEQUENCE: 75

Asn Trp Phe Asn Ile Ser Lys Trp Leu Trp Tyr Ile Lys
1               5                   10

<210> SEQ ID NO 76
<211> LENGTH: 13
<212> TYPE: PRT
<213> ORGANISM: Human immunodeficiency virus

<400> SEQUENCE: 76

Asn Trp Phe Asp Ile Thr Gln Trp Leu Trp Tyr Ile Arg
1               5                   10

<210> SEQ ID NO 77
<211> LENGTH: 13
<212> TYPE: PRT
<213> ORGANISM: Human immunodeficiency virus

<400> SEQUENCE: 77

Ser Trp Phe Ser Ile Ser Asn Trp Leu Trp Tyr Ile Lys
1               5                   10

<210> SEQ ID NO 78
<211> LENGTH: 13
<212> TYPE: PRT
<213> ORGANISM: Human immunodeficiency virus

<400> SEQUENCE: 78

Ser Trp Phe Ser Ile Ser Lys Trp Leu Trp Tyr Ile Lys
1               5                   10

<210> SEQ ID NO 79
```

```
<211> LENGTH: 13
<212> TYPE: PRT
<213> ORGANISM: Human immunodeficiency virus

<400> SEQUENCE: 79

Asn Trp Phe Asp Ile Ser Ser Trp Leu Trp Tyr Ile Lys
1               5                   10

<210> SEQ ID NO 80
<211> LENGTH: 13
<212> TYPE: PRT
<213> ORGANISM: Human immunodeficiency virus

<400> SEQUENCE: 80

Ser Trp Leu Asp Ile Thr Lys Trp Leu Trp Tyr Ile Lys
1               5                   10

<210> SEQ ID NO 81
<211> LENGTH: 13
<212> TYPE: PRT
<213> ORGANISM: Human immunodeficiency virus

<400> SEQUENCE: 81

Ser Trp Phe Ser Ile Thr Gln Trp Leu Trp Tyr Ile Lys
1               5                   10

<210> SEQ ID NO 82
<211> LENGTH: 13
<212> TYPE: PRT
<213> ORGANISM: Human immunodeficiency virus

<400> SEQUENCE: 82

Ser Trp Phe Asp Ile Ser Lys Trp Leu Trp Tyr Ile Arg
1               5                   10

<210> SEQ ID NO 83
<211> LENGTH: 13
<212> TYPE: PRT
<213> ORGANISM: Human immunodeficiency virus

<400> SEQUENCE: 83

Ser Trp Phe Asp Ile Ser Lys Trp Leu Trp Tyr Ile Lys
1               5                   10

<210> SEQ ID NO 84
<211> LENGTH: 13
<212> TYPE: PRT
<213> ORGANISM: Human immunodeficiency virus

<400> SEQUENCE: 84

Asn Trp Phe Ser Ile Ser Gln Trp Leu Trp Tyr Ile Lys
1               5                   10

<210> SEQ ID NO 85
<211> LENGTH: 13
<212> TYPE: PRT
<213> ORGANISM: Human immunodeficiency virus

<400> SEQUENCE: 85

Asn Trp Phe Glu Ile Ser Asn Trp Leu Trp Tyr Ile Lys
1               5                   10

<210> SEQ ID NO 86
<211> LENGTH: 13
<212> TYPE: PRT
```

<213> ORGANISM: Human immunodeficiency virus

<400> SEQUENCE: 86

Asn Trp Phe Asp Ile Thr Ser Trp Leu Trp Tyr Ile Arg
1               5                   10

<210> SEQ ID NO 87
<211> LENGTH: 13
<212> TYPE: PRT
<213> ORGANISM: Human immunodeficiency virus

<400> SEQUENCE: 87

Ser Trp Phe Asp Ile Thr Arg Trp Leu Trp Tyr Ile Lys
1               5                   10

<210> SEQ ID NO 88
<211> LENGTH: 13
<212> TYPE: PRT
<213> ORGANISM: Human immunodeficiency virus

<400> SEQUENCE: 88

Asn Trp Phe Thr Ile Ser Asn Trp Leu Trp Tyr Ile Lys
1               5                   10

<210> SEQ ID NO 89
<211> LENGTH: 13
<212> TYPE: PRT
<213> ORGANISM: Human immunodeficiency virus

<400> SEQUENCE: 89

Asn Trp Phe Glu Ile Ser Lys Trp Leu Trp Tyr Ile Lys
1               5                   10

<210> SEQ ID NO 90
<211> LENGTH: 13
<212> TYPE: PRT
<213> ORGANISM: Human immunodeficiency virus

<400> SEQUENCE: 90

Asn Trp Phe Asp Ile Ser Gln Trp Leu Trp Tyr Ile Lys
1               5                   10

<210> SEQ ID NO 91
<211> LENGTH: 13
<212> TYPE: PRT
<213> ORGANISM: Human immunodeficiency virus

<400> SEQUENCE: 91

Thr Trp Phe Gly Ile Thr Asn Trp Leu Trp Tyr Ile Arg
1               5                   10

<210> SEQ ID NO 92
<211> LENGTH: 13
<212> TYPE: PRT
<213> ORGANISM: Human immunodeficiency virus

<400> SEQUENCE: 92

Thr Trp Phe Asp Ile Thr Lys Trp Leu Trp Tyr Ile Arg
1               5                   10

<210> SEQ ID NO 93
<211> LENGTH: 13
<212> TYPE: PRT
<213> ORGANISM: Human immunodeficiency virus

<400> SEQUENCE: 93

Ser Trp Phe Thr Ile Thr Asn Trp Leu Trp Tyr Ile Lys
1               5                   10

<210> SEQ ID NO 94
<211> LENGTH: 13
<212> TYPE: PRT
<213> ORGANISM: Human immunodeficiency virus

<400> SEQUENCE: 94

Ser Trp Phe Asp Ile Ser Ser Trp Leu Trp Tyr Ile Arg
1               5                   10

<210> SEQ ID NO 95
<211> LENGTH: 13
<212> TYPE: PRT
<213> ORGANISM: Human immunodeficiency virus

<400> SEQUENCE: 95

Ser Trp Phe Asp Ile Ser Arg Trp Leu Trp Tyr Ile Lys
1               5                   10

<210> SEQ ID NO 96
<211> LENGTH: 13
<212> TYPE: PRT
<213> ORGANISM: Human immunodeficiency virus

<400> SEQUENCE: 96

Asn Trp Phe Ser Ile Thr Lys Trp Leu Trp Tyr Ile Arg
1               5                   10

<210> SEQ ID NO 97
<211> LENGTH: 13
<212> TYPE: PRT
<213> ORGANISM: Human immunodeficiency virus

<400> SEQUENCE: 97

Asn Trp Phe Asn Ile Thr His Trp Leu Trp Tyr Ile Lys
1               5                   10

<210> SEQ ID NO 98
<211> LENGTH: 13
<212> TYPE: PRT
<213> ORGANISM: Human immunodeficiency virus

<400> SEQUENCE: 98

Asn Trp Phe Gly Ile Ser Asn Trp Leu Trp Tyr Ile Lys
1               5                   10

<210> SEQ ID NO 99
<211> LENGTH: 13
<212> TYPE: PRT
<213> ORGANISM: Human immunodeficiency virus

<400> SEQUENCE: 99

Asn Trp Phe Asp Ile Ser Ser Trp Leu Trp Tyr Ile Arg
1               5                   10

<210> SEQ ID NO 100
<211> LENGTH: 13
<212> TYPE: PRT
<213> ORGANISM: Human immunodeficiency virus

<400> SEQUENCE: 100

Thr Trp Phe Asn Ile Ser Asn Trp Leu Trp Tyr Ile Lys
1               5                   10

<210> SEQ ID NO 101
<211> LENGTH: 13
<212> TYPE: PRT
<213> ORGANISM: Human immunodeficiency virus

<400> SEQUENCE: 101

Thr Trp Phe Asp Ile Thr Arg Trp Leu Trp Tyr Ile Lys
1               5                   10

<210> SEQ ID NO 102
<211> LENGTH: 13
<212> TYPE: PRT
<213> ORGANISM: Human immunodeficiency virus

<400> SEQUENCE: 102

Thr Trp Phe Asp Ile Thr Gln Trp Leu Trp Tyr Ile Lys
1               5                   10

<210> SEQ ID NO 103
<211> LENGTH: 13
<212> TYPE: PRT
<213> ORGANISM: Human immunodeficiency virus

<400> SEQUENCE: 103

Thr Trp Phe Asp Ile Ser His Trp Leu Trp Tyr Ile Lys
1               5                   10

<210> SEQ ID NO 104
<211> LENGTH: 13
<212> TYPE: PRT
<213> ORGANISM: Human immunodeficiency virus

<400> SEQUENCE: 104

Ser Trp Phe Ser Ile Thr Gln Trp Leu Trp Tyr Ile Arg
1               5                   10

<210> SEQ ID NO 105
<211> LENGTH: 13
<212> TYPE: PRT
<213> ORGANISM: Human immunodeficiency virus

<400> SEQUENCE: 105

Ser Trp Phe Ser Ile Thr His Trp Leu Trp Tyr Ile Lys
1               5                   10

<210> SEQ ID NO 106
<211> LENGTH: 13
<212> TYPE: PRT
<213> ORGANISM: Human immunodeficiency virus

<400> SEQUENCE: 106

Ser Trp Phe Ser Ile Ser Gln Trp Leu Trp Tyr Ile Lys
1               5                   10

<210> SEQ ID NO 107
<211> LENGTH: 13
<212> TYPE: PRT
<213> ORGANISM: Human immunodeficiency virus

<400> SEQUENCE: 107

Ser Trp Phe Asn Ile Thr Gln Trp Leu Trp Tyr Ile Lys
1               5                   10

<210> SEQ ID NO 108
<211> LENGTH: 13
<212> TYPE: PRT
<213> ORGANISM: Human immunodeficiency virus

<400> SEQUENCE: 108

Ser Trp Phe Asn Ile Thr His Trp Leu Trp Tyr Ile Lys
1               5                   10

<210> SEQ ID NO 109
<211> LENGTH: 13
<212> TYPE: PRT
<213> ORGANISM: Human immunodeficiency virus

<400> SEQUENCE: 109

Ser Trp Phe Glu Ile Thr Asn Trp Leu Trp Tyr Ile Lys
1               5                   10

<210> SEQ ID NO 110
<211> LENGTH: 13
<212> TYPE: PRT
<213> ORGANISM: Human immunodeficiency virus

<400> SEQUENCE: 110

Ser Trp Phe Glu Ile Ser Asn Trp Leu Trp Tyr Ile Arg
1               5                   10

<210> SEQ ID NO 111
<211> LENGTH: 13
<212> TYPE: PRT
<213> ORGANISM: Human immunodeficiency virus

<400> SEQUENCE: 111

Ser Trp Phe Asp Ile Thr Ser Trp Leu Trp Tyr Ile Arg
1               5                   10

<210> SEQ ID NO 112
<211> LENGTH: 13
<212> TYPE: PRT
<213> ORGANISM: Human immunodeficiency virus

<400> SEQUENCE: 112

Ser Trp Phe Asp Ile Ser Gln Trp Leu Trp Tyr Ile Lys
1               5                   10

<210> SEQ ID NO 113
<211> LENGTH: 13
<212> TYPE: PRT
<213> ORGANISM: Human immunodeficiency virus
<220> FEATURE:
<221> NAME/KEY: MOD_RES
<222> LOCATION: (4)..(4)
<223> OTHER INFORMATION: Any amino acid

<400> SEQUENCE: 113

Asn Trp Phe Xaa Ile Thr Asn Trp Leu Trp Tyr Ile Lys
1               5                   10

<210> SEQ ID NO 114
<211> LENGTH: 13
<212> TYPE: PRT
<213> ORGANISM: Human immunodeficiency virus

<400> SEQUENCE: 114

Asn Trp Phe Ser Ile Thr Ser Trp Leu Trp Tyr Ile Lys
1               5                   10

<210> SEQ ID NO 115
<211> LENGTH: 13
<212> TYPE: PRT
<213> ORGANISM: Human immunodeficiency virus

<400> SEQUENCE: 115

Asn Trp Phe Ser Ile Thr Arg Trp Leu Trp Tyr Ile Lys
1               5                   10

<210> SEQ ID NO 116
<211> LENGTH: 13
<212> TYPE: PRT
<213> ORGANISM: Human immunodeficiency virus

<400> SEQUENCE: 116

Asn Trp Phe Ser Ile Thr Lys Trp Leu Arg Tyr Ile Gln
1               5                   10

<210> SEQ ID NO 117
<211> LENGTH: 13
<212> TYPE: PRT
<213> ORGANISM: Human immunodeficiency virus

<400> SEQUENCE: 117

Asn Trp Phe Ser Ile Thr His Trp Leu Trp Tyr Ile Arg
1               5                   10

<210> SEQ ID NO 118
<211> LENGTH: 13
<212> TYPE: PRT
<213> ORGANISM: Human immunodeficiency virus

<400> SEQUENCE: 118

Asn Trp Phe Ser Ile Ser Arg Trp Leu Trp Tyr Ile Lys
1               5                   10

<210> SEQ ID NO 119
<211> LENGTH: 13
<212> TYPE: PRT
<213> ORGANISM: Human immunodeficiency virus

<400> SEQUENCE: 119

Asn Trp Phe Asn Ile Thr Arg Trp Leu Trp Tyr Ile Lys
1               5                   10

<210> SEQ ID NO 120
<211> LENGTH: 13
<212> TYPE: PRT
<213> ORGANISM: Human immunodeficiency virus

<400> SEQUENCE: 120

Asn Trp Phe Asn Ile Thr Glu Trp Leu Trp Tyr Ile Lys
1               5                   10

<210> SEQ ID NO 121
<211> LENGTH: 13
<212> TYPE: PRT
<213> ORGANISM: Human immunodeficiency virus

<400> SEQUENCE: 121

Asn Trp Phe Asn Ile Ser Gln Trp Leu Trp Tyr Ile Lys
1               5                   10

```
<210> SEQ ID NO 122
<211> LENGTH: 13
<212> TYPE: PRT
<213> ORGANISM: Human immunodeficiency virus

<400> SEQUENCE: 122

Asp Trp Phe Asn Ile Ser Asn Trp Leu Trp Tyr Ile Lys
1               5                   10

<210> SEQ ID NO 123
<211> LENGTH: 13
<212> TYPE: PRT
<213> ORGANISM: Human immunodeficiency virus

<400> SEQUENCE: 123

Thr Trp Phe Gly Ile Thr Asn Trp Leu Trp Tyr Ile Lys
1               5                   10

<210> SEQ ID NO 124
<211> LENGTH: 13
<212> TYPE: PRT
<213> ORGANISM: Human immunodeficiency virus

<400> SEQUENCE: 124

Ser Trp Phe Ser Ile Ser Ser Trp Leu Trp Tyr Ile Lys
1               5                   10

<210> SEQ ID NO 125
<211> LENGTH: 13
<212> TYPE: PRT
<213> ORGANISM: Human immunodeficiency virus

<400> SEQUENCE: 125

Ser Trp Phe Ser Ile Ser His Trp Leu Trp Tyr Ile Lys
1               5                   10

<210> SEQ ID NO 126
<211> LENGTH: 13
<212> TYPE: PRT
<213> ORGANISM: Human immunodeficiency virus

<400> SEQUENCE: 126

Ser Trp Phe Asp Ile Thr Arg Trp Leu Trp Tyr Ile Arg
1               5                   10

<210> SEQ ID NO 127
<211> LENGTH: 13
<212> TYPE: PRT
<213> ORGANISM: Human immunodeficiency virus

<400> SEQUENCE: 127

Asn Trp Phe Lys Ile Thr Lys Trp Leu Trp Tyr Ile Lys
1               5                   10

<210> SEQ ID NO 128
<211> LENGTH: 13
<212> TYPE: PRT
<213> ORGANISM: Human immunodeficiency virus

<400> SEQUENCE: 128

Asn Trp Phe Asp Ile Ser Lys Trp Leu Gly Tyr Ile Gln
1               5                   10
```

```
<210> SEQ ID NO 129
<211> LENGTH: 13
<212> TYPE: PRT
<213> ORGANISM: Human immunodeficiency virus

<400> SEQUENCE: 129

Asp Trp Phe Ser Ile Ser Asn Trp Leu Trp Tyr Ile Lys
1               5                   10

<210> SEQ ID NO 130
<211> LENGTH: 13
<212> TYPE: PRT
<213> ORGANISM: Human immunodeficiency virus

<400> SEQUENCE: 130

Thr Trp Phe Ser Leu Thr Asn Trp Leu Trp Tyr Ile Arg
1               5                   10

<210> SEQ ID NO 131
<211> LENGTH: 13
<212> TYPE: PRT
<213> ORGANISM: Human immunodeficiency virus

<400> SEQUENCE: 131

Thr Trp Phe Ser Ile Thr Asn Trp Leu Trp Tyr Ile Arg
1               5                   10

<210> SEQ ID NO 132
<211> LENGTH: 13
<212> TYPE: PRT
<213> ORGANISM: Human immunodeficiency virus

<400> SEQUENCE: 132

Thr Trp Phe Ser Ile Thr Asn Trp Leu Trp Tyr Ile Lys
1               5                   10

<210> SEQ ID NO 133
<211> LENGTH: 13
<212> TYPE: PRT
<213> ORGANISM: Human immunodeficiency virus

<400> SEQUENCE: 133

Thr Trp Phe Ser Ile Ser Asn Trp Leu Trp Tyr Ile Arg
1               5                   10

<210> SEQ ID NO 134
<211> LENGTH: 13
<212> TYPE: PRT
<213> ORGANISM: Human immunodeficiency virus

<400> SEQUENCE: 134

Thr Trp Phe Ser Ile Ser Asn Trp Leu Trp Tyr Ile Lys
1               5                   10

<210> SEQ ID NO 135
<211> LENGTH: 13
<212> TYPE: PRT
<213> ORGANISM: Human immunodeficiency virus

<400> SEQUENCE: 135

Thr Trp Phe Gly Ile Ser Ser Trp Leu Trp Tyr Ile Lys
1               5                   10

<210> SEQ ID NO 136
<211> LENGTH: 13
```

<212> TYPE: PRT
<213> ORGANISM: Human immunodeficiency virus

<400> SEQUENCE: 136

Thr Trp Phe Gly Ile Ser Asn Trp Leu Trp Tyr Ile Lys
1               5                   10

<210> SEQ ID NO 137
<211> LENGTH: 13
<212> TYPE: PRT
<213> ORGANISM: Human immunodeficiency virus

<400> SEQUENCE: 137

Thr Trp Phe Asp Ile Thr Lys Trp Pro Trp Tyr Ile Lys
1               5                   10

<210> SEQ ID NO 138
<211> LENGTH: 13
<212> TYPE: PRT
<213> ORGANISM: Human immunodeficiency virus

<400> SEQUENCE: 138

Thr Trp Phe Asp Ile Ser Ser Trp Leu Trp Tyr Ile Arg
1               5                   10

<210> SEQ ID NO 139
<211> LENGTH: 13
<212> TYPE: PRT
<213> ORGANISM: Human immunodeficiency virus

<400> SEQUENCE: 139

Thr Trp Phe Asp Ile Ser Lys Trp Leu Trp Tyr Ile Arg
1               5                   10

<210> SEQ ID NO 140
<211> LENGTH: 13
<212> TYPE: PRT
<213> ORGANISM: Human immunodeficiency virus

<400> SEQUENCE: 140

Ser Trp Trp Asp Ile Ser Lys Trp Leu Trp Tyr Ile Arg
1               5                   10

<210> SEQ ID NO 141
<211> LENGTH: 13
<212> TYPE: PRT
<213> ORGANISM: Human immunodeficiency virus

<400> SEQUENCE: 141

Ser Trp Val Asp Ile Ser Asn Trp Leu Trp Tyr Ile Lys
1               5                   10

<210> SEQ ID NO 142
<211> LENGTH: 13
<212> TYPE: PRT
<213> ORGANISM: Human immunodeficiency virus

<400> SEQUENCE: 142

Ser Trp Leu Ser Ile Thr Asn Trp Leu Trp Tyr Ile Arg
1               5                   10

<210> SEQ ID NO 143
<211> LENGTH: 13
<212> TYPE: PRT
<213> ORGANISM: Human immunodeficiency virus

<400> SEQUENCE: 143

Ser Trp Leu Ser Ile Ser Asn Trp Leu Trp Tyr Ile Lys
1               5                   10

<210> SEQ ID NO 144
<211> LENGTH: 13
<212> TYPE: PRT
<213> ORGANISM: Human immunodeficiency virus

<400> SEQUENCE: 144

Ser Trp Phe Thr Leu Ser Asn Trp Leu Trp Tyr Ile Arg
1               5                   10

<210> SEQ ID NO 145
<211> LENGTH: 13
<212> TYPE: PRT
<213> ORGANISM: Human immunodeficiency virus

<400> SEQUENCE: 145

Ser Trp Phe Thr Ile Thr Lys Trp Leu Trp Tyr Ile Lys
1               5                   10

<210> SEQ ID NO 146
<211> LENGTH: 13
<212> TYPE: PRT
<213> ORGANISM: Human immunodeficiency virus

<400> SEQUENCE: 146

Ser Trp Phe Thr Ile Ser Asn Trp Leu Trp Tyr Ile Arg
1               5                   10

<210> SEQ ID NO 147
<211> LENGTH: 13
<212> TYPE: PRT
<213> ORGANISM: Human immunodeficiency virus

<400> SEQUENCE: 147

Ser Trp Phe Ser Ile Thr Lys Trp Leu Arg Tyr Ile Gln
1               5                   10

<210> SEQ ID NO 148
<211> LENGTH: 13
<212> TYPE: PRT
<213> ORGANISM: Human immunodeficiency virus

<400> SEQUENCE: 148

Ser Trp Phe Ser Ile Thr His Trp Leu Trp Tyr Ile Arg
1               5                   10

<210> SEQ ID NO 149
<211> LENGTH: 13
<212> TYPE: PRT
<213> ORGANISM: Human immunodeficiency virus

<400> SEQUENCE: 149

Ser Trp Phe Asn Met Thr Asn Trp Leu Trp Tyr Ile Lys
1               5                   10

<210> SEQ ID NO 150
<211> LENGTH: 13
<212> TYPE: PRT
<213> ORGANISM: Human immunodeficiency virus

<400> SEQUENCE: 150

Ser Trp Phe Asn Ile Thr Asn Trp Leu Trp Cys Ile Lys
1               5                   10

<210> SEQ ID NO 151
<211> LENGTH: 12
<212> TYPE: PRT
<213> ORGANISM: Human immunodeficiency virus

<400> SEQUENCE: 151

Ser Trp Phe Asn Ile Thr Asn Trp Leu Trp Ile Lys
1               5                   10

<210> SEQ ID NO 152
<211> LENGTH: 13
<212> TYPE: PRT
<213> ORGANISM: Human immunodeficiency virus

<400> SEQUENCE: 152

Ser Trp Phe Asn Ile Thr Lys Trp Leu Trp Tyr Ile Lys
1               5                   10

<210> SEQ ID NO 153
<211> LENGTH: 13
<212> TYPE: PRT
<213> ORGANISM: Human immunodeficiency virus

<400> SEQUENCE: 153

Ser Trp Phe Asn Ile Ser Ser Trp Leu Trp Tyr Ile Arg
1               5                   10

<210> SEQ ID NO 154
<211> LENGTH: 13
<212> TYPE: PRT
<213> ORGANISM: Human immunodeficiency virus

<400> SEQUENCE: 154

Ser Trp Phe Asn Ile Ser Lys Trp Leu Trp Tyr Ile Lys
1               5                   10

<210> SEQ ID NO 155
<211> LENGTH: 13
<212> TYPE: PRT
<213> ORGANISM: Human immunodeficiency virus

<400> SEQUENCE: 155

Ser Trp Phe Asn Ile Ser His Trp Leu Trp Tyr Ile Arg
1               5                   10

<210> SEQ ID NO 156
<211> LENGTH: 13
<212> TYPE: PRT
<213> ORGANISM: Human immunodeficiency virus

<400> SEQUENCE: 156

Ser Trp Phe His Ile Thr Asn Trp Leu Trp Tyr Ile Lys
1               5                   10

<210> SEQ ID NO 157
<211> LENGTH: 13
<212> TYPE: PRT
<213> ORGANISM: Human immunodeficiency virus

<400> SEQUENCE: 157

Ser Trp Phe Gly Ile Thr Gln Trp Leu Trp Tyr Ile Lys

<210> SEQ ID NO 158
<211> LENGTH: 13
<212> TYPE: PRT
<213> ORGANISM: Human immunodeficiency virus

<400> SEQUENCE: 158

Ser Trp Phe Asp Ile Thr Ser Trp Leu Trp Tyr Ile Lys
1               5                   10

<210> SEQ ID NO 159
<211> LENGTH: 13
<212> TYPE: PRT
<213> ORGANISM: Human immunodeficiency virus

<400> SEQUENCE: 159

Asn Trp Phe Asp Ile Thr His Trp Leu Trp Tyr Ile Arg
1               5                   10

<210> SEQ ID NO 160
<211> LENGTH: 13
<212> TYPE: PRT
<213> ORGANISM: Human immunodeficiency virus

<400> SEQUENCE: 160

Asp Trp Phe Ser Ile Thr Lys Trp Leu Trp Tyr Ile Lys
1               5                   10

<210> SEQ ID NO 161
<211> LENGTH: 13
<212> TYPE: PRT
<213> ORGANISM: Human immunodeficiency virus

<400> SEQUENCE: 161

Thr Trp Phe Asn Ile Thr Asn Trp Leu Trp Tyr Ile Arg
1               5                   10

<210> SEQ ID NO 162
<211> LENGTH: 13
<212> TYPE: PRT
<213> ORGANISM: Human immunodeficiency virus

<400> SEQUENCE: 162

Thr Trp Phe Gly Leu Asn Lys Trp Met Arg Tyr Ile Lys
1               5                   10

<210> SEQ ID NO 163
<211> LENGTH: 13
<212> TYPE: PRT
<213> ORGANISM: Human immunodeficiency virus

<400> SEQUENCE: 163

Thr Trp Phe Asp Leu Thr Asn Trp Leu Trp Tyr Ile Arg
1               5                   10

<210> SEQ ID NO 164
<211> LENGTH: 13
<212> TYPE: PRT
<213> ORGANISM: Human immunodeficiency virus

<400> SEQUENCE: 164

Thr Trp Phe Asp Ile Ser Asn Trp Met Arg Tyr Ile Gln
1               5                   10

<210> SEQ ID NO 165
<211> LENGTH: 13
<212> TYPE: PRT
<213> ORGANISM: Human immunodeficiency virus

<400> SEQUENCE: 165

Thr Trp Phe Asp Ile Ser Lys Trp Leu Trp Tyr Ile Lys
1               5                   10

<210> SEQ ID NO 166
<211> LENGTH: 13
<212> TYPE: PRT
<213> ORGANISM: Human immunodeficiency virus
<220> FEATURE:
<221> NAME/KEY: MOD_RES
<222> LOCATION: (2)..(2)
<223> OTHER INFORMATION: Any amino acid

<400> SEQUENCE: 166

Ser Xaa Phe Ser Ile Thr Asn Trp Leu Trp Tyr Ile Arg
1               5                   10

<210> SEQ ID NO 167
<211> LENGTH: 13
<212> TYPE: PRT
<213> ORGANISM: Human immunodeficiency virus

<400> SEQUENCE: 167

Ser Trp Tyr Asp Ile Ser Asn Trp Leu Trp Tyr Ile Lys
1               5                   10

<210> SEQ ID NO 168
<211> LENGTH: 13
<212> TYPE: PRT
<213> ORGANISM: Human immunodeficiency virus

<400> SEQUENCE: 168

Ser Trp Leu Asp Ile Thr Asn Trp Leu Trp Tyr Ile Arg
1               5                   10

<210> SEQ ID NO 169
<211> LENGTH: 13
<212> TYPE: PRT
<213> ORGANISM: Human immunodeficiency virus

<400> SEQUENCE: 169

Ser Trp Leu Asp Ile Ser Asn Trp Leu Lys Tyr Ile Lys
1               5                   10

<210> SEQ ID NO 170
<211> LENGTH: 13
<212> TYPE: PRT
<213> ORGANISM: Human immunodeficiency virus

<400> SEQUENCE: 170

Ser Trp Leu Asp Ile Ser Asn Trp Leu Gly Tyr Ile Lys
1               5                   10

<210> SEQ ID NO 171
<211> LENGTH: 13
<212> TYPE: PRT
<213> ORGANISM: Human immunodeficiency virus

<400> SEQUENCE: 171

Ser Trp Leu Asp Ile Ser His Trp Leu Trp Tyr Ile Arg

```
1               5                   10
```

<210> SEQ ID NO 172
<211> LENGTH: 13
<212> TYPE: PRT
<213> ORGANISM: Human immunodeficiency virus

<400> SEQUENCE: 172

```
Ser Trp Phe Thr Ile Ser Lys Trp Leu Trp Tyr Ile Lys
1               5                   10
```

<210> SEQ ID NO 173
<211> LENGTH: 13
<212> TYPE: PRT
<213> ORGANISM: Human immunodeficiency virus

<400> SEQUENCE: 173

```
Ser Trp Phe Ser Leu Thr Asn Trp Leu Trp Tyr Ile Lys
1               5                   10
```

<210> SEQ ID NO 174
<211> LENGTH: 13
<212> TYPE: PRT
<213> ORGANISM: Human immunodeficiency virus

<400> SEQUENCE: 174

```
Ser Trp Phe Ser Ile Val Asn Trp Leu Trp Tyr Ile Lys
1               5                   10
```

<210> SEQ ID NO 175
<211> LENGTH: 13
<212> TYPE: PRT
<213> ORGANISM: Human immunodeficiency virus

<400> SEQUENCE: 175

```
Ser Trp Phe Ser Ile Thr Asn Trp Leu Arg Tyr Ile Lys
1               5                   10
```

<210> SEQ ID NO 176
<211> LENGTH: 13
<212> TYPE: PRT
<213> ORGANISM: Human immunodeficiency virus

<400> SEQUENCE: 176

```
Ser Trp Phe Ser Ile Thr Glu Trp Leu Trp Tyr Ile Lys
1               5                   10
```

<210> SEQ ID NO 177
<211> LENGTH: 13
<212> TYPE: PRT
<213> ORGANISM: Human immunodeficiency virus

<400> SEQUENCE: 177

```
Ser Trp Phe Gln Leu Ser Lys Trp Met Trp Tyr Ile Lys
1               5                   10
```

<210> SEQ ID NO 178
<211> LENGTH: 13
<212> TYPE: PRT
<213> ORGANISM: Human immunodeficiency virus

<400> SEQUENCE: 178

```
Ser Trp Phe Glu Ile Ser Asn Trp Leu Trp Tyr Ile Lys
1               5                   10
```

<210> SEQ ID NO 179
<211> LENGTH: 13
<212> TYPE: PRT
<213> ORGANISM: Human immunodeficiency virus

<400> SEQUENCE: 179

Ser Trp Phe Asp Leu Thr Asn Trp Leu Trp Tyr Ile Arg
1               5                   10

<210> SEQ ID NO 180
<211> LENGTH: 13
<212> TYPE: PRT
<213> ORGANISM: Human immunodeficiency virus

<400> SEQUENCE: 180

Ser Trp Phe Asp Ile Thr Arg Trp Met Lys Tyr Val Lys
1               5                   10

<210> SEQ ID NO 181
<211> LENGTH: 13
<212> TYPE: PRT
<213> ORGANISM: Human immunodeficiency virus

<400> SEQUENCE: 181

Ser Trp Phe Asp Ile Thr Asn Trp Leu Trp Tyr Ile Gln
1               5                   10

<210> SEQ ID NO 182
<211> LENGTH: 13
<212> TYPE: PRT
<213> ORGANISM: Human immunodeficiency virus

<400> SEQUENCE: 182

Ser Trp Phe Asp Ile Ser Asn Trp Leu Arg Tyr Ile Arg
1               5                   10

<210> SEQ ID NO 183
<211> LENGTH: 13
<212> TYPE: PRT
<213> ORGANISM: Human immunodeficiency virus

<400> SEQUENCE: 183

Thr Trp Phe Asp Ile Thr His Trp Leu Trp Tyr Ile Arg
1               5                   10

<210> SEQ ID NO 184
<211> LENGTH: 13
<212> TYPE: PRT
<213> ORGANISM: Human immunodeficiency virus

<400> SEQUENCE: 184

Ser Trp Phe Gly Ile Thr Asn Trp Leu Trp Tyr Ile Arg
1               5                   10

<210> SEQ ID NO 185
<211> LENGTH: 13
<212> TYPE: PRT
<213> ORGANISM: Human immunodeficiency virus

<400> SEQUENCE: 185

Ser Trp Phe Asp Ile Ser Arg Trp Leu Trp Tyr Ile Arg
1               5                   10

<210> SEQ ID NO 186

```
<210> SEQ ID NO 186
<211> LENGTH: 13
<212> TYPE: PRT
<213> ORGANISM: Human immunodeficiency virus

<400> SEQUENCE: 186

Asn Trp Phe Thr Ile Thr Asn Trp Leu Trp Tyr Ile Arg
1               5                   10

<210> SEQ ID NO 187
<211> LENGTH: 13
<212> TYPE: PRT
<213> ORGANISM: Human immunodeficiency virus

<400> SEQUENCE: 187

Asn Trp Phe Ser Ile Ser Ser Trp Leu Trp Tyr Ile Lys
1               5                   10

<210> SEQ ID NO 188
<211> LENGTH: 13
<212> TYPE: PRT
<213> ORGANISM: Human immunodeficiency virus

<400> SEQUENCE: 188

Asn Trp Phe Asn Ile Thr Ser Trp Leu Trp Tyr Ile Lys
1               5                   10

<210> SEQ ID NO 189
<211> LENGTH: 13
<212> TYPE: PRT
<213> ORGANISM: Human immunodeficiency virus

<400> SEQUENCE: 189

Asn Trp Phe Asn Ile Ser Lys Trp Leu Trp Tyr Ile Arg
1               5                   10

<210> SEQ ID NO 190
<211> LENGTH: 13
<212> TYPE: PRT
<213> ORGANISM: Human immunodeficiency virus

<400> SEQUENCE: 190

Asn Trp Phe Asp Ile Ser His Trp Leu Trp Tyr Ile Arg
1               5                   10

<210> SEQ ID NO 191
<211> LENGTH: 13
<212> TYPE: PRT
<213> ORGANISM: Human immunodeficiency virus

<400> SEQUENCE: 191

Asp Trp Leu Asp Ile Thr Lys Trp Leu Trp Tyr Ile Lys
1               5                   10

<210> SEQ ID NO 192
<211> LENGTH: 13
<212> TYPE: PRT
<213> ORGANISM: Human immunodeficiency virus

<400> SEQUENCE: 192

Asp Trp Phe Asp Ile Thr Ser Trp Leu Trp Tyr Ile Arg
1               5                   10

<210> SEQ ID NO 193
<211> LENGTH: 13
<212> TYPE: PRT
```

```
<213> ORGANISM: Human immunodeficiency virus
<220> FEATURE:
<221> NAME/KEY: MOD_RES
<222> LOCATION: (1)..(1)
<223> OTHER INFORMATION: Any amino acid

<400> SEQUENCE: 193

Xaa Trp Phe Asp Ile Ser Arg Trp Leu Trp Tyr Ile Lys
1               5                   10

<210> SEQ ID NO 194
<211> LENGTH: 13
<212> TYPE: PRT
<213> ORGANISM: Human immunodeficiency virus

<400> SEQUENCE: 194

Thr Trp Phe Asn Ile Thr Gln Trp Leu Trp Tyr Ile Lys
1               5                   10

<210> SEQ ID NO 195
<211> LENGTH: 13
<212> TYPE: PRT
<213> ORGANISM: Human immunodeficiency virus

<400> SEQUENCE: 195

Thr Trp Phe Gly Ile Ser Asn Trp Leu Trp Tyr Ile Arg
1               5                   10

<210> SEQ ID NO 196
<211> LENGTH: 13
<212> TYPE: PRT
<213> ORGANISM: Human immunodeficiency virus

<400> SEQUENCE: 196

Thr Trp Phe Asp Leu Thr Asn Trp Leu Trp Tyr Ile Lys
1               5                   10

<210> SEQ ID NO 197
<211> LENGTH: 13
<212> TYPE: PRT
<213> ORGANISM: Human immunodeficiency virus

<400> SEQUENCE: 197

Thr Trp Phe Asp Leu Ser Asn Trp Leu Trp Tyr Ile Lys
1               5                   10

<210> SEQ ID NO 198
<211> LENGTH: 13
<212> TYPE: PRT
<213> ORGANISM: Human immunodeficiency virus

<400> SEQUENCE: 198

Thr Trp Phe Asp Ile Thr His Trp Leu Trp Tyr Ile Lys
1               5                   10

<210> SEQ ID NO 199
<211> LENGTH: 13
<212> TYPE: PRT
<213> ORGANISM: Human immunodeficiency virus

<400> SEQUENCE: 199

Thr Trp Phe Asp Ile Ser Ser Trp Leu Trp Tyr Ile Lys
1               5                   10

<210> SEQ ID NO 200
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Glu His His His His His His
1               5

<210> SEQ ID NO 201
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
                20                  25                  30

Lys Gln Lys Glu Pro Arg Asp Asp Glu Ile Asn Arg Trp Ile Asp Ile
            35                  40                  45

Val Lys Lys Lys Ala Asp Glu Ala Lys Lys Arg Val Glu Glu Val Gly
    50                  55                  60

Asp Gln Ala Ala Asp Glu Ala Ala Gln Leu Gly Asn Asp Pro Asn Val
65                  70                  75                  80

Asn Trp Phe Asp Ile Thr Asn Val Leu Trp Asp Val Lys Lys Leu Thr
                85                  90                  95

Glu Lys Ala Ile Asn Asp Ile Asp Ala Leu Lys Lys Met Lys Asp
            100                 105                 110

Trp Leu Glu Ser Gly
        115

<210> SEQ ID NO 202
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
                20                  25                  30

Lys Gln Lys Glu Pro Arg Asp Asp Glu Ile Asn Arg Trp Ile Asp Ile
            35                  40                  45

Val Lys Lys Lys Ala Asp Glu Ala Lys Lys Arg Val Glu Glu Val Gly
    50                  55                  60

Asp Gln Ala Ala Asp Glu Ala Ala Gln Leu Gly Asn Asp Pro Asn Val
65                  70                  75                  80

Asn Trp Phe Ser Ile Thr Lys Val Leu Trp Asp Val Lys Lys Leu Thr
                85                  90                  95

Glu Lys Ala Ile Asn Asp Ile Asp Ala Leu Lys Lys Met Lys Asp
            100                 105                 110
```

Trp Leu Glu Ser Gly
        115

<210> SEQ ID NO 203
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gly Lys Ala Asp Glu Val Arg Glu Lys Ala Arg Arg Arg Met Glu Gln
1               5                   10                  15

Ala Val Glu Glu Phe Lys Arg Arg Leu Arg Gln Phe Glu Glu Lys Val
            20                  25                  30

Lys Gln Lys Glu Pro Arg Asp Asp Glu Ile Asn Arg Trp Ile Asp Ile
        35                  40                  45

Val Lys Lys Lys Ala Asp Glu Ala Lys Lys Arg Val Glu Glu Val Gly
    50                  55                  60

Asp Gln Ala Ala Asp Glu Ala Ala Gln Leu Gly Asn Asp Pro Asn Val
65                  70                  75                  80

Ser Trp Phe Asn Ile Ser Asn Val Leu Trp Asp Val Arg Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly
        115

<210> SEQ ID NO 204
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Lys Ala Asp Glu Val Arg Glu Lys Ala Arg Arg Arg Met Glu Gln
1               5                   10                  15

Ala Val Glu Glu Phe Lys Arg Arg Leu Arg Gln Phe Glu Glu Lys Val
            20                  25                  30

Lys Gln Lys Glu Pro Arg Asp Asp Glu Ile Asn Arg Trp Ile Asp Ile
        35                  40                  45

Val Lys Lys Lys Ala Asp Glu Ala Lys Lys Arg Val Glu Glu Val Gly
    50                  55                  60

Asp Gln Ala Ala Asp Glu Ala Ala Gln Leu Gly Asn Asp Pro Asn Val
65                  70                  75                  80

Asn Trp Phe Asp Ile Ser Arg Val Leu Trp Asp Val Lys Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly
        115

<210> SEQ ID NO 205
<211> LENGTH: 117
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 205

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
            20                  25                  30

Lys Gln Lys Glu Pro Arg Asp Asp Glu Ile Asn Arg Trp Ile Asp Ile
        35                  40                  45

Val Lys Lys Lys Ala Asp Glu Ala Lys Arg Val Glu Glu Val Gly
50                  55                  60

Asp Gln Ala Ala Asp Glu Ala Ala Gln Leu Gly Asn Asp Pro Asn Val
65                  70                  75                  80

Asn Trp Phe Asp Ile Thr Gln Val Leu Trp Val Lys Lys Leu Thr
            85                  90                  95

Glu Lys Ala Ile Asn Asp Ile Asp Asp Ala Leu Lys Lys Met Lys Asp
            100                 105                 110

Trp Leu Glu Ser Gly
        115

<210> SEQ ID NO 206
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
            85                  90                  95

Glu Pro Asp Pro Val Pro Val Arg Val Val Phe Met Leu Ala Leu Gly
            100                 105                 110

Asn Trp Phe Asp Ile Thr Asn Val Leu Trp Trp Ile Lys Ala Val Ile
            115                 120                 125

Gln Asp Glu Asp Phe Met Gln Gln Leu Leu Val Met Asn Asp Asp Glu
        130                 135                 140

Ile Tyr Gln Ser Ile Tyr Thr Arg Ile Ser Glu Leu Glu His His
145                 150                 155                 160

His His His

<210> SEQ ID NO 207
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 207

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Ser Ile Thr Lys Val Leu Trp Trp Ile Lys Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu
145                 150                 155

<210> SEQ ID NO 208
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Ser Trp Phe Asn Ile Ser Asn Val Leu Trp Trp Ile Arg Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu
145                 150                 155

<210> SEQ ID NO 209
<211> LENGTH: 155
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 209

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Asp Ile Ser Arg Val Leu Trp Trp Ile Lys Ala Val Ile
            115                 120                 125

Gln Asp Glu Asp Phe Met Gln Gln Leu Leu Val Met Asn Asp Asp Glu
        130                 135                 140

Ile Tyr Gln Ser Ile Tyr Thr Arg Ile Ser Glu
145                 150                 155

<210> SEQ ID NO 210
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Asp Ile Thr Gln Val Leu Trp Trp Ile Lys Ala Val Ile
            115                 120                 125

Gln Asp Glu Asp Phe Met Gln Gln Leu Leu Val Met Asn Asp Asp Glu
        130                 135                 140

Ile Tyr Gln Ser Ile Tyr Thr Arg Ile Ser Glu
145                 150                 155

```
<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

His His His His His His Gly Gly
1               5

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Tyr Ile Lys Ala Asn Ser Lys Phe Ile Gly Ile Thr Glu Leu
1               5                   10                  15

<210> SEQ ID NO 213
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Lys Ala Asp Glu Val Arg Glu Lys Ala Arg Arg Arg Met Glu Gln
1               5                   10                  15

Ala Val Glu Glu Phe Lys Arg Arg Leu Arg Gln Phe Glu Glu Lys Val
                20                  25                  30

Lys Gln Lys Glu Pro Arg Asp Asp Glu Ile Asn Arg Trp Ile Asp Ile
            35                  40                  45

Val Lys Lys Lys Ala Asp Glu Ala Lys Arg Val Glu Glu Val Gly
        50                  55                  60

Asp Gln Ala Ala Asp Glu Ala Ala Gln Leu Gly Asn Asp Pro Asn Val
65                  70                  75                  80

Asn Trp Phe Asp Ile Thr Asn Val Leu Trp Asp Val Lys Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly Gly His His His His His Gly Gly Gln Tyr
        115                 120                 125

Ile Lys Ala Asn Ser Lys Phe Ile Gly Ile Thr Glu Leu
    130                 135                 140

<210> SEQ ID NO 214
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gly Lys Ala Asp Glu Val Arg Glu Lys Ala Arg Arg Arg Met Glu Gln
1               5                   10                  15
```

```
Ala Val Glu Glu Phe Lys Arg Arg Leu Arg Gln Phe Glu Glu Lys Val
            20                  25                  30

Lys Gln Lys Glu Pro Arg Asp Asp Glu Ile Asn Arg Trp Ile Asp Ile
        35                  40                  45

Val Lys Lys Lys Ala Asp Glu Ala Lys Lys Arg Val Glu Glu Val Gly
50                  55                  60

Asp Gln Ala Ala Asp Glu Ala Ala Gln Leu Gly Asn Asp Pro Asn Val
65                  70                  75                  80

Asn Trp Phe Ser Ile Thr Lys Val Leu Trp Asp Val Lys Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly Gly His His His His His Gly Gly Gln Tyr
        115                 120                 125

Ile Lys Ala Asn Ser Lys Phe Ile Gly Ile Thr Glu Leu
    130                 135                 140
```

<210> SEQ ID NO 215
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

```
Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
            20                  25                  30

Lys Gln Lys Glu Pro Arg Asp Asp Glu Ile Asn Arg Trp Ile Asp Ile
        35                  40                  45

Val Lys Lys Lys Ala Asp Glu Ala Lys Lys Arg Val Glu Glu Val Gly
50                  55                  60

Asp Gln Ala Ala Asp Glu Ala Ala Gln Leu Gly Asn Asp Pro Asn Val
65                  70                  75                  80

Ser Trp Phe Asn Ile Ser Asn Val Leu Trp Asp Val Arg Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly Gly His His His His His Gly Gly Gln Tyr
        115                 120                 125

Ile Lys Ala Asn Ser Lys Phe Ile Gly Ile Thr Glu Leu
    130                 135                 140
```

<210> SEQ ID NO 216
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

```
Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
            20                  25                  30
```

```
Lys Gln Lys Glu Pro Arg Asp Asp Glu Ile Asn Arg Trp Ile Asp Ile
        35                  40                  45

Val Lys Lys Lys Ala Asp Glu Ala Lys Lys Arg Val Glu Glu Val Gly
 50                  55                  60

Asp Gln Ala Ala Asp Glu Ala Ala Gln Leu Gly Asn Asp Pro Asn Val
 65                  70                  75                  80

Asn Trp Phe Asp Ile Ser Arg Val Leu Trp Asp Val Lys Lys Leu Thr
                 85                  90                  95

Glu Lys Ala Ile Asn Asp Ile Asp Ala Leu Lys Lys Met Lys Asp
                100                 105                 110

Trp Leu Glu Ser Gly Gly His His His His His Gly Gly Gln Tyr
        115                 120                 125

Ile Lys Ala Asn Ser Lys Phe Ile Gly Ile Thr Glu Leu
        130                 135                 140

<210> SEQ ID NO 217
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gly Lys Ala Asp Glu Val Arg Glu Lys Ala Arg Arg Met Glu Gln
 1               5                  10                  15

Ala Val Glu Glu Phe Lys Arg Arg Leu Arg Gln Phe Glu Glu Lys Val
                 20                  25                  30

Lys Gln Lys Glu Pro Arg Asp Asp Glu Ile Asn Arg Trp Ile Asp Ile
        35                  40                  45

Val Lys Lys Lys Ala Asp Glu Ala Lys Lys Arg Val Glu Glu Val Gly
 50                  55                  60

Asp Gln Ala Ala Asp Glu Ala Ala Gln Leu Gly Asn Asp Pro Asn Val
 65                  70                  75                  80

Asn Trp Phe Asp Ile Thr Gln Val Leu Trp Asp Val Lys Lys Leu Thr
                 85                  90                  95

Glu Lys Ala Ile Asn Asp Ile Asp Ala Leu Lys Lys Met Lys Asp
                100                 105                 110

Trp Leu Glu Ser Gly Gly His His His His His Gly Gly Gln Tyr
        115                 120                 125

Ile Lys Ala Asn Ser Lys Phe Ile Gly Ile Thr Glu Leu
        130                 135                 140

<210> SEQ ID NO 218
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Asn Ala Met Gln Gly Ile His Phe Arg Arg His Tyr Val Arg His Leu
 1               5                  10                  15

Pro Lys Glu Val Ser Gln Asn Asp Ile Ile Lys Ala Leu Ala Ser Pro
                 20                  25                  30

Leu Ile Asn Asp Gly Met Val Val Ser Asp Phe Ala Asp His Val Ile
        35                  40                  45
```

Thr Arg Glu Gln Asn Phe Pro Thr Gly Leu Pro Val Glu Pro Val Gly
 50                  55                  60

Val Ala Ile Pro His Thr Asp Ser Lys Tyr Val Arg Gln Asn Ala Ile
 65                  70                  75                  80

Ser Val Gly Ile Leu Ala Glu Pro Val Asn Phe Glu Asp Ala Gly Gly
                 85                  90                  95

Glu Pro Asp Pro Val Pro Val Arg Val Val Phe Met Leu Ala Leu Gly
            100                 105                 110

Asn Trp Phe Asp Ile Thr Asn Val Leu Trp Trp Ile Lys Ala Val Ile
            115                 120                 125

Gln Asp Glu Asp Phe Met Gln Gln Leu Leu Val Met Asn Asp Asp Glu
130                 135                 140

Ile Tyr Gln Ser Ile Tyr Thr Arg Ile Ser Glu Gly His His His
145                 150                 155                 160

His His His Gly Gly Gln Tyr Ile Lys Ala Asn Ser Lys Phe Ile Gly
                165                 170                 175

Ile Thr Glu Leu
            180

<210> SEQ ID NO 219
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Asn Ala Met Gln Gly Ile His Phe Arg Arg His Tyr Val Arg His Leu
 1               5                  10                  15

Pro Lys Glu Val Ser Gln Asn Asp Ile Ile Lys Ala Leu Ala Ser Pro
                20                  25                  30

Leu Ile Asn Asp Gly Met Val Val Ser Asp Phe Ala Asp His Val Ile
             35                  40                  45

Thr Arg Glu Gln Asn Phe Pro Thr Gly Leu Pro Val Glu Pro Val Gly
 50                  55                  60

Val Ala Ile Pro His Thr Asp Ser Lys Tyr Val Arg Gln Asn Ala Ile
 65                  70                  75                  80

Ser Val Gly Ile Leu Ala Glu Pro Val Asn Phe Glu Asp Ala Gly Gly
                 85                  90                  95

Glu Pro Asp Pro Val Pro Val Arg Val Val Phe Met Leu Ala Leu Gly
            100                 105                 110

Asn Trp Phe Ser Ile Thr Lys Val Leu Trp Trp Ile Lys Ala Val Ile
            115                 120                 125

Gln Asp Glu Asp Phe Met Gln Gln Leu Leu Val Met Asn Asp Asp Glu
130                 135                 140

Ile Tyr Gln Ser Ile Tyr Thr Arg Ile Ser Glu Gly His His His
145                 150                 155                 160

His His His Gly Gly Gln Tyr Ile Lys Ala Asn Ser Lys Phe Ile Gly
                165                 170                 175

Ile Thr Glu Leu
            180

<210> SEQ ID NO 220
<211> LENGTH: 180
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 220

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Ser Trp Phe Asn Ile Ser Asn Val Leu Trp Trp Ile Arg Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu Gly Gly His His His
145                 150                 155                 160

His His His Gly Gly Gln Tyr Ile Lys Ala Asn Ser Lys Phe Ile Gly
                165                 170                 175

Ile Thr Glu Leu
            180

<210> SEQ ID NO 221
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Asp Ile Ser Arg Val Leu Trp Trp Ile Lys Ala Val Ile
        115                 120                 125

Gln Asp Glu Asp Phe Met Gln Gln Leu Leu Val Met Asn Asp Asp Glu
    130                 135                 140
```

```
Ile Tyr Gln Ser Ile Tyr Thr Arg Ile Ser Glu Gly His His His
145                 150                 155                 160

His His His Gly Gly Gln Tyr Ile Lys Ala Asn Ser Lys Phe Ile Gly
            165                 170                 175

Ile Thr Glu Leu
            180

<210> SEQ ID NO 222
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Asp Ile Thr Gln Val Leu Trp Trp Ile Lys Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu Gly His His His
145                 150                 155                 160

His His His Gly Gly Gln Tyr Ile Lys Ala Asn Ser Lys Phe Ile Gly
            165                 170                 175

Ile Thr Glu Leu
            180

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

His His His His His His
1               5

<210> SEQ ID NO 224
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 224

Asn Ala Met Ala Gly Ile Val Phe Arg Lys His Tyr Val Arg His Leu
1               5                   10                  15

Gly Lys Thr Val Thr Gln Asn Glu Ile Ile Arg Ala Leu Ala Ala Pro
            20                  25                  30

Leu Ile Ser Asp Gly Met Val Val Lys Asp Phe Ala Asp His Val Ile
        35                  40                  45

Lys Arg Glu Glu Gln Asn Pro Thr Gly Leu Pro Val Gln Pro Val Gly
50                  55                  60

Val Ala Ile Pro His Thr Asp Ser Lys Tyr Val Tyr Tyr Asn Ala Ile
65                  70                  75                  80

Ser Val Gly Ile Leu Gln Glu Pro Val Ala Phe Glu Asp Ala Gly Gly
            85                  90                  95

Asp Gly Arg Pro Val Pro Val Arg Val Val Phe Met Leu Ala Leu Gly
                100                 105                 110

Asn Trp Phe Asp Ile Thr Asn Val Leu Trp Trp Ile Lys Ala Val Ile
            115                 120                 125

Gln Asp Asp Glu Phe Met Lys Arg Leu Leu Tyr Met Thr Asp Asp Lys
130                 135                 140

Ile Tyr Glu Ser Ile Arg Lys Arg Ile Tyr Asp Leu Glu
145                 150                 155

<210> SEQ ID NO 225
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Asn Ala Met Ala Gly Ile Val Phe Arg Lys His Tyr Val Arg His Leu
1               5                   10                  15

Gly Lys Thr Val Thr Gln Asn Glu Ile Ile Arg Ala Leu Ala Ala Pro
            20                  25                  30

Leu Ile Ser Asp Gly Met Val Val Lys Asp Phe Ala Asp His Val Ile
        35                  40                  45

Lys Arg Glu Glu Gln Asn Pro Thr Gly Leu Pro Val Gln Pro Val Gly
50                  55                  60

Val Ala Ile Pro His Thr Asp Ser Lys Tyr Val Tyr Tyr Asn Ala Ile
65                  70                  75                  80

Ser Val Gly Ile Leu Gln Glu Pro Val Ala Phe Glu Asp Ala Gly Gly
            85                  90                  95

Asp Gly Arg Pro Val Pro Val Arg Val Val Phe Met Leu Ala Leu Gly
                100                 105                 110

Asn Trp Phe Ser Ile Thr Lys Val Leu Trp Trp Ile Lys Ala Val Ile
            115                 120                 125

Gln Asp Asp Glu Phe Met Lys Arg Leu Leu Tyr Met Thr Asp Asp Lys
130                 135                 140

Ile Tyr Glu Ser Ile Arg Lys Arg Ile Tyr Asp
145                 150                 155

<210> SEQ ID NO 226
<211> LENGTH: 155
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 226

```
Asn Ala Met Ala Gly Ile Val Phe Arg Lys His Tyr Val Arg His Leu
1               5                   10                  15

Gly Lys Thr Val Thr Gln Asn Glu Ile Ile Arg Ala Leu Ala Ala Pro
            20                  25                  30

Leu Ile Ser Asp Gly Met Val Lys Asp Phe Ala Asp His Val Ile
        35                  40                  45

Lys Arg Glu Glu Gln Asn Pro Thr Gly Leu Pro Val Gln Pro Val Gly
50                  55                  60

Val Ala Ile Pro His Thr Asp Ser Lys Tyr Val Tyr Tyr Asn Ala Ile
65                  70                  75                  80

Ser Val Gly Ile Leu Gln Glu Pro Val Ala Phe Glu Asp Ala Gly Gly
                85                  90                  95

Asp Gly Arg Pro Val Pro Val Arg Val Val Phe Met Leu Ala Leu Gly
                100                 105                 110

Ser Trp Phe Asn Ile Ser Asn Val Leu Trp Ile Arg Ala Val Ile
            115                 120                 125

Gln Asp Asp Glu Phe Met Lys Arg Leu Leu Tyr Met Thr Asp Asp Lys
130                 135                 140

Ile Tyr Glu Ser Ile Arg Lys Arg Ile Tyr Asp
145                 150                 155
```

<210> SEQ ID NO 227
<211> LENGTH: 155
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 227

```
Asn Ala Met Ala Gly Ile Val Phe Arg Lys His Tyr Val Arg His Leu
1               5                   10                  15

Gly Lys Thr Val Thr Gln Asn Glu Ile Ile Arg Ala Leu Ala Ala Pro
            20                  25                  30

Leu Ile Ser Asp Gly Met Val Val Lys Asp Phe Ala Asp His Val Ile
        35                  40                  45

Lys Arg Glu Glu Gln Asn Pro Thr Gly Leu Pro Val Gln Pro Val Gly
50                  55                  60

Val Ala Ile Pro His Thr Asp Ser Lys Tyr Val Tyr Tyr Asn Ala Ile
65                  70                  75                  80

Ser Val Gly Ile Leu Gln Glu Pro Val Ala Phe Glu Asp Ala Gly Gly
                85                  90                  95

Asp Gly Arg Pro Val Pro Val Arg Val Val Phe Met Leu Ala Leu Gly
                100                 105                 110

Asn Trp Phe Asp Ile Ser Arg Val Leu Trp Trp Ile Lys Ala Val Ile
            115                 120                 125

Gln Asp Asp Glu Phe Met Lys Arg Leu Leu Tyr Met Thr Asp Asp Lys
130                 135                 140

Ile Tyr Glu Ser Ile Arg Lys Arg Ile Tyr Asp
145                 150                 155
```

<210> SEQ ID NO 228

```
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Asn Ala Met Ala Gly Ile Val Phe Arg Lys His Tyr Val Arg His Leu
1               5                   10                  15

Gly Lys Thr Val Thr Gln Asn Glu Ile Ile Arg Ala Leu Ala Ala Pro
            20                  25                  30

Leu Ile Ser Asp Gly Met Val Val Lys Asp Phe Ala Asp His Val Ile
        35                  40                  45

Lys Arg Glu Glu Gln Asn Pro Thr Gly Leu Pro Val Gln Pro Val Gly
    50                  55                  60

Val Ala Ile Pro His Thr Asp Ser Lys Tyr Val Tyr Asn Ala Ile
65                  70                  75                  80

Ser Val Gly Ile Leu Gln Glu Pro Val Ala Phe Glu Asp Ala Gly Gly
                85                  90                  95

Asp Gly Arg Pro Val Pro Val Arg Val Val Phe Met Leu Ala Leu Gly
            100                 105                 110

Asn Trp Phe Asp Ile Thr Gln Val Leu Trp Trp Ile Lys Ala Val Ile
        115                 120                 125

Gln Asp Asp Glu Phe Met Lys Arg Leu Leu Tyr Met Thr Asp Asp Lys
    130                 135                 140

Ile Tyr Glu Ser Ile Arg Lys Arg Ile Tyr Asp
145                 150                 155

<210> SEQ ID NO 229
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Asn Ala Met Gln Gly Ile His Phe Arg Arg His Tyr Val Arg His Leu
1               5                   10                  15

Pro Lys Asn Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Asn Asn Ser Pro Thr Gly Leu Pro Val Glu Pro Val Gly
    50                  55                  60

Val Ala Ile Pro His Thr Asp Ser Lys Tyr Val Asn Gln Ser Ala Ile
65                  70                  75                  80

Ser Val Gly Ile Leu Ala Glu Pro Val Asn Phe Glu Asp Ala Asn Gly
                85                  90                  95

Thr Pro Asp Pro Val Pro Val Arg Val Val Phe Met Leu Ala Leu Gly
            100                 105                 110

Asn Trp Phe Asp Ile Thr Asn Val Leu Trp Trp Ile Lys Ala Val Ile
        115                 120                 125

Gln Asp Glu Asp Phe Met Gln Gln Leu Leu Asn Met Ser Asp Asp Glu
    130                 135                 140

Ile Tyr Gln Ser Ile Tyr Thr Arg Ile Ser Glu
145                 150                 155
```

<210> SEQ ID NO 230
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asn Ala Met Gln Gly Ile His Phe Arg Arg His Tyr Val Arg His Leu
1               5                   10                  15

Pro Lys Asn Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Asn Asn Ser Pro Thr Gly Leu Pro Val Glu Pro Val Gly
    50                  55                  60

Val Ala Ile Pro His Thr Asp Ser Lys Tyr Val Asn Gln Ser Ala Ile
65                  70                  75                  80

Ser Val Gly Ile Leu Ala Glu Pro Val Asn Phe Glu Asp Ala Asn Gly
                85                  90                  95

Thr Pro Asp Pro Val Pro Val Arg Val Val Phe Met Leu Ala Leu Gly
            100                 105                 110

Asn Trp Phe Asp Ile Thr Asn Val Leu Trp Trp Ile Lys Ala Val Ile
        115                 120                 125

Gln Asn Ala Ser Phe Met Gln Gln Leu Leu Asn Met Ser Asp Asp Glu
    130                 135                 140

Ile Tyr Gln Ser Ile Tyr Thr Arg Ile Ser Glu
145                 150                 155

<210> SEQ ID NO 231
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gly Ser Glu Val Ser Gln Asn Asp Ile Ile Lys Ala Leu Ala Ser Pro
1               5                   10                  15

Leu Ile Asn Asp Gly Met Val Val Ser Asp Phe Ala Asp His Val Ile
            20                  25                  30

Thr Arg Glu Gln Asn Ala Pro Thr Gly Leu Pro Val Glu Pro Val Gly
        35                  40                  45

Val Ala Ile Pro His Thr Asp Ser Lys Tyr Val Arg Gln Asn Ala Ile
    50                  55                  60

Ser Val Gly Ile Leu Ala Glu Pro Val Asn Phe Glu Asp Ala Gly Gly
65                  70                  75                  80

Glu Pro Asp Pro Val Pro Val Arg Val Val Phe Met Leu Ala Leu Gly
                85                  90                  95

Asn Trp Phe Asp Ile Thr Asn Val Leu Trp Trp Ile Lys Ala Val Ile
            100                 105                 110

Gln Asp Ala Asp Phe Met Gln Gln Leu Leu Arg Met Asn Asp Asp Glu
        115                 120                 125

Ile Tyr Gln Ser Ile Tyr Thr Arg Ile Ser Glu Ala Ala Gly Met Ala
    130                 135                 140

```
Gly Ile His Phe Arg Arg His Tyr Val Arg His Leu Gly
145                 150                 155
```

<210> SEQ ID NO 232
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

```
Gly Glu Ala Gln Arg Val Arg Gln Glu Ala Lys Glu Arg Met Lys Arg
1               5                   10                  15

Ala Val Glu Lys Phe Lys Lys Glu Leu Lys Glu Phe Asn Thr Glu Val
                20                  25                  30

Glu Lys Lys Glu Pro Arg Gln Gln Arg Ile Gln Lys Trp Glu Gln Ile
            35                  40                  45

Val Glu Glu Arg Ala Lys Lys Ala Glu Asp Val Lys Lys Val Gly
    50                  55                  60

Lys Glu Ala Ala Asp Arg Ala Ala Lys Leu Gly Gln Asp Pro Gln Val
65                  70                  75                  80

Asn Trp Phe Asp Ile Ser Gln Ile Leu Trp Asp Val Lys Lys Leu Thr
                85                  90                  95

Gln Glu Ala Ile Glu Glu Ile Arg Lys Ala Leu Glu Gln Met Arg Arg
            100                 105                 110

Trp Leu Gln Arg Gly
        115
```

<210> SEQ ID NO 233
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

```
Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
                20                  25                  30

Leu Ile Asn Asp Gly Met Val Val Ser Asp Phe Ala Asp His Val Ile
            35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Asp Ile Thr Asn Val Leu Trp Trp Ile Lys Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu
145                 150                 155
```

```
<210> SEQ ID NO 234
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
                20                  25                  30

Lys Gln Lys Glu Pro Arg Asp Asp Glu Ile Asn Arg Trp Ile Asp Ile
            35                  40                  45

Val Lys Lys Lys Ala Asp Glu Ala Lys Lys Arg Val Glu Glu Val Gly
        50                  55                  60

Asp Gln Ala Ala Asp Glu Ala Ala Gln Leu Gly Asn Asp Pro Asn Val
65                  70                  75                  80

Asn Trp Phe Asp Ile Thr Asn Val Leu Trp Asp Val Lys Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly Gly Gln Tyr Ile Lys Ala Asn Ser Lys Phe Ile
        115                 120                 125

Gly Ile Thr Glu Leu
    130

<210> SEQ ID NO 235
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
                20                  25                  30

Lys Gln Lys Glu Pro Arg Asp Asp Glu Ile Asn Arg Trp Ile Asp Ile
            35                  40                  45

Val Lys Lys Lys Ala Asp Glu Ala Lys Lys Arg Val Glu Glu Val Gly
        50                  55                  60

Asp Gln Ala Ala Asp Glu Ala Ala Gln Leu Gly Asn Asp Pro Asn Val
65                  70                  75                  80

Asn Trp Phe Ser Ile Thr Lys Val Leu Trp Asp Val Lys Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly Gly Gln Tyr Ile Lys Ala Asn Ser Lys Phe Ile
        115                 120                 125

Gly Ile Thr Glu Leu
    130

<210> SEQ ID NO 236
```

<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
                20                  25                  30

Lys Gln Lys Glu Pro Arg Asp Asp Glu Ile Asn Arg Trp Ile Asp Ile
            35                  40                  45

Val Lys Lys Lys Ala Asp Glu Ala Lys Arg Val Glu Glu Val Gly
    50                  55                  60

Asp Gln Ala Ala Asp Glu Ala Ala Gln Leu Gly Asn Asp Pro Asn Val
65                  70                  75                  80

Ser Trp Phe Asn Ile Ser Asn Val Leu Trp Asp Val Arg Lys Leu Thr
                85                  90                  95

Glu Lys Ala Ile Asn Asp Ile Asp Asp Ala Leu Lys Lys Met Lys Asp
                100                 105                 110

Trp Leu Glu Ser Gly Gly Gln Tyr Ile Lys Ala Asn Ser Lys Phe Ile
            115                 120                 125

Gly Ile Thr Glu Leu
        130

<210> SEQ ID NO 237
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
                20                  25                  30

Lys Gln Lys Glu Pro Arg Asp Asp Glu Ile Asn Arg Trp Ile Asp Ile
            35                  40                  45

Val Lys Lys Lys Ala Asp Glu Ala Lys Arg Val Glu Glu Val Gly
    50                  55                  60

Asp Gln Ala Ala Asp Glu Ala Ala Gln Leu Gly Asn Asp Pro Asn Val
65                  70                  75                  80

Asn Trp Phe Asp Ile Ser Arg Val Leu Trp Asp Val Lys Lys Leu Thr
                85                  90                  95

Glu Lys Ala Ile Asn Asp Ile Asp Asp Ala Leu Lys Lys Met Lys Asp
                100                 105                 110

Trp Leu Glu Ser Gly Gly Gln Tyr Ile Lys Ala Asn Ser Lys Phe Ile
            115                 120                 125

Gly Ile Thr Glu Leu
        130

<210> SEQ ID NO 238
<211> LENGTH: 133
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 238

Gly Lys Ala Asp Glu Val Arg Glu Lys Ala Arg Arg Met Glu Gln
1               5                   10                  15

Ala Val Glu Glu Phe Lys Arg Arg Leu Arg Gln Phe Glu Glu Lys Val
            20                  25                  30

Lys Gln Lys Glu Pro Arg Asp Asp Glu Ile Asn Arg Trp Ile Asp Ile
        35                  40                  45

Val Lys Lys Lys Ala Asp Glu Ala Lys Lys Arg Val Glu Glu Val Gly
50                  55                  60

Asp Gln Ala Ala Asp Glu Ala Ala Gln Leu Gly Asn Asp Pro Asn Val
65                  70                  75                  80

Asn Trp Phe Asp Ile Thr Gln Val Leu Trp Asp Val Lys Lys Leu Thr
                85                  90                  95

Glu Lys Ala Ile Asn Asp Ile Asp Asp Ala Leu Lys Lys Met Lys Asp
            100                 105                 110

Trp Leu Glu Ser Gly Gly Gln Tyr Ile Lys Ala Asn Ser Lys Phe Ile
        115                 120                 125

Gly Ile Thr Glu Leu
    130

<210> SEQ ID NO 239
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Asp Ile Thr Asn Val Leu Trp Trp Ile Lys Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu Gly Gly Gln Tyr Ile
145                 150                 155                 160

Lys Ala Asn Ser Lys Phe Ile Gly Ile Thr Glu Leu
                165                 170

<210> SEQ ID NO 240
```

<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 240

```
Asn Ala Met Gln Gly Ile His Phe Arg Arg His Tyr Val Arg His Leu
1               5                  10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Ser Ile Thr Lys Val Leu Trp Trp Ile Lys Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu Gly Gly Gln Tyr Ile
145                 150                 155                 160

Lys Ala Asn Ser Lys Phe Ile Gly Ile Thr Glu Leu
                165                 170
```

<210> SEQ ID NO 241
<211> LENGTH: 172
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 241

```
Asn Ala Met Gln Gly Ile His Phe Arg Arg His Tyr Val Arg His Leu
1               5                  10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Ser Trp Phe Asn Ile Ser Asn Val Leu Trp Trp Ile Arg Ala Val Ile
        115                 120                 125

Gln Asp Glu Asp Phe Met Gln Gln Leu Leu Val Met Asn Asp Asp Glu
    130                 135                 140
```

```
Ile Tyr Gln Ser Ile Tyr Thr Arg Ile Ser Glu Gly Gly Gln Tyr Ile
145                 150                 155                 160

Lys Ala Asn Ser Lys Phe Ile Gly Ile Thr Glu Leu
                165                 170

<210> SEQ ID NO 242
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95

Glu Pro Asp Pro Val Pro Val Arg Val Val Phe Met Leu Ala Leu Gly
            100                 105                 110

Asn Trp Phe Asp Ile Ser Arg Val Leu Trp Trp Ile Lys Ala Val Ile
        115                 120                 125

Gln Asp Glu Asp Phe Met Gln Gln Leu Leu Val Met Asn Asp Asp Glu
    130                 135                 140

Ile Tyr Gln Ser Ile Tyr Thr Arg Ile Ser Glu Gly Gly Gln Tyr Ile
145                 150                 155                 160

Lys Ala Asn Ser Lys Phe Ile Gly Ile Thr Glu Leu
                165                 170

<210> SEQ ID NO 243
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Asn Ala Met Gln Gly Ile His Phe Arg Arg His Tyr Val Arg His Leu
1               5                   10                  15

Pro Lys Glu Val Ser Gln Asn Asp Ile Ile Lys Ala Leu Ala Ser Pro
            20                  25                  30

Leu Ile Asn Asp Gly Met Val Val Ser Asp Phe Ala Asp His Val Ile
        35                  40                  45

Thr Arg Glu Gln Asn Phe Pro Thr Gly Leu Pro Val Glu Pro Val Gly
    50                  55                  60

Val Ala Ile Pro His Thr Asp Ser Lys Tyr Val Arg Gln Asn Ala Ile
65                  70                  75                  80

Ser Val Gly Ile Leu Ala Glu Pro Val Asn Phe Glu Asp Ala Gly Gly
                85                  90                  95
```

| | | | | | | | | | | | |
|---|---|---|---|---|---|---|---|---|---|---|---|
|Glu|Pro|Asp|Pro|Val|Pro|Val|Arg|Val|Val|Phe|Met|Leu|Ala|Leu|Gly|
| | | |100| | |105| | | | |110| | | | |
|Asn|Trp|Phe|Asp|Ile|Thr|Gln|Val|Leu|Trp|Trp|Ile|Lys|Ala|Val|Ile|
| | | | |115| | |120| | | | |125| | | |
|Gln|Asp|Glu|Asp|Phe|Met|Gln|Gln|Leu|Leu|Val|Met|Asn|Asp|Asp|Glu|
| | | | |130| | | |135| | | |140| | | |
|Ile|Tyr|Gln|Ser|Ile|Tyr|Thr|Arg|Ile|Ser|Glu|Gly|Gly|Gln|Tyr|Ile|
|145| | | | |150| | | | |155| | | | |160|
|Lys|Ala|Asn|Ser|Lys|Phe|Ile|Gly|Ile|Thr|Glu|Leu|
| | | | |165| | | |170| | | |

What is claimed is:

1. A 10E8 immunogen having the amino acid sequence comprising (a) 10E8_T298v2
(SEQ ID NO: 231)
GSEVSQNDIIKALASPLINDGMVVSDFADHVITREQNAPTGLPVEPVGVA

IPHTDSKYVRQNAISVGILAEPVNFEDAGGEPDPVPVRVVFMLALGNWFD

ITNVLWWIKAVIQDADFMQQLLRMNDDEIYQSIYTRISEAAGMAGIHFRR

HYVRHLG
or (b) 10E8_T93v2_RT1_1
(SEQ ID NO: 232)
GEAQRVRQEAKERMKRAVEKFKKELKEFNTEVEKKEPRQQRIQKWEQIVE

ERAKKAEDEVKKVGKEAADRAAKLGQDPQVNWFDISQILWDVKKLIQEAI

EEIRKALEQMRRWLQRG
or (c) 10E8_T93v2RT12-1
(SEQ ID NO: 201)
GKADEVREKARRRMEQAVEEFKRRLRQFEEKVKQKEPRDDEINRWIDIVK

KKADEAKKRVEEVGDQAADEAAQLGNDPNVNWFDITNVLWDVKKLTEKAI

NDIDDALKKMKDWLESG
or (d) 10E8_T93v2RT12-2
(SEQ ID NO: 202)
GKADEVREKARRRMEQAVEEFKRRLRQFEEKVKQKEPRDDEINRWIDIVK

KKADEAKKRVEEVGDQAADEAAQLGNDPNVNWFSITKVLWDVKKLTEKAI

NDIDDALKKMKDWLESG
or (e) 10E8_T93v2RT12-3
(SEQ ID NO: 203)
GKADEVREKARRRMEQAVEEFKRRLRQFEEKVKQKEPRDDEINRWIDIVK

KKADEAKKRVEEVGDQAADEAAQLGNDPNVSWFNISNVLWDVRKLTEKAI

NDIDDALKKMKDWLESG
or (f) 10E8_T93v2RT12-4
(SEQ ID NO: 204)
GKADEVREKARRRMEQAVEEFKRRLRQFEEKVKQKEPRDDEINRWIDIVK

KKADEAKKRVEEVGDQAADEAAQLGNDPNVNWFDISRVLWDVKKLTEKAI

NDIDDALKKMKDWLESG
or (g) 10E8_T93v2RT12-5
(SEQ ID NO: 205)
GKADEVREKARRRMEQAVEEFKRRLRQFEEKVKQKEPRDDEINRWIDIVK

KKADEAKKRVEEVGDQAADEAAQLGNDPNVNWFDITQVLWDVKKLTEKAI

NDIDDALKKMKDWLESG
or (h) 10E8_T117v2-1
(SEQ ID NO: 233)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITNVLWWIKAVIQDEDFMQQLLVMNDDEIYQSIY

TRISE
or (i) 10E8_T117v2-2
(SEQ ID NO: 207)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFSITKVLWWIKAVIQDEDFMQQLLVMNDDEIYQSIY

TRISE
or (j) 10E8_1117v2-3
(SEQ ID NO: 208)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGSWFNISNVLWWIRAVIQDEDFMQQLLVMNDDEIYQSIY

TRISE
or (k) 10E8_T117v2-4
(SEQ ID NO: 209)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDISRVLWWIKAVIQDEDFMQQLLVMNDDEIYQSIY

TRISE
or (l) 10E8_T117v2-5
(SEQ ID NO: 210)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

-continued

VPVRVVFMLALGNWFDITQVLWWIKAVIQDEDFMQQLLVMNDDEIYQSIY

TRISE or (m) 10E8_T93v2RT12-1_P2

(SEQ ID NO: 234)
GKADEVREKARRRMEQAVEEFKRRLRQFEEKVKQKEPRDDEINRWIDIVK

KKADEAKKRVEEVGDQAADEAAQLGNDPNVNWFDITNVLWDVKKLTEKAI

NDIDDALKKMKDWLESGGQYIKANSKFIGITEL or (n) 10E8_T93v2RT12-2_P2

(SEQ ID NO: 235)
GKADEVREKARRRMEQAVEEFKRRLRQFEEKVKQKEPRDDEINRWIDIVK

KKADEAKKRVEEVGDQAADEAAQLGNDPNVNWFSITKVLWDVKKLTEKAI

NDIDDALKKMKDWLESGGQYIKANSKFIGITEL or (o) 10E8_T93v2RT12-3_P2

(SEQ ID NO: 236)
GKADEVREKARRRMEQAVEEFKRRLRQFEEKVKQKEPRDDEINRWIDIVK

KKADEAKKRVEEVGDQAADEAAQLGNDPNVSWFNISNVLWDVRKLTEKAI

NDIDDALKKMKDWLESGGQYIKANSKFIGITEL or (p) 10E8_T93v2RT12-4_P2

(SEQ ID NO: 237)
GKADEVREKARRRMEQAVEEFKRRLRQFEEKVKQKEPRDDEINRWIDIVK

KKADEAKKRVEEVGDQAADEAAQLGNDPNVNWFDISRVLWDVKKLTEKAI

NDIDDALKKMKDWLESGGQYIKANSKFIGITEL or (q) 10E8_T93v2RT12-5_P2

(SEQ ID NO: 238)
GKADEVREKARRRMEQAVEEFKRRLRQFEEKVKQKEPRDDEINRWIDIVK

KKADEAKKRVEEVGDQAADEAAQLGNDPNVNWFDITQVLWDVKKLTEKAI

NDIDDALKKMKDWLESGGQYIKANSKFIGITEL or (r) 10E8_T117v2-1_P2

(SEQ ID NO: 239)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITNVLWWIKAVIQDEDFMQQLLVMNDDEIYQSIY

TRISEGGQYIKANSKFIGITEL or (s) 10E8_T117v2-2_P2

(SEQ ID NO: 240)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFSITKVLWWIKAVIQDEDFMQQLLVMNDDEIYQSIY

TRISEGGQYIKANSKFIGITEL or (t) 10E8_T117v2-3_P2

(SEQ ID NO: 241)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGSWFNISNVLWWIRAVIQDEDFMQQLLVMNDDEIYQSIY

TRISEGGQYIKANSKFIGITEL or (u) 10E8_T117v2-4_P2

(SEQ ID NO: 242)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDISRVLWWIKAVIQDEDFMQQLLVMNDDEIYQSIY

TRISEGGQYIKANSKFIGITEL or (v) 10E8_T117v2-5_P2

(SEQ ID NO: 243)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITQVLWWIKAVIQDEDFMQQLLVMNDDEIYQSIY

TRISEGGQYIKANSKFIGITEL or (w) 10E8_T117v2-1_RSF1

(SEQ ID NO: 224)
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

VPVRVVFMLALGNWFDITNVLWWIKAVIQDDEFMKRLLYMTDDKIYESIR

KRIYDLE or (x) 10E8_T117v2-2_RSF1

(SEQ ID NO: 225)
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

VPVRVVFMLALGNWFSITKVLWWIKAVIQDDEFMKRLLYMTDDKIYESIR

KRIYD or (y) 10E8_T117v2-3_RSF1

(SEQ ID NO: 226)
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

VPVRVVFMLALGSWFNISNVLWWIRAVIQDDEFMKRLLYMTDDKIYESIR

KRIYD or (z) 10E8_T117v2-4_RSF1

(SEQ ID NO: 227)
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

VPVRVVFMLALGNWFDISRVLWWIKAVIQDDEFMKRLLYMTDDKIYESIR

KRIYD or (aa) 10E8_T117v2-5_RSF1

(SEQ ID NO: 228)
NAMAGIVFRKHYVRHLGKTVTQNEIIRALAAPLISDGMVVKDFADHVIKR

EEQNPTGLPVQPVGVAIPHTDSKYVYYNAISVGILQEPVAFEDAGGDGRP

-continued

VPVRVVFMLALGNWFDITQVLWWIKAVIQDDEFMKRLLYMTDDKIYESIR

KRIYD
or (bb) 10E8_T117v2-1_g28_g91012
(SEQ ID NO: 229)
NAMQGIHFRRHYVRHLPKNVSQNDIIKALASPLINDGMVVSDFADHVITR

ENNSPTGLPVEPVGVAIPHTDSKYVNQSAISVGILAEPVNFEDANGTPDP

VPVRVVFMLALGNWFDITNVLWWIKAVIQDEDFMQQLLNMSDDEIYQSIY

TRISE
or (cc) 10E8_T117v2-1_g258_g91012
(SEQ ID NO: 230)
NAMQGIHFRRHYVRHLPKNVSQNDIIKALASPLINDGMVVSDFADHVITR

ENNSPTGLPVEPVGVAIPHTDSKYVNQSAISVGILAEPVNFEDANGTPDP

VPVRVVFMLALGNWFDITNVLWWIKAVIQNASFMQQLLNMSDDEIYQSIY

TRISE.

2. A protein that binds to broadly neutralizing antibody 10E8 against HIV having an amino acid sequence comprising:

(a) 10E8_T298v2
(SEQ ID NO: 231)
GSEVSQNDIIKALASPLINDGMVVSDFADHVITREQNAPTGLPVEPVGVA

IPHTDSKYVRQNAISVGILAEPVNFEDAGGEPDPVPVRVVFMLALGNWFD

ITNVLWWIKAVIQDADFMQQLLRMNDDEIYQSIYTRISEAAGMAGIHFRR

HYVRHLG or 95% identity thereof
or (b) 10E8_T93v2_RT1_1
(SEQ ID NO: 232)
GEAQRVRQEAKERMKRAVEKFKKELKEFNTEVEKKEPRQQRIQKWEQIVE

ERAKKAEDEVKKVGKEAADRAAKLGQDPQVNWFDISQILWDVKKLTQEIE

EIRKALEQMRRWLQRG or 95% identity thereof
or (c) 10E8_T93v2RT12-1
(SEQ ID NO: 201)
GKADEVREKARRRMEQAVEEFKRRLRQFEEKVKQKEPRDDEINRWIDIVK

KKADEAKKRVEEVGDQAADEAAQLGNDPNVNWFDITNVLWDVKKLTEKAI

NDIDDALKKMKDWLESG or 95% identity thereof
or (d) 10E8_T93v2RT12-2
(SEQ ID NO: 202)
GKADEVREKARRRMEQAVEEFKRRLRQFEEKVKQKEPRDDEINRWIDIVK

KKADEAKKRVEEVGDQAADEAAQLGNDPNVNWFSITKVLWDVKKLTEKAI

NDIDDALKKMKDWLESG or 95% identity thereof
or (e) 10E8_T93v2RT12-3
(SEQ ID NO: 203)
GKADEVREKARRRMEQAVEEFKRRLRQFEEKVKQKEPRDDEINRWIDIVK

KKADEAKKRNEEVGDQAADEAAQLGNDPNVSWFNISNVLWDVRKLTEKAI

NDIDDALKKMKDWLESG or 95% identity thereof
or

-continued (f) 10E8_ T93v2RT12-4
(SEQ ID NO: 204)
GKADEVREKARRRMEQAVEEFKRRLRQFEEKVKQKEPRDDEINRWIDIVK

KKADEAKKRVEEVGDQAADEAAQLGNDPNVNWFDISRVLWDVKKTELKAI

NDIDDALKKMKDWLESG or 95% identity thereof
or (g) 10E8_T93v2RT12-5
(SEQ ID NO: 205)
GKADEVREKARRRMEQAVEEFKRRLRQFEEKVKQKEPRDDEINRWIDIVK

KKADEAKKRVEEVGDQAADEAAQLGNDPNVNWFDITQVLWDVKKLTEKAI

NDIDDALKKMKDWLESG or 95% identity thereof
or (h) 10E8_T117v2-1
(SEQ ID NO: 233)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITNVLWWIKAVIQDEDFMQQLLVMNDDEIYQSIY

TRISE or 95% identity thereof
or (i) 10E8_T117v2-2
(SEQ ID NO: 207)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFSITKVLWWIKAVIQDEDFMQQLLVMNDDEIYQSIY

TRISE or 95% identity thereof
or (j) 10E8_T117v2-3
(SEQ ID NO: 208)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGSWFNISNVLWWIRAVIQDEDFMQQLLVMNDDEIYQSIY

TRISE or 95% identity thereof
or (k) 10E8_T117v2-4
(SEQ ID NO: 209)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDISRVLWWIKAVIQDEDFMQQLLVMNDDEIYQSIY

TRISE or 95% identity thereof
or (l) 10E8_T117v2-5
(SEQ ID NO: 210)
NAMQGIHFRRHYVRHLPKEVSQNDIIKALASPLINDGMVVSDFADHVITR

EQNFPTGLPVEPVGVAIPHTDSKYVRQNAISVGILAEPVNFEDAGGEPDP

VPVRVVFMLALGNWFDITQVLWWIKAVIQDEDFMQQLLVMNDDEIYQSIY

TRISE or 95% identity thereof
or (m) 10E8_T93v2RT12-1_P2
(SEQ ID NO: 234)
GKADEVREKARRRMEQAVEEFKRRLRQFEEKVKQKEPRDDEINRWIDIVK

KKADEAKKRVEEVGDQAADEAAQLGNDPNVNWFDITNVLWDVKKLTEKAI

-continued

NDIDDALKKMKDWLESGGQYIKANSKFIGITEL or 95% identity thereof or (n) 10E8_T93v2RT12-2_P2
(SEQ ID NO: 235)
GKADEVREKARRRMEQAVEEFKRRLRQFEEKVKQKEPRDDEINRWIDIVK
KKADEAKKRVEEVGDQAADEAAQLGNDPNVNWFSITKVLWDVKKLTEKAI
NDIDDALKKMKDWLESGGQYIKANSKFIGITEL or 95% identity thereof or (o) 10E8_T93v2RT12-3_P2
(SEQ ID NO: 236)
GKADEVREKARRRMEQAVEEFKRRLRQFEEKVKQKEPRDDEINRWIDIVK
KKADEAKKRVEEVGDQAADEAAQLGNDPNVSWFNISNVLWDVRKLTEKAI
NDIDDALKKMKDWLESGGQYIKANSKFIGITEL or 95% identity thereof or (p) 10E8_T93v2RT12-4_P2
(SEQ ID NO: 237)
GKADEVREKARRRMEQAVEEFKRRLRQFEEKVKQKEPRDDEINRWIDIVK
KKADEAKKRVEEVGDQAADEAAQLGNDPNVNWFDISRVLWDVKKLTEKAI
NDIDDALKKMKDWLESGGQYIKANSKFIGITEL or 95% identity thereof or (q) 10E8_T93v2RT12-5_P2
(SEQ ID NO: 238)
GKADEVREKARRRMEQAVEEFKRRLRQFEEKVKQKEPRDDEINRWIDIVK
KKADEAKKRVEEVGDQAADEAAQLGNDPNVNWFDITQVLWDVKKLTEKAI
NDIDDALKKMKDWLESGGQYIKANSKFIGITEL or 95% identity thereof or (r) 10E8_T117v2-1_P2
(SEQ ID NO: 239)
NAMQGIHFRRHYVRHLPKEVSQNDIIKALASPLINDGMVVSDFADHVITR
EQNFPTGLPVEPVGVAIPHTDSKYVRQNAISVGILAEPVNFEDAGGEPDP
VPVRVVFMLALGNWFDITNVLWWIKAVIQDEDFMQQLLVMNDDEIYQSIY
TRISEGGQYIKANSKFIGITEL or 95% identity thereof or (s) 10E8_T117v2-2_P2
(SEQ ID NO: 240)
NAMQGIHFRRHYVRHLPKEVSQNDIIKALASPLINDGMVVSDFADHVITR
EQNFPTGLPVEPVGVAIPHTDSKYVRQNAISVGILAEPVNFEDAGGEPDP
VPVRVVFMLALGNWFSITKVLWWIKAVIQDEDFMQQLLVMNDDEIYQSIY
TRISEGGQYIKANSKFIGITEL or 95% identity thereof or (t) 10E8_T117v2-3_P2
(SEQ ID NO: 241)
NAMQGIHFRRHYVRHLPKEVSQNDIIKALASPLINDGMVVSDFADHVITR
EQNFPTGLPVEPVGVAIPHTDSKYVRQNAISVGILAEPVNFEDAGGEPDP
VPVRVVFMLALGSWFNISNVLWWIRAVIQDEDFMQQLLVMNDDEIYQSIY
TRISEGGQYIKANSKFIGITEL or 95% identity thereof or (u) 10E8_T117v2-4_P2
(SEQ ID NO: 242)
NAMQGIHFRRHYVRHLPKEVSQNDIIKALASPLINDGMVVSDFADHVITR
EQNFPTGLPVEPVGVAIPHTDSKYVRQNAISVGILAEPVNFEDAGGEPDP
VPVRVVFMLALGNWFDISRVLWWIKAVIQDEDFMQQLLVMNDDEIYQSIY
TRISEGGQYIKANSKFIGITEL or 95% identity thereof or (v) 10E8_T117v2-5_P2
(SEQ ID NO: 243)
NAMQGIHFRRHYVRHLPKEVSQNDIIKALASPLINDGMVVSDFADHVITR
EQNFPTGLPVEPVGVAIPHTDSKYVRQNAISVGILAEPVNFEDAGGEPDP
VPVRVVFMLALGNWFDITQVLWWIKAVIQDEDFMQQLLVMNDDEIYQSIY
TRISEGGQYIKANSKFIGITEL or 95% identity thereof or (w) 10E8_T117v2-1_RSF1
(SEQ ID NO: 224)
NAMAGIVFRKHYVRHLGKTVTQNEIIRALAAPLISDGMVVKDFADHVIKR
EEQNPTGLPVQPVGVAIPHTDSKYVYYNAISVGILQEPVAFEDAGGDGRP
VPVRVVFMLALGNWFDITNVLWWIKAVIQDDEFMKRLLYMTDDKIYESIR
KRIYDLE or 95% identity thereof or (x) 10E8_T117v2-2_RSF1
(SEQ ID NO: 225)
NAMAGIVFRKHYVRHLGKTVTQNEIIRALAAPLISDGMVVKDFADHVIKR
EEQNPTGLPVQPVGVAIPHTDSKYVYYNAISVGILQEPVAFEDAGGDGRP
VPVRVVFMLALGNWFSITKVLWWIKAVIQDDEFMKRLLYMTDDKIYESIR
KRIYD or 95% identity thereof or (y) 10E8_T117v2-3_RSF1
(SEQ ID NO: 226)
NAMAGIVFRKHYVRHLGKTVTQNEIIRALAAPLISDGMVVKDFADHVIKR
EEQNPTGLPVQPVGVAIPHTDSKYVYYNAISVGILQEPVAFEDAGGDGRP
VPVRVVFMLALGSWFNISNVLWWIRAVIQDDEFMKRLLYMTDDKIYESIR
KRIYD or 95% identity thereof or (z) 10E8_T117v2-4_RSF1
(SEQ ID NO: 227)
NAMAGIVFRKHYVRHLGKTVTQNEIIRALAAPLISDGMVVKDFADHVIKR
EEQNPTGLPVQPVGVAIPHTDSKYVYYNAISVGILQEPVAFEDAGGDGRP
VPVRVVFMLALGNWFDISRVLWWIKAVIQDDEFMKRLLYMTDDKIYESIR
KRIYD or 95% identity thereof or (aa) 10E8_T117v2-5_RSF1
(SEQ ID NO: 228)
NAMAGIVFRKHYVRHLGKTVTQNEIIRALAAPLISDGMVVKDFADHVIKR
EEQNPTGLPVQPVGVAIPHTDSKYVYYNAISVGILQEPVAFEDAGGDGRP -continued

VPVRVVFMLALGNWFDITQVLWWIKAVIQDDEFMKRLLYMTDDKIYESIR

KRIYD or 95% identity thereof
or (bb) 10E8_T117v2-1_g28_g91012
                                    (SEQ ID NO: 229)
NAMQGIHFRRHYVRHLPKNVSQNDIIKALASPLINDGMVVSDFADHVITR

ENNSPTGLPVEPVGVAIPHTDSKYVNQSAISVGILAEPVNFEDANGTPDP

VPVRVVFMLALGNWFDITNVLWWIKAVIQDEDFMQQLLNMSDDEIYQSIY

TRISE or 95% identity thereof
or (cc) 10E8_T117v2-1_g258_g91012
                                    (SEQ ID NO: 230)
NAMQGIHFRRHYVRHLPKNVSQNDIIKALASPLINDGMVVSDFADHVITR

ENNSTTGLPVEPVGVAIPHTDSKYVNQSAISVGILAEPVNFEDANGTPDP

VPVRVVFMLALGNWFDITNVLWWIKAVIQNASFMQQLLNMSDDEIYQSIY

TRISE or 95% identity thereof.

3. A nucleic acid molecule encoding a protein of claim 1.

4. A method for eliciting a human anti-HIV antibody comprising systemically administering to a host mammal or avian an effective amount of the protein of claim 1 to elicit the antibody.

5. The method of claim 4 wherein the host is a mammal.

6. A nucleic acid molecule encoding a protein of claim 2.

7. A method for eliciting a human anti-HIV antibody comprising systemically administering to a host mammal or avian an effective amount of the protein of claim 2 to elicit the antibody.

8. The method of claim 7 wherein the host is a mammal.

\* \* \* \* \*